US006827863B2

United States Patent
Dolecek et al.

(10) Patent No.: US 6,827,863 B2
(45) Date of Patent: Dec. 7, 2004

(54) FLEXIBLE CENTRIFUGE BAG AND METHODS OF USE

(75) Inventors: Victor D. Dolecek, Englewood, CO (US); David Malcolm, Parker, CO (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/462,426

(22) Filed: Jun. 16, 2003

(65) Prior Publication Data

US 2004/0058794 A1 Mar. 25, 2004

Related U.S. Application Data

(62) Division of application No. 09/832,711, filed on Apr. 9, 2001, now Pat. No. 6,579,219.

(51) Int. Cl.$^7$ ............................................. B01D 17/038
(52) U.S. Cl. ..................... 210/787; 210/512.1; 210/789; 494/27; 494/37; 494/38; 494/45; 604/8; 604/10
(58) Field of Search ............................ 210/91, 94, 143, 210/512.1, 787–789; 494/1, 2, 10, 23, 27–29, 37, 38, 43, 45, 60; 604/6.01, 8, 10

(56) References Cited

U.S. PATENT DOCUMENTS

| | | |
|---|---|---|
| 3,326,458 A | 6/1967 | Meryman et al. |
| 3,724,747 A | 4/1973 | Unger et al. |
| 3,987,961 A | 10/1976 | Sinn et al. |
| 4,007,871 A | 2/1977 | Jones et al. |
| 4,010,894 A * | 3/1977 | Kellogg et al. ............... 494/45 |
| 4,268,393 A | 5/1981 | Persidsky et al. |
| 4,296,882 A | 10/1981 | Kobayashi |
| 4,322,298 A | 3/1982 | Persidsky |
| 4,447,220 A | 5/1984 | Eberle |
| 4,584,933 A * | 4/1986 | Price ......................... 99/450.4 |
| 4,720,284 A * | 1/1988 | McCarty ...................... 494/37 |
| 5,076,911 A | 12/1991 | Brown et al. |
| 5,217,426 A | 6/1993 | Bacehowski et al. |
| 5,316,540 A | 5/1994 | McMannis et al. |
| 6,596,181 B2 * | 7/2003 | Dolecek et al. ............. 210/787 |

FOREIGN PATENT DOCUMENTS

DE    2658926 A1    6/1978

* cited by examiner

*Primary Examiner*—Joseph Drodge
(74) *Attorney, Agent, or Firm*—Thomas G. Berry; Jeffrey J. Hohenshell

(57) ABSTRACT

A flexible, disposable centrifuge bag for receiving and holding a fluid sample, comprising one or more tubes and upper and lower flexible sheets having doughnut shaped configurations. The upper and lower sheets are superimposed and completely sealed together at their outer perimeters to define an outer perimeter of the centrifuge bag. The inner perimeter of the bag defines a central core. The tubes are sandwiched between the upper and lower sheets and extend from the central core of the centrifuge bag. The upper and lower sheets are sealed together at their inner perimeters such that the tubes are sealed between said upper and lower sheets at the inner perimeter. The bag may be used to harvest platelet rich plasma from whole blood in either a batch method or while simultaneously infusing additional aliquots of whole blood into the bag during centrifugation.

99 Claims, 39 Drawing Sheets

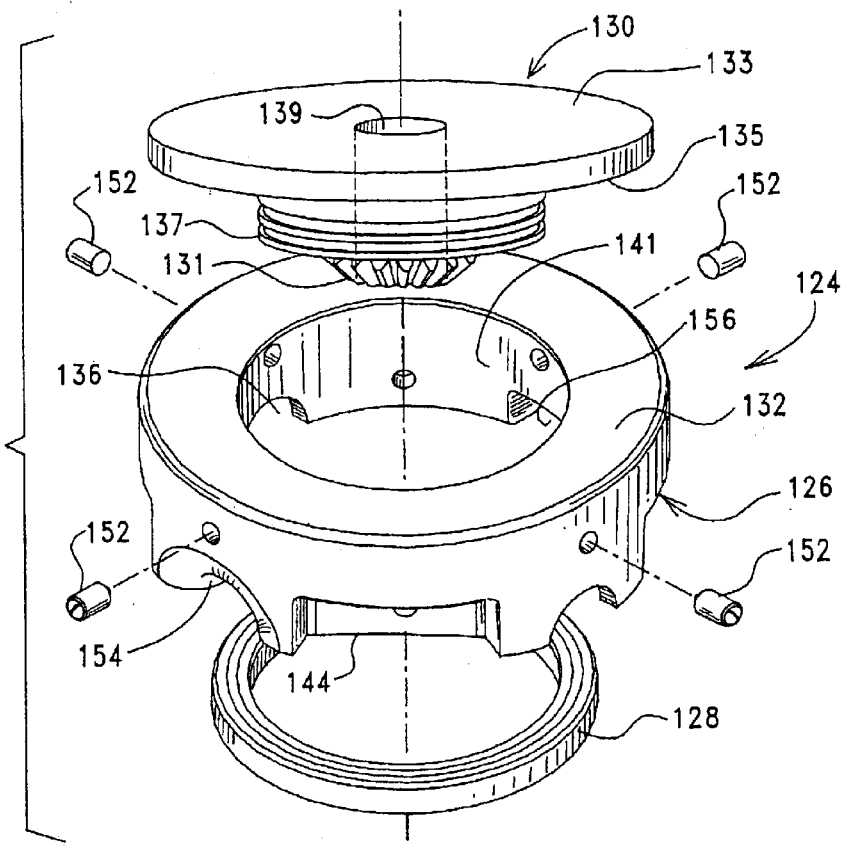
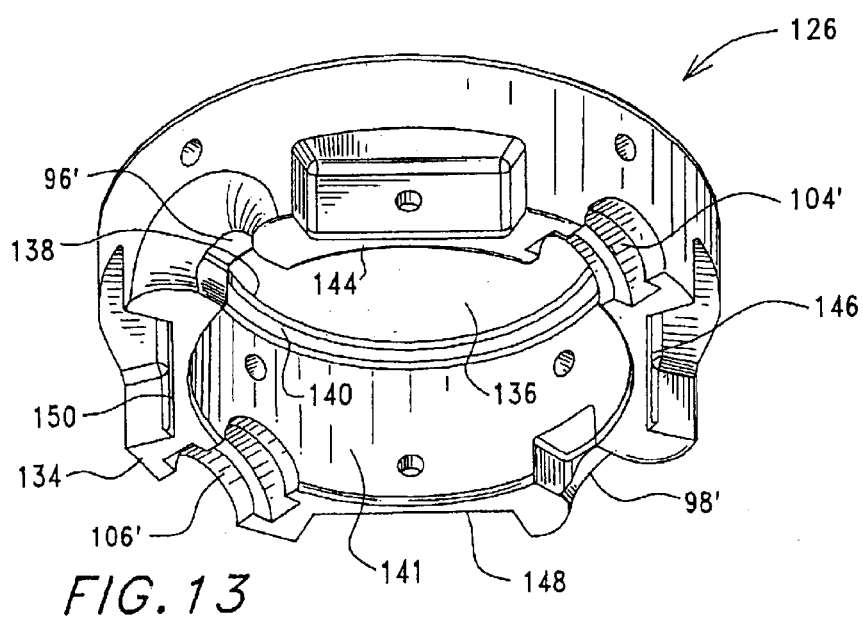

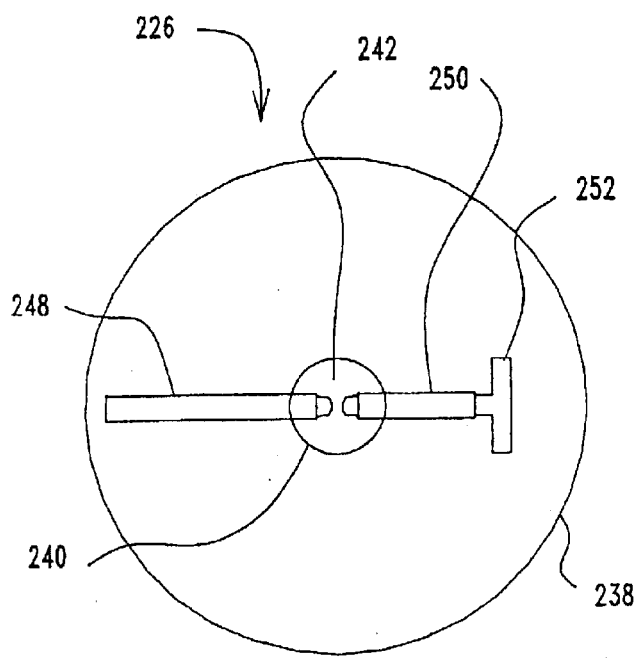
FIG.25
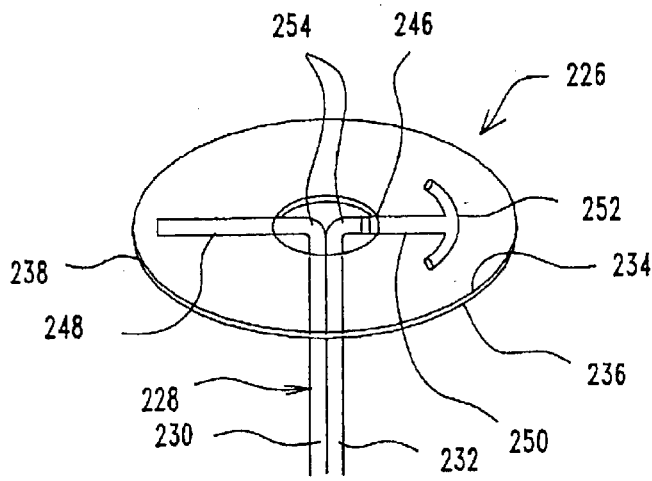
FIG.26
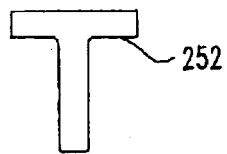
FIG.27
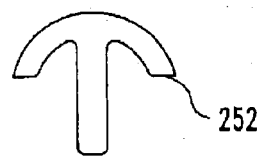
FIG.28
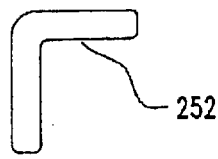
FIG.29
FIG.30
FIG.31

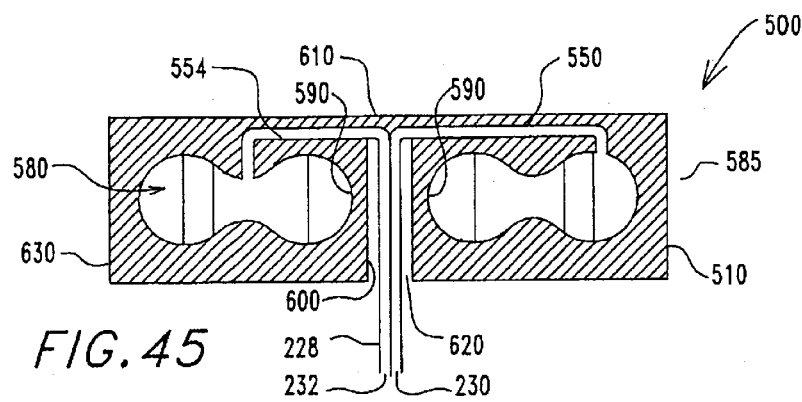
FIG.45
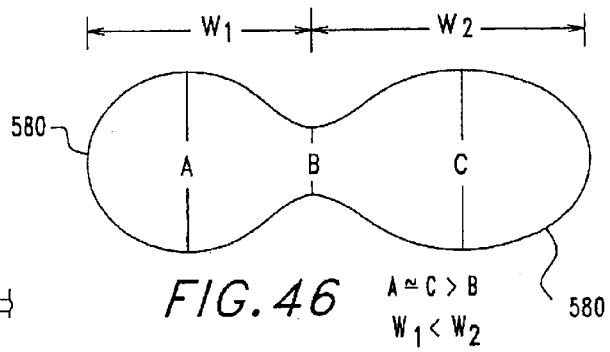
FIG.46  $A \simeq C > B$  $W_1 < W_2$
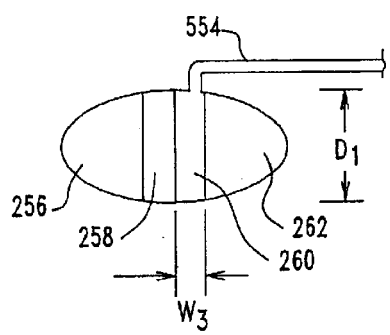
FIG.44
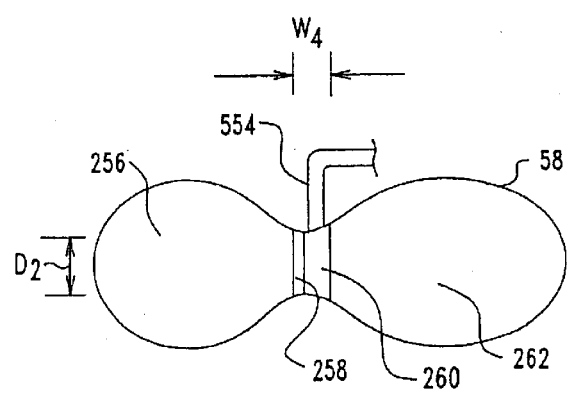
FIG.47
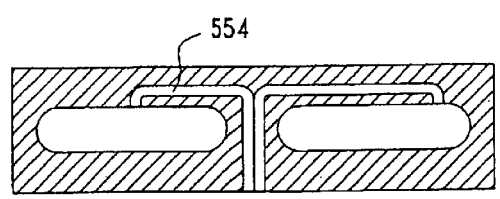
FIG.43

FLEXIBLE CENTRIFUGE BAG AND METHODS OF USE

CROSS-REFERENCED TO RELATED APPLICATIONS

This application is a Divisional of U.S. patent application Ser. No. 09/832,711, filed Apr. 9, 2001, now U.S. Pat. No. 6,579,219, the entire content of which is specifically incorporated herein by reference.

BACKGROUND OF THE INVENTION

1. Field of the Invention

This invention relates to novel methods, devices and apparatuses for the centrifugal separation of a liquid into its components of varying specific gravities, and is more particularly directed toward a blood separation device useful, for example, in the separation of blood components for use in various therapeutic regimens.

2. Description of the State of Art

Centrifugation utilizes the principle that particles suspended in solution will assume a particular radial position within the centrifuge rotor based upon their respective densities and will therefore separate when the centrifuge is rotated at an appropriate angular velocity for an appropriate period of time. Centrifugal liquid processing systems have found applications in a wide variety of fields. For example, centrifugation is widely used in blood separation techniques to separate blood into its component parts, that is, red blood cells, platelets, white blood cells, and plasma.

The liquid portion of the blood, referred to as plasma, is a protein-salt solution in which red and white blood cells and platelets are suspended. Plasma, which is 90 percent water, constitutes about 55 percent of the total blood volume. Plasma contains albumin (the chief protein constituent), fibrinogen (responsible, in part, for the clotting of blood), globulins (including antibodies) and other clotting proteins. Plasma serves a variety of functions, from maintaining a satisfactory blood pressure and providing volume to supplying critical proteins for blood clotting and immunity. Plasma is obtained by separating the liquid portion of blood from the cells suspended therein.

Red blood cells (erythrocytes) are perhaps the most recognizable component of whole blood. Red blood cells contain hemoglobin, a complex iron-containing protein that carries oxygen throughout the body while giving blood its red color. The percentage of blood volume composed of red blood cells is called the "hematocrit."

White blood cells (leukocytes) are responsible for protecting the body from invasion by foreign substances such as bacteria, fungi and viruses. Several types of white blood cells exist for this purpose, such as granulocytes and macrophages, which protect against infection by surrounding and destroying invading bacteria and viruses, and lymphocytes, which aid in the immune defense.

Platelets (thrombocytes) are very small cellular components of blood that help the clotting process by sticking to the lining of blood vessels. Platelets are vital to life, because they help prevent both massive blood loss resulting from trauma and blood vessel leakage that would otherwise occur in the course of normal, day-to-day activity.

If whole blood is collected and prevented from clotting by the addition of an appropriate anticoagulant, it can be centrifuged into its component parts. Centrifugation will result in the red blood cells, which weigh the most, packing to the most outer portion of the rotating container, while plasma, being the least dense will settle in the central portion of the rotating container. Separating the plasma and red blood cells is a thin white or grayish layer called the buffy coat. The buffy coat layer consists of the white blood cells and platelets, which together make up about 1 percent of the total blood volume.

These blood components, discussed above, may be isolated and utilized in a wide range of diagnostic and therapeutic regimens. For example, red blood cells are routinely transfused into patients with chronic anemia resulting from disorders such as kidney failure, malignancies, or gastrointestinal bleeding and those with acute blood loss resulting from trauma or surgery. The plasma component is typically frozen by cryoprecipitation and then slowly thawed to produce cryoprecipitated antihemophiliac factor (AHF), which is rich in certain clotting factors, including Factor VIII, fibrinogen, von Willebrand factor and Factor XIII. Cryoprecipitated AHF is used to prevent or control bleeding in individuals with hemophilia and von Willebrand's disease. Platelets and white blood cells, which are found in the buffy layer component, can be used to treat patients with abnormal platelet function (thrombocytopenia) and patients that are unresponsive to antibiotic therapy, respectively.

Various techniques and apparatus have been developed to facilitate the collection of whole blood and the subsequent separation of therapeutic components therefrom. Centrifugal systems, also referred to as blood-processing systems, generally fall into two categories, discontinuous-flow and continuous-flow devices.

In discontinuous-flow systems, whole blood from the donor or patient flows through a conduit into the rotor or bowl where component separation takes place. These systems employ a bowl-type rotor with a relatively large (typically 200 ml or more) volume that must be filled with blood before any of the desired components can be harvested. When the bowl is full, the drawing of fresh blood is stopped, the whole blood is separated into its components by centrifugation, and the unwanted components are returned to the donor or patient through the same conduit intermittently, in batches, rather than on a continuous basis. When the return has been completed, whole blood is again drawn from the donor or patient, and a second cycle begins. This process continues until the required amount of the desired component has been collected.

Discontinuous-flow systems have the advantage that the rotors are relatively small in diameter but have the disadvantage that the extracorporeal volume (i.e., the amount of blood that is out of the donor at any given time during the process) is large. This, in turn, makes it difficult or impossible to use discontinuous systems on people whose size and weight will not permit the drawing of the amount of blood required to fill the rotor. Discontinuous-flow devices are used for the collection of platelets and/or plasma, and for the concentration and washing of red blood cells. They are used to reconstitute previously frozen red blood cells and to salvage red blood cells lost intraoperatively. Because the bowls in these systems are rigid and have a fixed volume, however, it is difficult to control the hematocrit of the final product, particularly if the amount of blood salvaged is insufficient to fill the bowl with red blood cells.

One example of a discontinuous-flow system is disclosed by McMannis, et al., in his U.S. Pat. No. 5,316,540, and is a variable volume centrifuge for separating components of a fluid medium, comprising a centrifuge that is divided into upper and lower chambers by a flexible membrane, and a flexible processing container bag positioned in the upper chamber of the centrifuge. The McMannis, et al., system varies the volume of the upper chamber by pumping a hydraulic fluid into the lower chamber, which in turn raises the membrane and squeezes the desired component out of the centrifuge. The McMannis, et al., system takes up a fairly large amount of space, and its flexible pancake-shaped rotor is awkward to handle. The McMannis, et al., system does not permit the fluid medium to flow into and out of the processing bag at the same time, nor does it permit fluid medium to be pulled out of the processing bag by suction.

In continuous-flow systems, whole blood from the donor or patient also flows through one conduit into the spinning rotor where the components are separated. The component of interest is collected and the unwanted components are returned to the donor through a second conduit on a continuous basis as more whole blood is being drawn. Because the rate of drawing and the rate of return are substantially the same, the extracorporeal volume, or the amount of blood that is out of the donor or patient at any given time in the procedure, is relatively small. These systems typically employ a belt-type rotor, which has a relatively large diameter but a relatively small (typically 100 mL or less) processing volume. Although continuous-flow systems have the advantage that the amount of blood that must be outside the donor or patient can be relatively small, they have the disadvantage that the diameter of the rotor is large. These systems are, as a consequence, large. Furthermore, they are complicated to set up and use. These devices are used almost exclusively for the collection of platelets.

Continuous-flow systems are comprised of rotatable and stationary parts that are in fluid communication. Consequently, continuous-flow systems utilize either rotary seals or a J-loop. A variety of types of rotary centrifuge seals have been developed. Some examples of rotary centrifuge seals which have proven to be successful are described in U.S. Pat. Nos. 3,409,203 and 3,565,330, issued to Latham. In these patents, rotary seals are disclosed which are formed from a stationary rigid low friction member in contact with a moving rigid member to create a dynamic seal, and an elastomeric member which provides a resilient static seal as well as a modest closing force between the surfaces of the dynamic seal.

Another rotary seal suitable for use in blood-processing centrifuges is described in U.S. Pat. No. 3,801,142 issued to Jones, et al. In this rotary seal, a pair of seal elements having confronting annular fluid-tight sealing surfaces of non-corrodible material are provided. These are maintained in a rotatable but fluid-tight relationship by axial compression of a length of elastic tubing forming one of the fluid connections to these seal elements.

Related types of systems, which incorporate rotatable, disposable annular separation chambers, coupled via rotary seals to stationary tubing members are disclosed in U.S. Pat. Nos. 4,387,848; 4,094,461; 4,007,871; and 4,010,894.

One drawback present in the above-described continuous-flow systems has been their use of a rotating seal or coupling element between that portion of the system carried by the centrifuge rotor and that portion of the system which remains stationary. While such rotating seals have provided generally satisfactory performance, they have been expensive to manufacture and have unnecessarily added to the cost of the flow systems. Furthermore, such rotating seals introduce an additional component into the system which if defective can cause contamination of the blood being processed.

One flow system heretofore contemplated to overcome the problem of the rotating seal utilizes a rotating carriage on which a single housing is rotatably mounted. An umbilical cable extending to the housing from a stationary point imparts planetary motion to the housing and thus prevents the cable from twisting. To promote the desired ends of sterile processing and avoid the disadvantages of a discontinuous-flow system within a single sealed system, a family of dual member centrifuges can be used to effect cell separation. One example of this type of centrifuge is disclosed in U.S. Pat. No. RE 29,738 to Adams entitled "Apparatus for Providing Energy Communication Between a Moving and a Stationary Terminal." As is now well known, due to the characteristics of such dual member centrifuges, it is possible to rotate a container containing a fluid, such as a unit of donated blood and to withdraw a separated fluid component, such as plasma, into a stationary container, outside of the centrifuge without using rotating seals. Such container systems utilize a J-loop and can be formed as closed, sterile transfer sets.

The Adams patent discloses a centrifuge having an outer rotatable member and an inner rotatable member. The inner member is positioned within and rotatably supported by the outer member. The outer member rotates at one rotational velocity, usually called "one omega," and the inner rotatable member rotates at twice the rotational velocity of the outer housing or "two omega." There is thus a one-omega difference in rotational speed of the two members. For purposes of this document, the term "dual member centrifuge" shall refer to centrifuges of the Adams type.

The dual member centrifuge of the Adams patent is particularly advantageous in that, as noted above, no seals are needed between the container of fluid being rotated and the non-moving component collection containers. The system of the Adams patent provides a way to process blood into components in a single, sealed, sterile system wherein whole blood from a donor can be infused into the centrifuge while the two members of the centrifuge are being rotated.

An alternate to the apparatus of the Adams patent is illustrated in U.S. Pat. No. 4,056,224 to Lolachi entitled "Flow System for Centrifugal Liquid Processing Apparatus." The system of the Lolachi patent includes a dual member centrifuge of the Adams type. The outer member of the Lolachi centrifuge is rotated by a single electric motor which is coupled to the internal rotatable housing by belts and shafts.

U.S. Pat. No. 4,108,353 to Brown entitled "Centrifugal Apparatus With Oppositely Positioned Rotational Support Means" discloses a centrifuge structure of the Adams type which includes two separate electrical motors. One electric motor is coupled by a belt to the outer member and rotates the outer member at a desired nominal rotational velocity. The second motor is carried within the rotating exterior member and rotates the inner member at the desired higher velocity, twice that of the exterior member.

U.S. Pat. No. 4,109,855 to Brown, et al., entitled "Drive System For Centrifugal Processing Apparatus" discloses yet another drive system. The system of the Brown, et al., patent has an outer shaft, affixed to the outer member for rotating the outer member at a selected velocity. An inner shaft, coaxial with the outer shaft, is coupled to the inner member. The inner shaft rotates the inner member at twice the rotational velocity as the outer member. A similar system is disclosed in U.S. Pat. No. 4,109,854 to Brown entitled "Centrifugal Apparatus With Outer Enclosure."

The continuous-flow systems described above are large and expensive units that are not intended to be portable. Further, they are also an order of magnitude more expensive than a standard, multi-container blood collection set. There exists the need, therefore, for a centrifugal system for processing blood and other biological fluids that is compact and easy to use and that does not have the disadvantages of prior-art continuous-flow systems.

Whole blood that is to be separated into its components is commonly collected into a flexible plastic donor bag, and the blood is centrifuged to separate it into its components through a batch process. This is done by spinning the blood bag for a period of about 10 minutes in a large refrigerated centrifuge. The main blood constituents, i.e., red blood cells, platelets and white cells, and plasma, having sedimented and formed distinct layers, are then expressed sequentially by a manual extractor in multiple satellite bags attached to the primary bag.

More recently, automated extractors have been introduced in order to facilitate the manipulation. Nevertheless, the whole process remains laborious and requires the separation to occur within a certain time frame to guarantee the quality of the blood components. This complicates the logistics, especially considering that most blood donations are performed in decentralized locations where no batch processing capabilities exist.

This method has been practiced since the widespread use of the disposable plastic bags for collecting blood in the 1970's and has not evolved significantly since then. Some attempts have been made to apply haemapheresis technology in whole blood donation. This technique consists of drawing and extracting on-line one or more blood components while a donation is performed, and returning the remaining constituents to the donor. However, the complexity and costs of haemapheresis systems preclude their use by transfusion centers for routine whole blood collection.

There have been various proposals for portable, disposable, centrifugal apparatus, usually with collapsible bags, for example as in U.S. Pat. Nos. 3,737,096, or 4,303,193 to Latham, Jr., or with a rigid walled bowl as in U.S. Pat. No. 4,889,524 to Fell, et al. These devices all have a minimum fixed holding volume which requires a minimum volume usually of about 250 ml to be processed before any components can be collected.

U.S. Pat. No. 5,316,540 to McMannis, et al., discloses a centrifugal processing apparatus, wherein the processing chamber is a flexible processing bag which can be deformed to fill it with biological fluid or empty it by means of a membrane which forms part of the drive unit. The bag comprises a single inlet/outlet tubing for the introduction and removal of fluids to the bag, and consequently cannot be used in a continual, on-line process. Moreover, the processing bag has a the disadvantage of having 650 milliliter capacity, which makes the McMannis, et al., device difficult to use as a blood processing device.

As discussed above, centrifuges are often used to separate blood into its components for use in a variety of therapeutic regimens. One such application is the preparation of a bioadhesive sealant. Bioadhesive sealants, also referred to as fibrin glues, are a relatively new technological advance which attempt to duplicate the biological process of the final stage of blood coagulation. Clinical reports document the utility of fibrin glue in a variety of surgical fields, such as, cardiovascular, thoracic, transplantation, head and neck, oral, gastrointestinal, orthopedic, neurosurgical, and plastic surgery. At the time of surgery, the two primary components comprising the fibrin glue, fibrinogen and thrombin, are mixed together to form a clot. The clot is applied to the appropriate site, where it adheres to the necessary tissues, bone, or nerve within seconds, but is then slowly reabsorbed by the body in approximately 10 days by fibrinolysis. Important features of fibrin glue is its ability to: (1) achieve haemostasis at vascular anastomoses particularly in areas which are difficult to approach with sutures or where suture placement presents excessive risk; (2) control bleeding from needle holes or arterial tears which cannot be controlled by suturing alone; and (3) obtain haemostasis in heparinized patients or those with coagulopathy. See, Borst, H. G., et al., *J Thorac. Cardiovasc. Surg.*, 84:548–553 (1982); Walterbusch, G. J., et al., *Thorac. Cardiovasc. Surg.*, 30:234–235 (1982); and Wolner, F. J., et al., *Thorac. Cardiovasc. Surg.*, 30:236–237 (1982).

Despite the effectiveness and successful use of fibrin glue by medical practitioners in Europe, neither fibrin glue nor its essential components fibrinogen and thrombin are widely used in the United States. In large part, this stems from the 1978 U.S. Food and Drug Administration ban on the sale of commercially prepared fibrinogen concentrate made from pooled donors because of the risk of transmission of viral infection, in particular the hepatitis-causing viruses such as HBV and HCV (also known as non-A and non-B hepatitis virus). In addition, the more recent appearance of other lipid-enveloped viruses such as HIV, associated with AIDS, cytomegalovirus (CMV), as well as Epstein-Barr virus and the herpes simplex viruses in fibrinogen preparations makes it unlikely that there will be a change in this policy in the foreseeable future. For similar reasons, human thrombin is also not currently authorized for human use in the United States. Bovine thrombin, which is licensed for human use in the United States, is obtained from bovine sources which do not appear to carry significant risks for HIV and hepatitis, although other bovine pathogens, such as bovine spongiform and encephalitis, may be present.

There have been a variety of methods developed for preparing fibrin glue. For example, Rose, et al. in U.S. Pat. No. 4,627,879 discloses a method of preparing a cryoprecipitated suspension containing fibrinogen and Factor XIII useful as a precursor in the preparation of a fibrin glue which involves (a) freezing fresh frozen plasma from a single donor such as a human or other animal, e.g. a cow, sheep or pig, which has been screened for blood transmitted diseases, e.g. one or more of syphilis, hepatitis or acquired immune deficiency syndrome, at about 80° C. for at least about 6 hours, preferably for at least about 12 hours; (b) raising the temperature of the frozen plasma, e.g. to between about 0° C. and room temperature, so as to form a supernatant and a cryoprecipitated suspension containing fibrinogen and Factor XIII; and (c) recovering the cryoprecipitated suspension. The fibrin glue is then prepared by applying a defined volume of the cyroprecipitate suspension described above and applying a composition containing a sufficient amount of thrombin, e.g. human, bovine, ovine or porcine thrombin, to the site so as to cause the fibrinogen in the suspension to be converted to the fibrin glue which then solidifies in the form of a gel.

A second technique for preparing fibrin glue is disclosed by Marx in his U.S. Pat. No. 5,607,694. Essentially, a cryoprecipitate as discussed previously serves as the source of the fibrinogen component and then Marx adds thrombin and liposomes. A third method discussed by Berruyer, M., et al., (*J. Thorac. Cardiovasc. Surg.*, 105(5):892–897 (1992)) discloses a fibrin glue prepared by mixing bovine thrombin not only with human coagulant proteins, such as fibrinogen, fibronectin, Factor XIII, and plasminogen, but also with bovine aprotinin and calcium chloride.

The above patents by Rose, et al., and Marx, and the technical paper by Berruyer, et al. each disclose methods for preparing fibrin sealants; however, each of these methods suffer disadvantages associated with the use of bovine thrombin as the activating agent. A serious and life threatening consequence associated with the use of fibrin glues comprising bovine thrombin is that patients have been reported to have a bleeding diathesis after receiving topical bovine thrombin. This complication occurs when patients develop antibodies to the bovine factor V in the relatively impure bovine thrombin preparations. These antibodies cross-react with human factor V, thereby causing a factor V deficiency that can be sufficiently severe to induce bleeding and even death. See, Rapaport, S. I., et al., *Am. J. Clin. Pathol.*, 97:84–91 (1992); Berruyer, M., et al., *J. Thorac. Cardiovasc. Surg.*, 105:892–897 (1993); Zehnder, J., et al., *Blood*, 76(10):2011–2016 (1990); Muntean, W., et al., *Acta Paediatr.*, 83:84–7 (1994); Christine, R. J., et al, *Surgery*, 127:708–710 (1997).

A further disadvantage associated with the methods disclosed by Marx and Rose, et al. is that the cryoprecipitate preparations require a large amount of time and monetary commitment to prepare. Furthermore, great care must be taken to assure the absence of any viral contaminants.

A further disadvantage associated with the methods previously disclosed is that while human thrombin is contemplated for use as an activator, human thrombin is not available for clinical use and there is no evidence that patients will not have an antigenic response to human thrombin. By analogy, recombinant human factor VIII has been shown to produce antigenic responses in hemophiliacs. See, Biasi, R. de., *Thrombosis and Haemostasis*, 71(5): 544–547 (1994). Consequently, until more clinical studies are performed on the effect of human recombinant thrombin one cannot merely assume that the use of recombinant human thrombin would obviate the antigenic problems associated with bovine thrombin. A second difficulty with thrombin is that it is autocatalytic, that is, it tends to self-destruct, making handling and prolonged storage a problem.

Finally, as discussed above, fibrin glue is comprised primarily of fibrinogen and thrombin thus lacking an appreciable quantity of platelets. Platelets contain growth factors and healing factors which are assumed to be more prevalent in a platelet concentrate. Moreover, platelets aid in acceleration of the clotting process.

There is still a need, therefore, for a centrifugal system for processing blood and other biological fluids, that is compact and easy to use and that does not have the disadvantages of prior-art continuous-flow systems and furthermore there exists a need for a convenient and practical method for preparing a platelet gel composition wherein the resulting platelet gel poses a zero risk of disease transmission and a zero risk of causing an adverse physiological reaction.

There is also a widespread need for a system that, during blood collection, will automatically separate the different components of whole blood that are differentiable in density and size, with a simple, low cost, disposable unit.

There is further a need for a centrifugal cell processing system wherein multiple batches of cells can be simultaneously and efficiently processed without the use of rotational coupling elements.

There is yet a further need for a platelet concentrate that aids in increasing the rate of fibrin clot formation, thereby facilitating haemostasis.

Preferably the apparatus will be essentially self-contained. Preferably, the equipment needed to practice the method will be relatively inexpensive and the blood contacting set will be disposable each time the whole blood has been separated.

SUMMARY OF THE INVENTION

Accordingly, one aspect of this invention provides a method and apparatus for the separation of components suspended or dissolved in a fluid medium by centrifugation. More specifically, one object of this invention is to provide a method for the separation and isolation of one or more whole blood components, such as platelet rich plasma, white blood cells and platelet poor plasma, from anticoagulated whole blood by centrifugation, wherein the components are isolated while the centrifuge is rotating.

Another aspect of this invention is to utilize the isolated cell components in a therapeutic regimen.

Another aspect of this invention provides an apparatus for the separation of whole blood components, wherein the apparatus contains a centrifuge bag that provides for simultaneous addition of whole blood from a source container and the withdrawal of a specific blood component during centrifugation.

Another aspect of this invention provides disposable, single-use centrifuge bags for holding whole blood during the separation of components of the whole blood by centrifugation, wherein the bag is adapted for use in a portable, point-of-use centrifuge.

Another aspect of this invention provides a portable centrifuge containing a disposable centrifuge bag that maximizes the amount of a predetermined blood fraction that can be harvested from an aliquot of blood that is of greater volume than the capacity of the disposable centrifuge bag.

More specifically, one embodiment of this invention comprises a flexible, disposable centrifuge bag adapted to be rotated about an axis, comprising:

a) one or more tubes, and b) upper and lower flexible sheets, each sheet having a doughnut shaped configuration, an inner perimeter defining a central core and an outer perimeter, wherein the upper and lower sheets are superimposed and completely sealed together at their outer perimeters, and wherein the tubes are sandwiched between the upper and lower sheets and extend from the central core toward the outer perimeter, such that when the upper and lower sheets are sealed at the inner perimeter the tubes are sealed between the upper and lower sheets at the inner perimeter and are in fluid communication with the environment inside and outside the centrifuge bag. The one or more tubes are fluidly connected to an umbilical cable comprising one or more lumen equal to the number of tubes of the centrifuge bag.

Yet another embodiment of the present invention comprises a rigid molded container adapted to be rotated about an axis, comprising a rigid, annular body having an axial core that is closed at the top end and opened at the bottom end. The rigid molded container further comprises an interior collection chamber for receiving and holding a fluid medium to be centrifuged, the chamber having an outer perimeter, an inner perimeter, and a generally off-centered "figure eight" shaped cross-sectional area. The rigid molded container further comprises a first channel which extends radially from the core and is in fluid communication with a point near the outer perimeter of the chamber, and a second channel which extends radially from the core and is in fluid communication with an area near the narrow portion or "neck" of the figure eight-shaped chamber. The first and second channels thus provide fluid communication with the environment inside and outside the interior collection chamber. The first and second channels are fluidly connected to a dual lumen tubing having an inlet lumen and an outlet lumen.

Yet another embodiment of the present invention is an apparatus and method for separating components contained in a fluid medium. More particularly, the present invention utilizes the principles of centrifugation to allow for the separation of whole blood into fractions such as platelet rich plasma and platelet poor plasma. In one aspect of the present invention, the above-described separation of the components is provided by utilizing a rotatable centrifuge motor comprising a base having a central column and a disposable centrifuge bag having a central core and which is positionable within the centrifuge motor and rotatable therewith. The disposable centrifuge bag, which holds the whole blood during centrifugation, further comprises an inlet tube for introducing the whole blood to the centrifuge bag, and an outlet tube for removing the desired blood fraction from the centrifuge bag. The inlet and outlet tubes are in fluid communication with a dual lumen tubing. The centrifuge bag is removably fixed within the centrifuge rotor by inserting the raised column through the bag center core and securing with the cover. During the rotation of the centrifuge, components of the whole blood will assume a radial, horizontal position within the centrifuge bag based upon a density of such components, and thus the fluid medium components will be separated from other components having different densities.

Once a desired degree of separation of whole blood has been achieved, the present invention provides for the specific removal of the desired fraction within one or more of the regions from the centrifuge bag through the outlet tube during continued rotation of the centrifuge, thereby allowing for on-line removal of the desired fraction. Additional aliquots may be added to the centrifuge bag via the inlet tube simultaneously or after the desired component has been harvested. In one embodiment, the centrifuge bag is a flexible, transparent, generally flat doughnut-shaped bag. In another embodiment, the centrifuge bag is a rigid, transparent container having an interior chamber for receiving and holding the fluid medium during centrifugation, the interior chamber having a generally off-centered figure eight cross-sectional configuration.

Another aspect of the present invention comprises a disposable centrifuge bag having an inlet tube and an outlet tube, wherein the outlet tube is fluidly connected with a bent fitting.

Another aspect of the present invention comprises a centrifuge rotor for holding a centrifuge bag, the rotor comprising a base and a cover, the base further having a first grooved, raised center column and the cover having a second grooved, raised center column. The centrifuge bag is a flexible, doughnut-shaped bag comprising inlet and outlet tubes in fluid communication with the environment inside and outside the centrifuge bag, wherein the tubes are seated in the base and cover column grooves to hold the centrifuge bag in a fixed position relative to the base and cover, such that the bag does not spin independently of the base and cover but rather spins concurrently and at the same rate of rotation as the base and cover.

Another aspect of the present invention comprises a centrifuge rotor for holding a centrifuge bag, the rotor comprising a base and a cover for securing a centrifuge bag therebetween, the centrifuge cover further comprising one or more concentric indicator circles that are spaced from the center of the cover or the base to aid the operator in visualizing the distal ends of these tubes.

Another aspect of the present invention for the separation of components of a fluid medium (e.g., whole blood) utilizes a centrifuge rotor comprising an interior chamber having a complex configuration, wherein the chamber holds a flexible, doughnut-shaped centrifuge bag for retaining the fluid medium during centrifugation. The centrifuge rotor is defined by a base having a lower chamber, and a cover having an upper chamber. When the cover is superimposed on the base, the upper and lower chambers define the annular interior chamber of the rotor. The interior rotor chamber has a generally off-centered figure eight-shaped cross-sectional configuration specifically designed to maximize the collection of the desired component (e.g., platelet rich plasma) by centrifugation of a fluid medium (e.g., anticoagulated whole blood). The centrifuge bag is formed from a substantially flexible material, such that the profile of the centrifuge bag during centrifugation is thus determined at least in part by the volume of the fluid medium contained therein. When the centrifuge bag is filled to maximum capacity, it assumes the configuration of the interior of the rotor chamber.

Another aspect of this invention comprises a method for on-line harvesting of a predetermined component of a fluid medium. One embodiment of the present invention utilizes a centrifuge and a disposable centrifuge bag for containing the fluid medium during separation and which is positionable within the centrifuge, the centrifuge bag further comprising at least one inlet tube and at least one outlet tube. The centrifuge includes a centrifuge rotor having a base portion, a cover, and an outer rim. The base portion and the cover define the interior of the centrifuge rotor, which is separated into upper and lower chambers. The disposable centrifuge bag is positionable horizontally within the lower chamber and may be appropriately secured to the centrifuge base by the cover. The centrifuge bag is fluidly connected via a dual lumen tubing to a source (e.g., to a container comprising anticoagulated autologous whole blood) and collection container (e.g., for receiving platelet rich plasma or some other component that will then be further processed). The dual lumen tubing comprises an inlet lumen fluidly connected to the inlet tube of the centrifuge bag and an outlet lumen fluidly connected to the outlet tube of the centrifuge bag. The centrifuge bag is substantially annular relative to the rotational axis of the centrifuge. When the centrifuge bag is positioned within the centrifuge rotor and appropriately secured thereto to allow for simultaneous rotation, the fluid medium may be provided to the centrifuge bag via the inlet lumen of the tubing during rotation of the centrifuge. The components of the bag assume radial, horizontal positions base based on their densities. When a desired degree of separation has been achieved, the desired fraction may be removed from the centrifuge bag via the outlet lumen during continued rotation of the centrifuge. The position of the fraction to be harvested may be shifted into the area of the outlet tube as needed, either by withdrawing components that are positioned near the outer perimeter through the inlet tube, or by adding additional aliquots of the fluid medium to the bag. In one embodiment of this method, the bag is a flexible, transparent doughnut-shaped bag. In another embodiment of this method, the bag is a rigid, transparent bag comprising an interior chamber having an off-centered, figure eight cross-sectional configuration.

This invention further provides a centrifugal liquid processing system that may be automated.

This invention further provides a centrifuge having an internal lead drive mechanism allowing for a compact size.

This invention further provides a method and device for the production and isolation of thrombin for all medical uses.

This invention further provides a method for preparing a completely autologous platelet gel.

This invention further provides an autologous platelet gel wherein the risks associated with the use of bovine and recombinant human thrombin are eliminated.

This invention further provides an autologous platelet gel for any application.

This invention further provides cellular components to be used in medical applications.

Additional advantages and novel features of this invention shall be set forth in part in the description and examples that follow, and in part will become apparent to those skilled in the art upon examination of the following or may be learned by the practice of the invention. The apects and the advantages of the invention may be further realized and attained by means of the instrumentalities and in combinations particularly pointed out in the appended claims.

BRIEF DESCRIPTION OF THE DRAWINGS

The accompanying drawings, which are incorporated in and form a part of the specifications, illustrate embodiments of the present invention, and together with the description serve to explain the principles of the invention.

In the Drawings:

FIG. 12 is an exploded, perspective view of the top bearing assembly of the centrifuge of FIG. 2.

FIG. 13 is a perspective view of the top case shell of the top bearing assembly of FIG. 12.

FIG. 25 is a top view of a flexible, disposable centrifuge bag of this invention.

FIG. 26 is a perspective view of a flexible, disposable centrifuge bag of this invention.

FIGS. 27, 28, 29, and 30 are illustrations of bent fittings of this invention having "T" shaped, "curved T" shaped, "L" shaped, and "J" shaped configurations, respectively.

FIG. 31 is an illustration of an inlet and/or outlet tube of this invention.

FIG. 43 is a side cross-sectional view of a rigid disposable centrifuge bag of this invention.

FIG. 44 is a schematic illustration of separated blood components contained in a centrifuge bag having an elliptical cross-sectional view of the centrifuge bag shown in FIG. 43.

FIG. 45 is a side cross-sectional view of a rigid disposable centrifuge bag of this invention.

FIG. 46 is a schematic illustration of the surface areas and various dimensions of the figure eight configuration as shown in FIG. 45.

FIG. 47 is a schematic illustration of separated blood components contained in a centrifuge bag having a figure eight side cross-sectional configuration.

DETAILED DESCRIPTION OF THE PREFERRED EMBODIMENT

Figure 1:
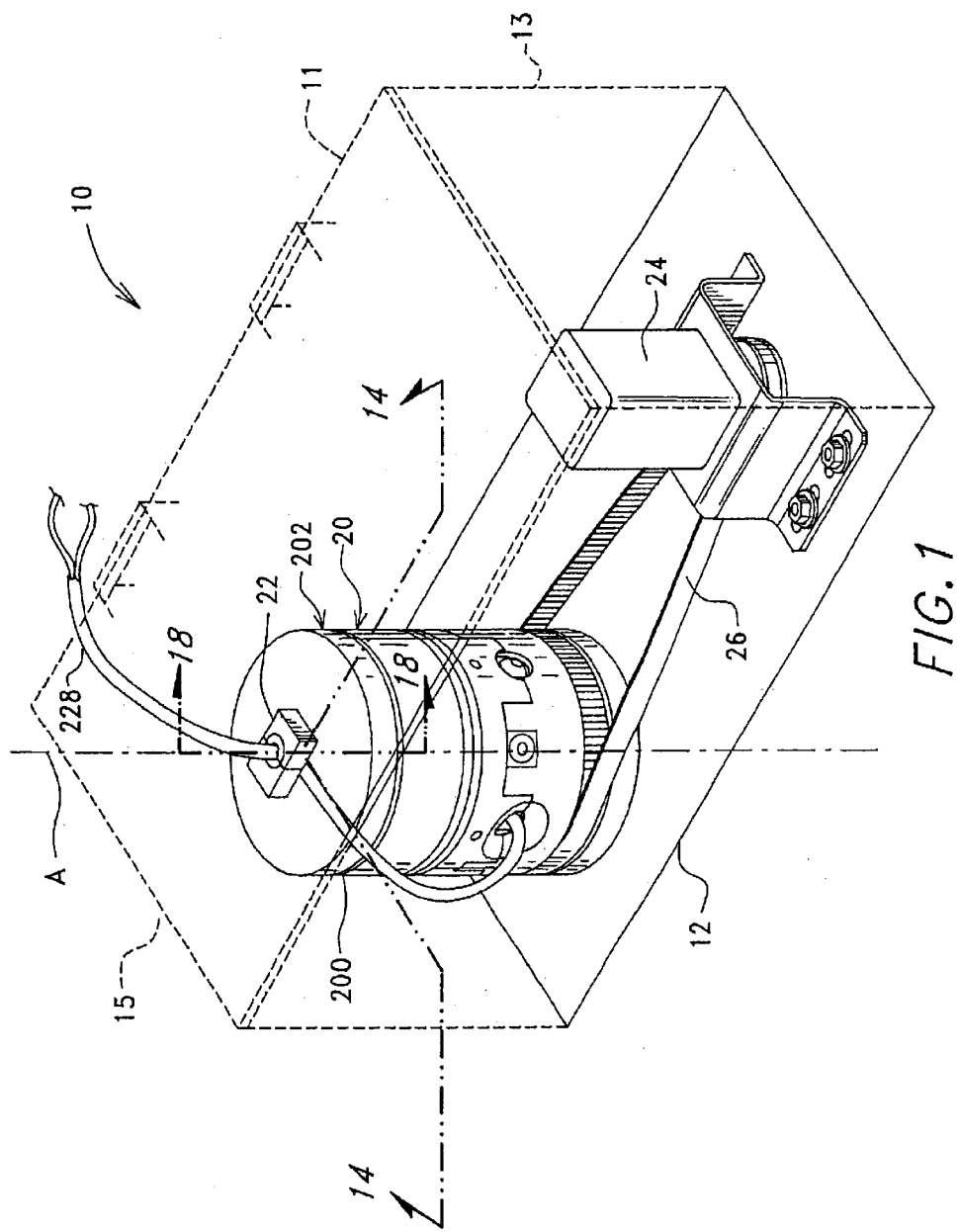
FIG. 1 is a perspective view illustrating one embodiment of the continuous-flow centrifugal processing system of the present invention illustrating a centrifuge and side-mounted motor positioned within a protective housing or enclosure of the invention.

The centrifugal processing system 10 of the present invention is best shown in FIG. 1 having a stationary base 12, a centrifuge 20 rotatably mounted to the stationary base 12 for rotation about a predetermined axis A, a rotor 202 for receiving a disposable bag (not shown) designed for continuous-flow. As illustrated, the centrifugal processing system 10 includes a protective enclosure 11 comprising the main table plate or stationary base 12, side walls 13, and a removable lid 15 made of clear or opaque plastic or other suitable materials to provide structural support for components of the centrifugal processing system 10, to provide safety by enclosing moving parts, and to provide a portable centrifugal processing system 10. The centrifugal processing system 10 further includes a clamp 22 mounted over an opening (not shown) in the lid 15. Clamp 22 secures at a point at or proximately to axis A without pinching off the flow of fluid that travels through umbilical cable 228. A side mounted motor 24 is provided and connected to the centrifuge 20 by way of a drive belt 26 for rotating the drive shaft assembly 28 (see FIG. 2) and the interconnected and driven rotor assembly 200 in the same rotational direction with a speed ratio selected to control binding of umbilical cable 228 during operation of the system, such as a speed ratio of 2:1 (i.e., the rotor assembly 200 rotates twice for each rotation of the drive shaft assembly 28). The present invention is further directed toward a dispensing device 902, best shown in FIG. 60 for the withdrawal and manipulation of specific blood components for various therapeutic regimens, such as but not limited to the production of platelet rich plasma, platelet poor plasma, and white blood cells which may be used for the production of autologous thrombin and autologous platelet gels.

Figure 2:
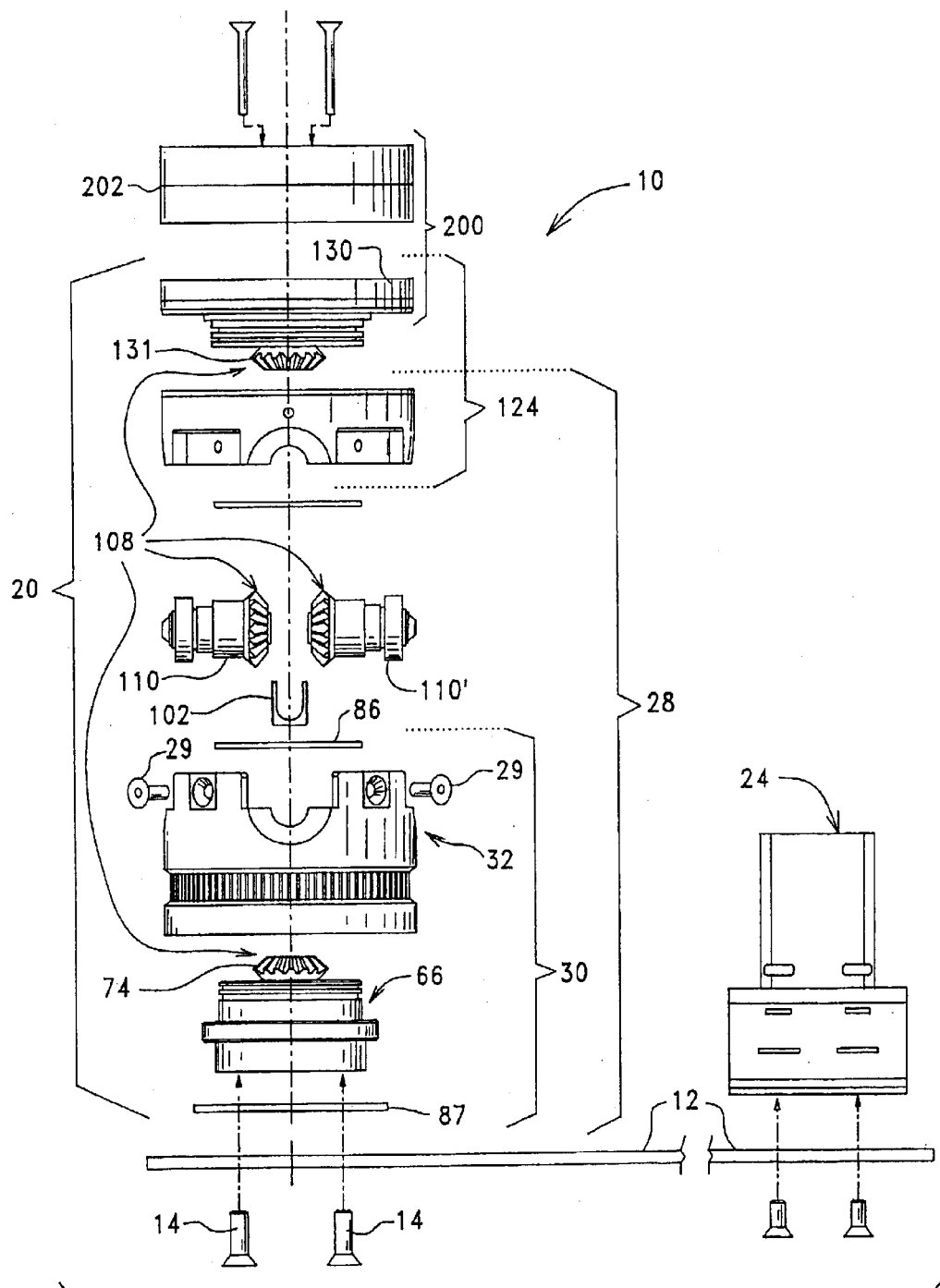
FIG. 2 is an exploded side view of the centrifuge and the side-mounted motor of the centrifugal processing system of FIG. 1 illustrating the individual components of the centrifuge.

Referring now to FIG. 2, the continuous-flow centrifugal processing system 10 comprises a centrifuge 20 to which a rotor 202 is removably or non-removably attached. The design of centrifuge 20 and its self-contained mid-shaft gear assembly 108 (comprised of gears 110, 110', 131, and 74) is a key component of the invention thereby allowing for the compact size of the entire centrifugal processing system 10 and providing for a desired speed ratio between the drive shaft assembly 28 and the rotor assembly 200.

The centrifuge 20 is assembled, as best seen in FIG. 2, by inserting the lower bearing assembly 66 into lower case shell 32 thus resulting in lower case assembly 30. Cable guide 102 and gears 110 and 110' are then positioned within lower case assembly 30, as will be discussed in more detail below, so that gears 110 and 110' are moveably of engaged with lower bearing assembly 66. Upper bearing assembly 130 is then inserted within top case shell 126 thus resulting in bearing assembly 124 which is then mated to lower case assembly 30, such that gears 110 and 110' are also moveably engaged with upper bearing assembly 130, and held in place by fasteners 29. Lower bearing assembly 66 is journaled to stationary base or main table plate 12 by screws 14, thus allowing centrifuge 20 to rotate along an axis A, perpendicular to main table plate 12 (as shown in FIG. 1).

Figure 3:
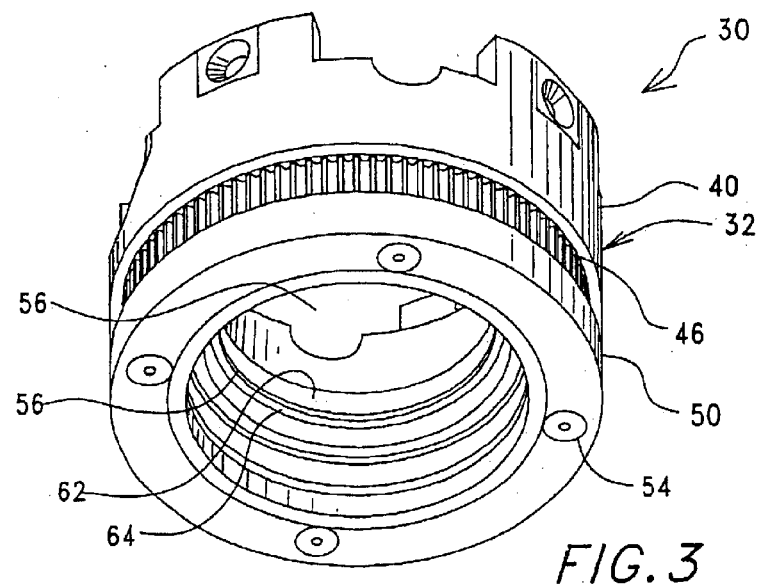
FIG. 3 is a partial perspective view of the lower case assembly of the drive shaft assembly of FIG. 2.
Figure 4:
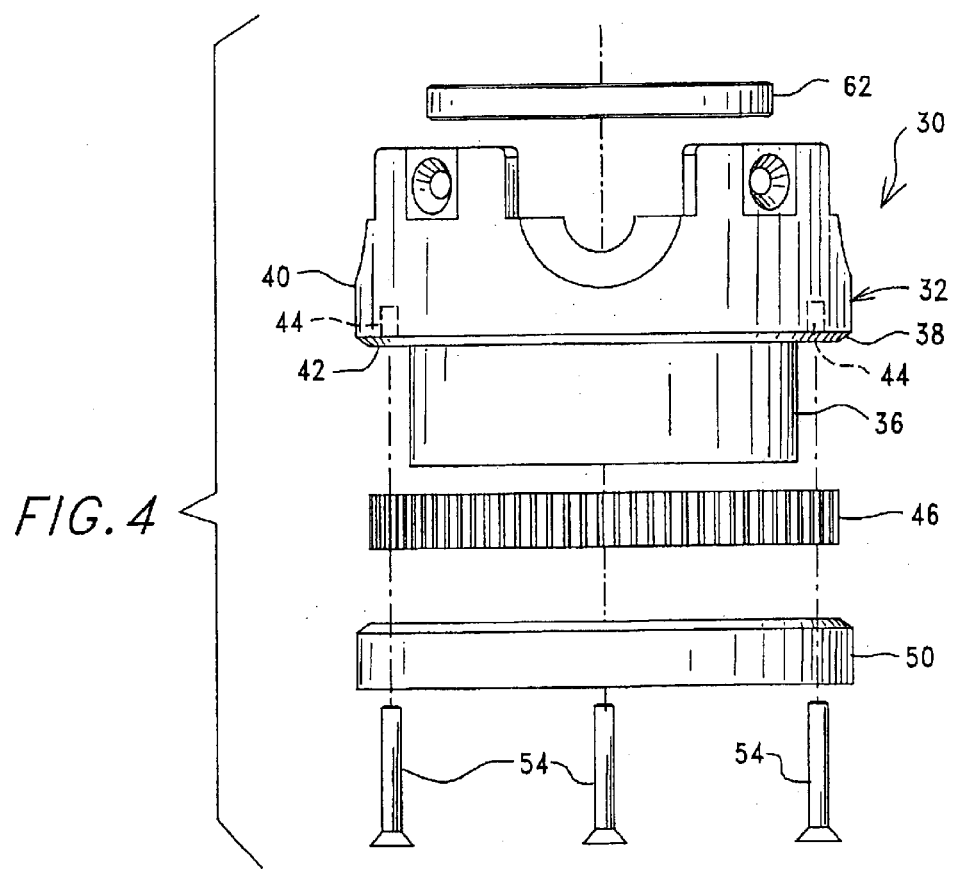
FIG. 4 is an exploded side view of the lower case assembly of FIG. 3.
Figure 5:
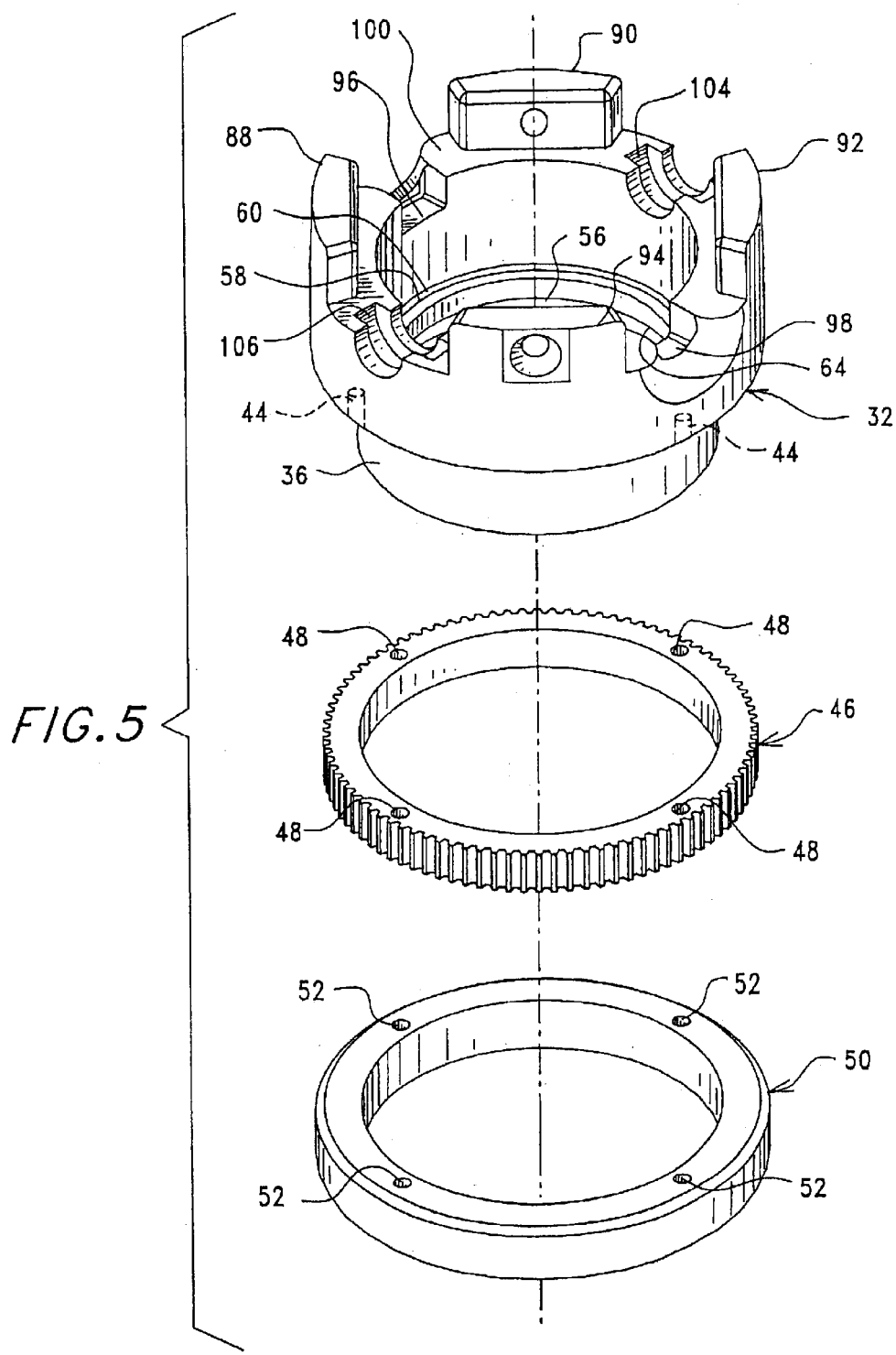
FIG. 5 is an exploded perspective view of the components of the lower case assembly of FIG. 3.

Referring now to FIGS. 3, 4, and 5, the lower case assembly 30 is preferably, but not necessarily, machined or molded from a metal material and includes a lower case shell 32, timing belt ring 46, timing belt flange 50, and bearing 62 (e.g., ball bearings and the like). Lower case shell 32 includes an elongated main body 40 with a smaller diameter neck portion 36 extending from one end of the main body 40 for receiving timing belt ring 46 and timing belt flange 50.

Figure 6:
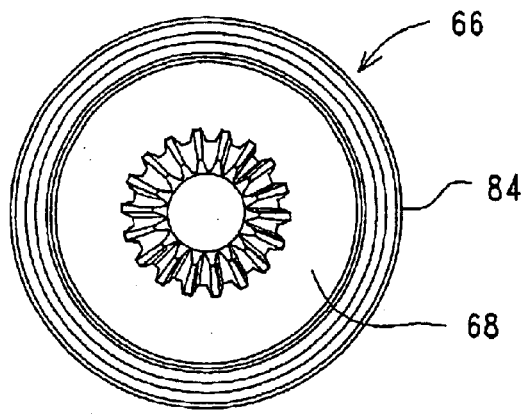
FIG. 6 is a top view of the lower bearing assembly which is positioned within the lower case assembly of FIG. 3.
Figure 7:
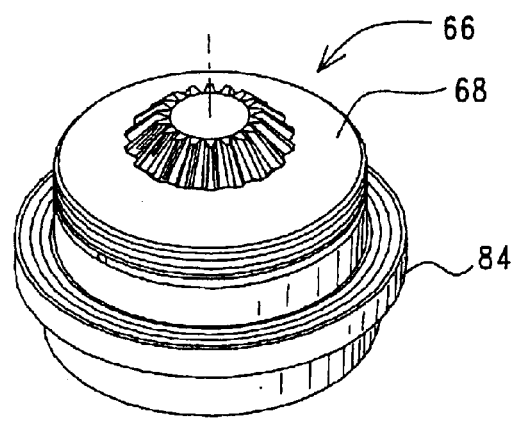
FIG. 7 is a perspective view of the lower bearing assembly of FIG. 6.
Figure 8:
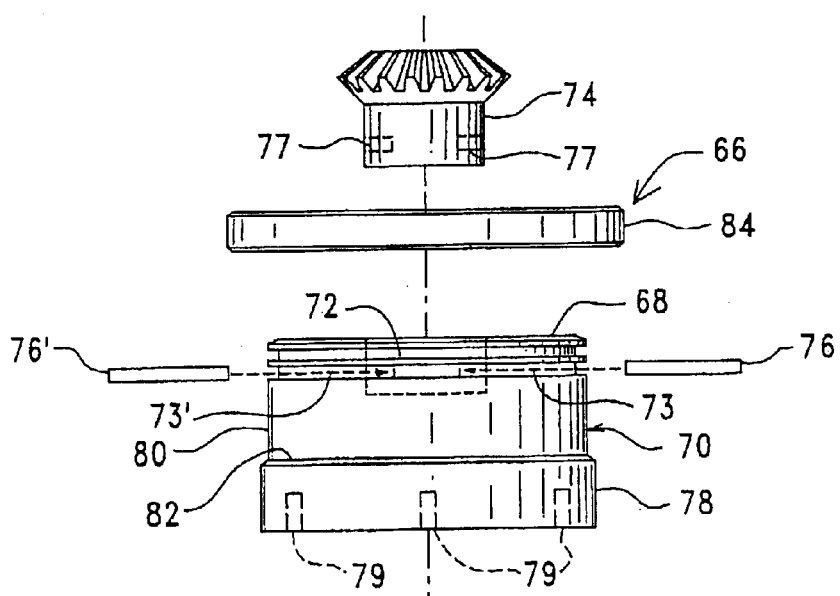
FIG. 8 is an exploded side view of the lower bearing assembly of FIGS. 6 and 7.

The larger diameter main body 40 terminates into the neck portion 36 thereby forming an external shoulder 38 having a bearing surface 42 for timing belt ring 46. Timing belt ring 46 and timing belt flange 50, as best seen in FIG. 5, have inner diameters that are slightly larger than the outer diameter of neck portion 36 allowing both to fit over neck portion 36. Shoulder 38 further contains at least one and preferably four internally thread holes 44 that align with hole guides 48 and 52 in timing belt ring 46 and timing belt flange 50, respectively (shown in FIG. 5). Consequently, when assembled, screws 54 are received by hole guides 52 and 48 and are threaded into thread holes 44 thus securing timing belt 46 and timing belt flange 50 onto neck portion 36. Lower case shell 32 also has an axial or sleeve bore 56 extending there through, and an internal shoulder 58, the upper surface 60 of which is in approximately the same horizontal plane as external shoulder 38. Bearing 62 (shown in FIG. 4) is press fit concentrically into sleeve bore 56 so that it sits flush with upper surface 60. Internal shoulder 58 also has a lower weight bearing surface 64 which seats on the upper surface 68 of lower bearing assembly 66, shown in FIGS. 6–8.

Lower bearing assembly 66 comprises a lower gear insert 70, ball bearings 84, gear 74 and spring pins 76 and 76'. As will become clear, the gear 74 may be of any suitable gear design for transferring an input rotation rate to a mating or contacting gear, such as the gears 110, 110' of the mid-shaft gear assembly 108, with a size and tooth number selected to provide a desired gear train or speed ratio when combined with contacting gears. For example, the gear 74 may be configured as a straight or spiral bevel gear, a helical gear, a worm gear, a hypoid gear, and the like out of any suitable material. In a preferred embodiment, the gear 74 is a spiral gear to provide a smooth tooth action at the operational speeds of the centrifugal processing system 10. The upper surface 68 of lower gear insert 70 comprises an axially positioned sleeve 72, which receives and holds gear 74, gear 74 is preferably retained within sleeve 72 by the use of at least one and preferably two spring pins 76 and 76' which are positioned within spring pinholes 73 and 73' extending horizontally through lower gear insert 70 into sleeve 72. Thus, when gear 74 having spring pin receptacles 77 and 77' is inserted into sleeve 72 the spring pins 76 and 76' enter the corresponding receptacles 77 and 77' thus holding the gear 74 in place. Of course, other assembly techniques may be used to position and retain gear 74 within the lower gear assembly 66 and such techniques are considered within the breadth of this disclosure. For example, gear 74 may be held in sleeve 72 by a number of other methods, such as, but not limited to being press fit or frictionally fit, or alternatively gear 74 and lower gear insert 70 may be molded from a unitary body.

The base 78 of lower gear insert 70 has a slightly larger diameter than upper body 80 of lower gear insert 70 as a result of a slight flare. This slight flare produces shoulder 82 upon which ball bearing 84 is seated. Once assembled lower bearing assembly 66 is received by sleeve bore 56 extending through neck portion 36 of lower case shell 32. A retaining ring 86 is then inserted into the annular space produced by the difference of the outer diameter of the lower bearing assembly 66 and the inner diameter of sleeve bore 56 above ball bearings 84. A second retaining ring 87 (shown in FIG. 2) is also inserted into the annular space produced by the difference between the outer diameter of the lower bearing assembly 66 and the inner diameter of sleeve bore 56 below ball bearing 84, thereby securing lower gear insert 70 within lower case shell 32. Consequently, ball bearings 62 and 84 are secured by retaining rings 86 and 87, respectively, resulting in lower case shell 32 being journaled for rotation about lower bearing assembly 66 but fixed against longitudinal and transverse movement thereon. Therefore, when assembled lower bearing assembly 66 is mounted to stationary base 12, by securing screws 14 into threaded holes 79 located in the base 78. Lower case shell 32 is thus able to freely rotate about stationary lower bearing assembly 66 when the drive belt 26 is engaged.

Figure 9:
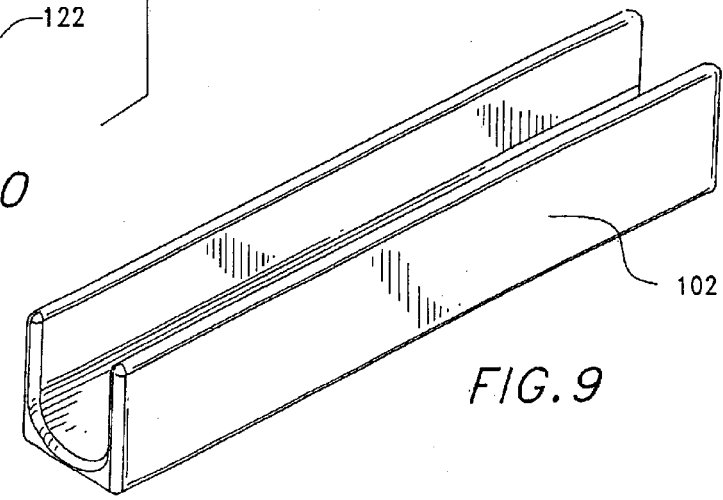
FIG. 9 is a perspective view of the receiving tube guide of the centrifuge of FIG. 2.

Referring now to FIG. 5, extending from the opposite end of neck portion 36 on lower case shell 32 are a number of protrusions or fingers 88, 90, 92, and 94. Positioned between protrusions 88 and 90, and between protrusions 92 and 94 are recessed slots 96 and 98, respectively, for receiving tube guide 102 (FIG. 9). The function of tube guide 102 will be discussed in further detail below, but in short it guides umbilical cable 228 connected to centrifuge bag 226 through the mid-shaft gear assembly 108 and out of the centrifuge 20.

Figure 14:
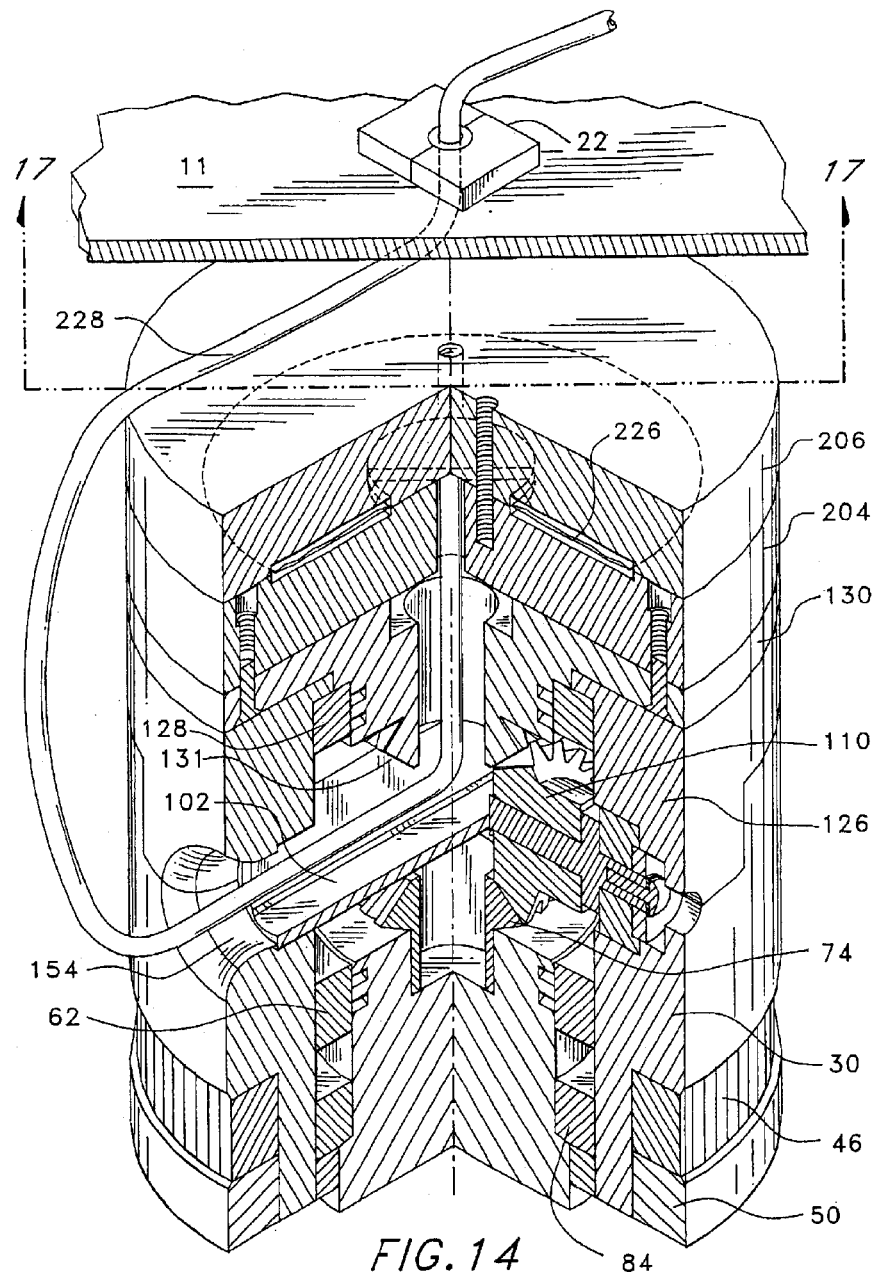
FIG. 14 is a perspective view of the centrifuge of the present invention shown in FIG. 1, having a quarter section cut away along lines 14—14 of FIG. 1.

Positioned between protrusions 90 and 92, and between protrusions 88 and 94 are recessed slots 104 and 106, respectively, for receiving gears 110 and 110' of mid-shaft gear assembly 108 (FIG. 2). The gears 110 and 110' are preferably configured to provide mating contact with the gear 74 and to produce a desired, overall gear train ratio within the centrifuge 20. In this regard, the gears 110 and 110' are preferably selected to have a similar configuration (e.g., size, tooth number, and the like) as the gear 74, such as a spiral gear design. As illustrated in FIGS. 2 and 14 mid-shaft gear assembly 108 comprises a pair of gears 110 and 110' engaged with gears 74 and 131. While the construction of gears and gear combinations is well known to one skilled in the mechanical arts, a brief description is disclosed briefly herein.

Figures 10, 11:
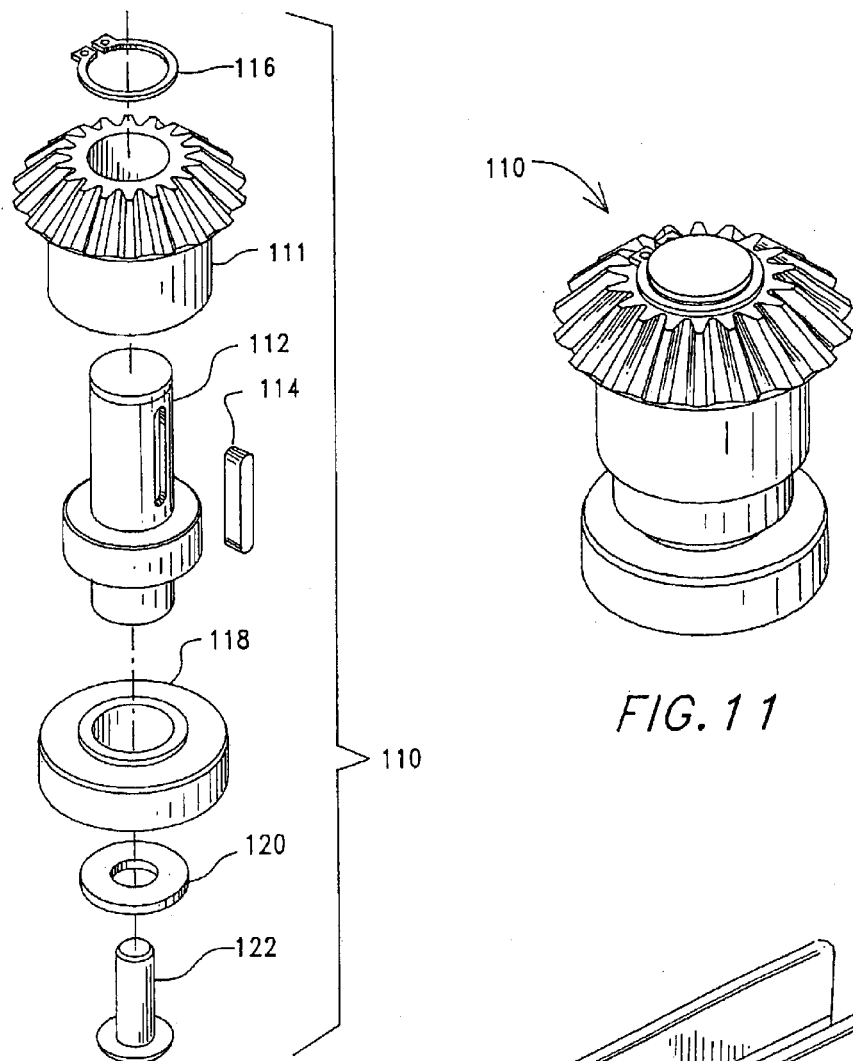
FIG. 10 is an exploded, perspective view of a gear of the mid-shaft gear assembly of FIG. 2.
FIG. 11 is a perspective view of the gear of FIG. 10 as it appears assembled.

FIG. 10 illustrates an exploded view depicting the assembly of gear 110, and FIG. 11 is a perspective view of the gear 110 of FIG. 10 as it appears assembled. Gear 110' is constructed in the same manner. Gear 111 is locked onto mid-gear shaft 112 using key stock 114 and external retaining ring 116. Ball bearing 118 is then attached to mid gear shaft 112 using a flat washer 120 and cap screw 122. Recessed slots 104 and 106 of lower case shell 32 then receive ball bearing 118 and 118' (not shown). In an alternate embodiment ball bearing 118 can be replaced by bushings (not shown). When assembled, gears 110 and 110' make contact with the lower gear 74 (see FIGS. 2 and 14) to provide contact surfaces for transferring a force from the stationary gear 74 to the gears 110 and 110' to cause the gears 110 and 110' to rotate at a predetermined rate that creates a desired output rotation rate for the driven rotor assembly 200. The rotor assembly 200 is driven by the drive shaft assembly 28 which is rotated by the drive motor 24 at an input rotation rate or speed, and in a preferred embodiment, the drive shaft assembly 28 through the use of the gears 110 and 110' is configured to rotate the rotor assembly 200 at an output rotation rate that is twice the input rotation rate (i.e., the ratio of the output rotation rate to the input rotation rate is 2:1). This ratio is achieved in the illustrated embodiment by locking the gears 110 and 110' located within the drive shaft assembly 28 to rotate about the centrifuge center axis, A, with the lower case shell 32 which is rotated by the drive motor 24. The gears 110 and 110' also contact the stationary gear 74 which forces the gears 110, 110' to rotate about their rotation axes which are traverse to the centrifuge center axis, A, and as illustrated, the rotation axes of the gears 110, 110' coincide. By rotating with the lower case shell 32 and rotating about the gear rotation axes, the gears 110, 110' are able to provide the desired input to output rotation rate of 2:1 to the rotor assembly 200.

In this regard, gears 110 and 110' and tube guide 102 are locked into position by attaching top bearing assembly 124 to lower case assembly 30. Top bearing assembly 124 (as shown in FIG. 12) comprises top case shell 126, ball bearing 128, and an upper bearing 130. Top case shell 126, as best seen in FIGS. 12 and 13, comprises an upper surface 132, a lower lip 134 and a central or axial bore 136 there through. Upper surface 132 slightly overhangs axial bore 136 resulting in a shoulder 138 having a lower surface 140 (shown in FIG. 13). Lower lip 134 is a reverse image of upper lip 100 on lower case shell 32 (shown in FIG. 5).

Upper bearing assembly 130 (FIG. 12) comprises an upper surface 133 and a lower surface 135 wherein the upper surface 133 has a means for receiving a rotor 202. On the lower surface 135 a concentrically positioned column 137 protrudes radially outward perpendicular to lower surface 135. Upper bearing assembly 130 further comprises an axially positioned bore 139 that traverses column 137 and upper surface 133 and receives upper gear insert 131. Upper gear insert 131 also contains an axial bore 142 and thus when positioned concentrically within column 137 axial bores 139 and 142 allow for umbilical cable 228 to travel through upper bearing assembly 130 of top case shell 126 down to cable guide 102 (shown in FIG. 14). As discussed previously with respect to lower bearing assembly 66, upper gear insert 131 may be any suitable gear design for receiving an input rotation rate from a mating or contacting gear, such as the gears 110, 110' of the mid-shaft gear assembly 108, with a size and tooth number selected to provide a desired gear train or speed ratio when combined with contacting gears. For example, gear insert 131 may be configured as a straight or spiral bevel gear, a helical gear, a worm gear, a hypoid gear, and the like. In a preferred embodiment, gear 131 is a spiral gear to provide a smooth tooth action at the operational speeds of the centrifugal processing system 10. Gear insert 131 is preferably retained within column 137 by use of at least one and preferably two spring pins (not shown); however, other assembly techniques may be used to position and retain the gear insert 131 within the column 137 and such techniques are considered within the breadth of this disclosure. For example, gear insert 131 may be held in column 137 by a number of other methods, such as, but not limited to being press fit or frictionally fit or alternatively gear insert 131 and the upper bearing assembly may be molded from a unitary body.

Upper bearing assembly 130 is then inserted into axial bore 136 of top case shell 126 so that the lower surface 135 sits flush with upper surface 132 of top case shell 126. Ball bearing 128 is then inserted into the annular space created between the outer diameter of column 137 and the inner side wall 141 of top case shell 126 thereby securing upper bearing assembly 130 into place.

Referring now to FIG. 13, lower lip 134 is contoured to mate with protrusions 88, 90, 92 and 94 extending from lower case shell 32. Specifically, the outer diameter of lower lip 134 matches the outer diameter of the upper end of main body 40 of lower case shell 32 and recesses 144 and 148 receive and retain protrusions 88 and 92 respectively, while recesses 146 and 150 receive and retain protrusions 94 and 88, respectively. Holes are placed through each recess and each protrusion so that when assembled, fasteners 152 (shown in FIG. 12) can be inserted through the holes thereby fastening the top bearing assembly 124 to the lower case assembly 30.

Positioned between recesses 144 and 146 and between recesses 148 and 150 are recessed slots 104' and 106', respectively, for receiving gears 110 and 110' of mid-shaft gear assembly 108 (FIGS. 2 and 14). The gears 110 and 110' are preferably configured to provide mating contact with the gear insert 131 and to produce a desired, overall gear train ratio within the centrifuge 20. In this regard, the gears 110 and 110' are preferably selected to have a similar configuration (e.g., size, tooth number, and the like) as the gear 131, such as a spiral gear design. Furthermore recessed slots 96' and 98' exist between recesses 144 and 150 and between recesses 146 and 148, respectively. When gears 110 and 110' are assembled as shown in FIG. 14, recessed slots 96 and 96' from the lower case shell 32 and top case shell 126, respectively, form port 154, and recessed slots 98 and 98' form port 156 thereby allowing the umbilical cable 228 to exit centrifuge 20 through either port 154 or 156. Described above is one method of assembling the centrifugal processing system 10 of the present invention; however, those skilled in the art will appreciate that the lower case assembly 30 and upper bearing assembly can be joined in number of ways that allow the four gears to be properly aligned with respect to one another.

In the above manner, the centrifugal processing system 10 provides a compact, portable device useful for separating blood and other fluids in an effective manner without binding or kinking fluid feed lines, cables, and the like entering and exiting the centrifuge 20. The compactness of the centrifugal processing system 10 is furthered by the use of the entirely contained and interior gear train described above that comprises, at least in part, gear 74, gears 110 and 110', and gear insert 131 of the upper bearing 130. The gear insert 131 of the upper bearing 130 is preferably selected to provide a contact surface(s) with the gears 110 and 110' that transfers the rotation rate of the gears 110 and 110' and consequently from gear 74 and to the gear insert 131 of the upper bearing 130. In one preferred embodiment, the gear insert 131 of the upper bearing 130 is a spiral gear rigidly mounted within the upper bearing 130 to rotate the rotor assembly 200 and having a design similar to that of the spiral gear 74, i.e., same or similar face advance, circular pitch, spiral angle, and the like. During operation, the gear 74 remains stationary as the lower case shell 32 is rotated about the centrifuge axis, A, at an input rotation rate, such as a rotation rate chosen from the range of 0 rpm to 5000 rpm. The gears 110, 110' are rotated both about the centrifuge axis, A, with the shell 32 and by contact with the stationary gear 74. The spiral gears 110, 110' contact the gear insert 131 of the upper bearing 130 causing the gear insert 131 and connected upper bearing 130 to rotate at an output rotation rate that differs, i.e., is higher, than the input rotation rate.

Although a number of gear ratios or train ratios (i.e., input rotation rate/output rotation rate) may be utilized to practice the invention, one embodiment of the invention provides for a gear train ratio of 1:2, where the combination and configuration of the gear 74, gears 110, 110', and gear 131 of the upper bearing 130 are selected to achieve this gear train ratio. Uniquely, the rotation of the gears 110, 110' positively affects the achieved gear train ratio to allow, in one embodiment, the use of four similarly designed gears which lowers manufacturing costs while achieving the increase from input to output rotation speeds. Similarly, as will be understood by those skilled in the mechanical arts, numerous combinations of gears in differing number, size, and configuration that provides this ratio (or other selected ratios) may be utilized to practice the invention and such combinations are considered part of this disclosure. For example, although two gears 110, 110' are shown in the mid-shaft gear assembly 108 to distribute transmission forces and provide balance within the operating centrifuge, more (or less) gears may be used to transmit the rotation of gear 74 to the gear of the upper bearing 130. Also, just as the number, size, and configuration of the internal gears may be varied from the exemplary illustration of FIGS. 1–14, the material used to fabricate the gear 74, the gears 110, 110', and the gear insert 131 may be any suitable gear material known in the art.

Another feature of the illustrated centrifugal processing system 10 that advantageously contributes to compactness is the side-mounted drive motor 24. As illustrated in FIGS. 1 and 2, the drive motor 24 is mounted on the stationary base 12 of the enclosure 11 adjacent the centrifuge 20. The drive motor 24 may be selected from a number of motors, such as a standard electric motor, useful for developing a desired rotation rate in the centrifuge 20 of the centrifugal processing system 10. The drive motor 24 may be manually operated or, as in a preferred embodiment, a motor controller may be provided that can be automatically operated by a controller of the centrifugal processing system 10 to govern operation of the drive motor 24 (as will be discussed in detail with reference to the automated embodiment of the invention). As illustrated in FIG. 1, a drive belt 26 may be used to rotate the drive shaft assembly 28 (and, therefore, the rotor assembly 200). In this embodiment, the drive belt 26 preferably has internal teeth (although teeth are not required to utilize a drive belt) selected to mate with the external teeth of the timing belt ring 46 of the lower case assembly 30 portion of the drive shaft assembly 28. The invention is not limited to the use of a drive belt 26, which may be replaced with a drive chain, an external gear driven by the motor 24, and any other suitable drive mechanisms. When operated at a particular rotation rate, the drive motor 24 rotates the drive shaft assembly 28 at nearly the same rotation rate (i.e., the input rotation rate). A single speed drive motor 24 may be utilized or in some embodiments, a multi and/or variable speed motor 24 may be provided to provide a range of input rotation rates that may be selected by the operator or by a controller to obtain a desired output rotation rate (i.e., a rotation rate for the rotor assembly 200 and included centrifuge bag 226.

The present invention generally includes an apparatus and methods for the separation of a predetermined fraction(s) from a fluid medium utilizing the principles of centrifugation. Although the principles of the present invention may be utilized in a plurality of applications, one embodiment of this invention comprises isolating predetermined fraction(s) (e.g., platelet rich plasma or platelet poor plasma) from anticoagulated whole blood. The platelet rich plasma may be used, for example, in the preparation of platelet concentrate or gel, and more particularly may be used to prepare autologous platelet gel during surgery using blood drawn from the patient before or during surgery.

Figure 17:
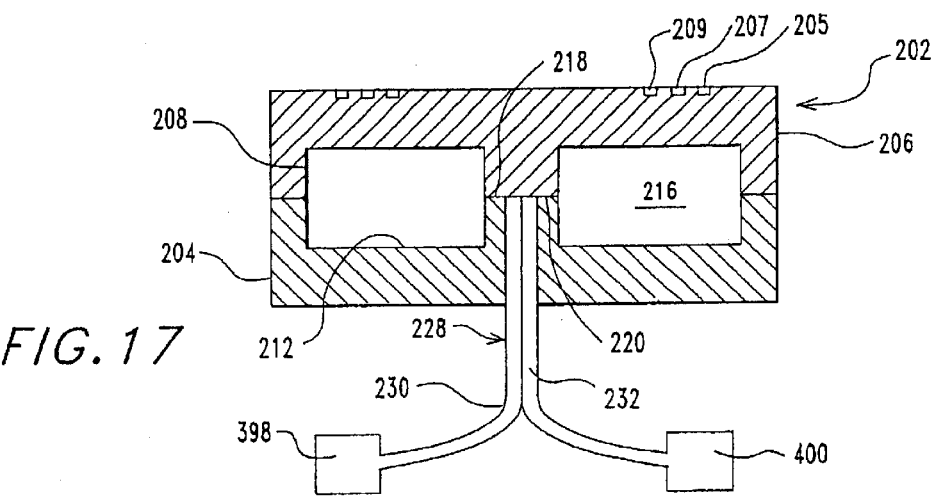
FIG. 17 is a side cross-sectional view of one embodiment of a rotor of this invention taken along view lines 17 of FIG. 1 for holding a disposable centrifuge bag, showing a dual lumen tubing connected to the bag.
Figure 18:
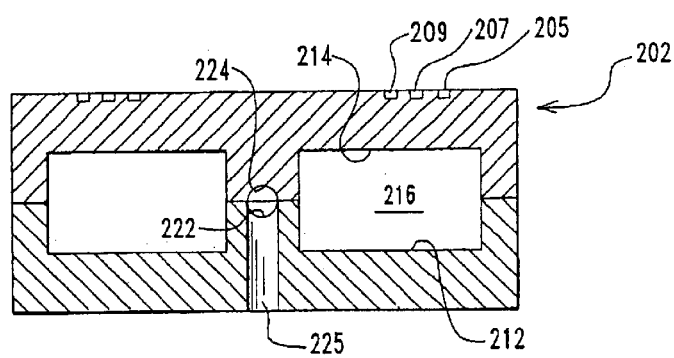
FIG. 18 is a side cross-sectional view of one embodiment of a rotor of this invention taken along view lines 18 of FIG. 1 for holding a disposable centrifuge bag, showing the grooved columns of the base and cover.

The centrifuge 20 has been discussed above and demonstrates the compact and portable aspects of the present invention. To complete the device of the present invention a fluid collection device, also referred to as a bowl or rotor 202 is attached to the upper surface 133 of the upper bearing assembly 130 as shown in FIGS. 1 and 2. Rotor 202 is preferably mounted permanently to upper bearing assembly 130, however, rotor 202 may also be capable of being removed. Rotor 202 comprises a rotor base 204 (shown in FIG. 15) having a lower annular groove 212, and a rotor cover 206 having an upper annular groove 214. As shown in FIGS. 17 and 18 the annular interior chamber 216 of rotor 202 is defined by upper and lower annular grooves 212 and 214. The lower annular 212 receives a centrifuge bag 226 for containing the fluid medium to be centrifuged. Centrifuge bag 226 is connected to supply and receiving containers 398, 400, respectively, via umbilical cable 228 which is preferably, but not limited to a dual lumen. There may be instances where a certain technique requires multiple outlet or inlet ports and consequently umbilical cable 228 of the present invention may comprise multiple lumens. Umbilical cable 228 according to the preferred embodiment comprises inlet lumen 230 and outlet lumen 232 such that a fluid medium may be provided to and removed from the centrifuge bag 226 during rotation of the centrifuge rotor 202.

Figure 15:
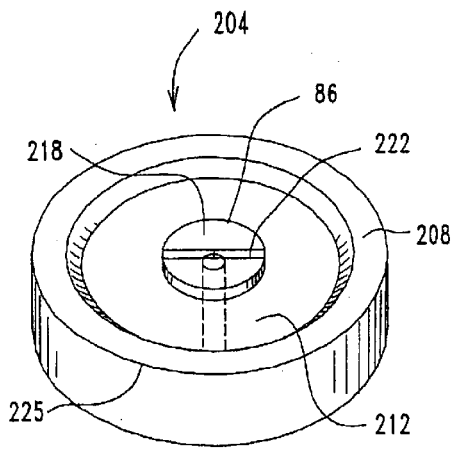
FIG. 15 is a perspective view of one embodiment of a centrifuge rotor base.
Figure 16:
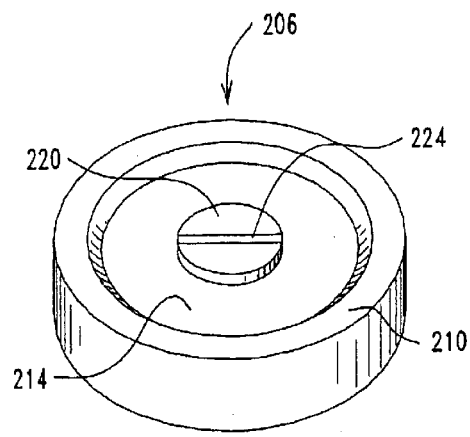
FIG. 16 is a perspective view of one embodiment of a centrifuge rotor cover.

One embodiment of centrifuge rotor 202 is more particularly illustrated in FIGS. 15, 16, 17 and 18. FIG. 15 is a perspective view of rotor base 204, and FIG. 16 is a perspective view of rotor cover 206. FIG. 17 is a cross-sectional side view of rotor 202 taken along view lines 17 in FIG. 1, and FIG. 18 is a cross-sectional side view of rotor 202 taken along view lines 18 in FIG. 1. As illustrated in FIG. 15, rotor base 204 comprises raised annular rim 208 and raised column 218 that is axially disposed in base 204. Raised column 218 further has a groove 222 extending across the diameter of column 218. Annular groove 212 is defined by raised annular rim 208 and raised column 218. The height of rim 208 is equal to the height of column 218. Rotor cover 206 shown in FIG. 16 comprises raised annular rim 210 and raised column 220 which is axially disposed in rotor cover 206. Raised column 220 further has a groove 224 extending across the diameter of column 220. Annular groove 214 is defined by rim 210 and column 220. The height of rim 210 is equal to the height of column 220.

Generally, when centrifuge rotor 202 is to be assembled for use, a flexible centrifuge bag such as a doughnut-shaped centrifuge bag 226 (FIGS. 19 and 20) having a center core 242 is placed in rotor base 204 such that center column 218 extends through the core 242 of centrifuge bag 226 and the centrifuge bag 226 lies in annular groove 212. Rotor cover 206 is superimposed on rotor base 204 such that grooves 222 and 224 are aligned, as illustrated in FIGS. 17 and 18. When rotor cover 204 is secured to rotor base 206 by appropriate screws, fasteners, or the like (not shown), rims 208 and 210 are in complete contact with each other such that annular groove 212 and annular groove 214 define rotor interior chamber 216. In one embodiment, columns 218 and 220 are in complete contact with each other. Alternatively, the inner perimeter 240 of centrifuge bag 226 is secured between columns 218 and 220 such that columns 218 and 220 do not completely physically contact each other.

With the above description of one embodiment of the centrifuge in mind, another preferred embodiment of a centrifuge for use in the centrifugal processing system 10 will be described. Referring to FIGS. 19–22, a preferred embodiment of a centrifuge 640 is illustrated that utilizes a uniquely arranged internal pulley system to obtain a desired input to output drive ratio (such as 2:1, as discussed above) rather than an internal gear assembly. The centrifuge 640 utilizes the side-mounted motor 24 (shown in FIG. 1) through drive belt 26 to obtain the desired rotation rate at the rotor portion of the centrifuge.

Figure 19:
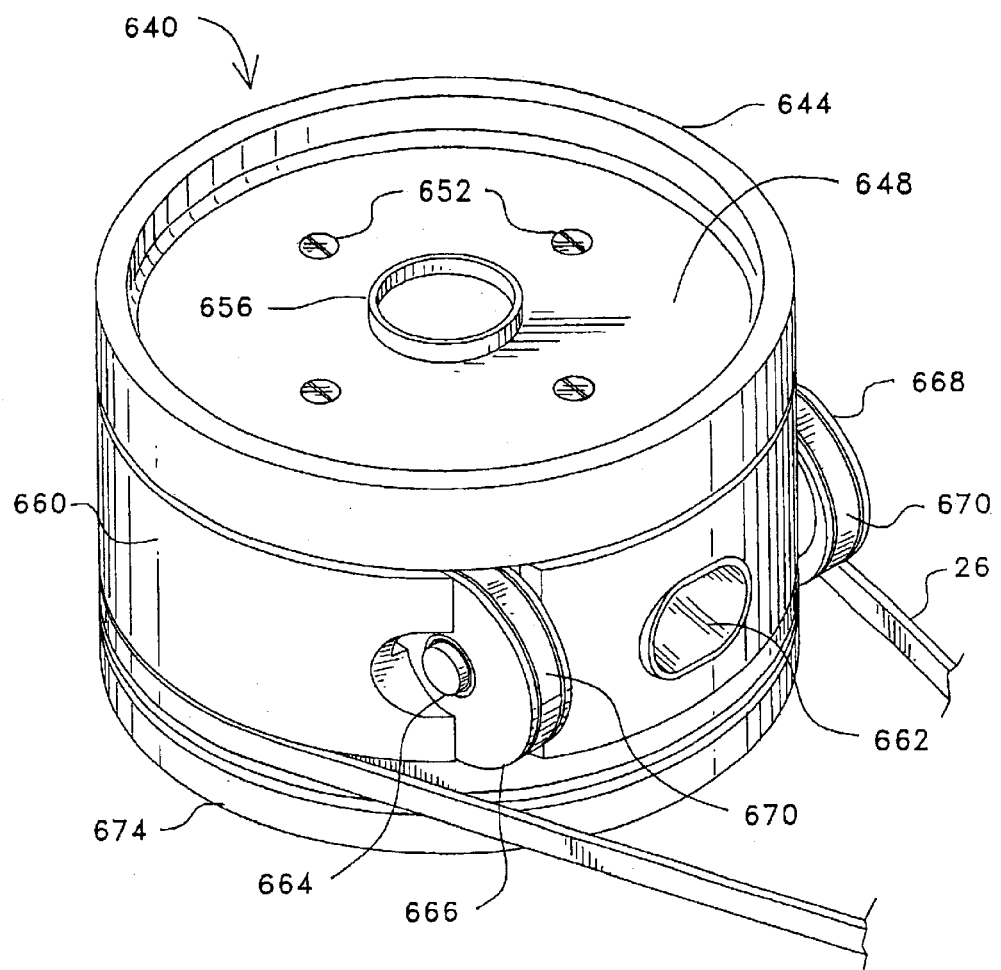
FIG. 19 is an enlarged perspective view similar to FIG. 1 illustrating an alternate embodiment of a centrifuge driven by a side-mounted motor (with only the external drive belt shown).

Referring first to FIG. 19, the centrifuge 640 includes a rotor base 644 (or top plate) with a recessed surface 648 for receiving and supporting a centrifuge bag during the operation of the centrifuge 640. The rotor base 644 is rigidly mounted with fasteners (e.g., pins, screws, and the like) to a separately rotable portion (i.e., a top pulley 698 discussed with reference to FIGS. 20 and 21) of a lower case shell 660. A cable port 656 is provided centrally in the rotor base 644 to provide a path for a centrifuge tube or umbilical cable that is to be fluidically connected to a centrifuge bag positioned on the recessed surface 648 of the rotor base 644. It is important during operation of the centrifuge 640 to minimize and control contact and binding of the umbilical cable and moving parts (such as drive belts and pulleys). In this regard, the lower case shell 660 includes a side cable port 662 for the umbilical cable to enter the centrifuge 640, which, significantly, the side cable port 662 is located between idler pulleys 666, 668 to provide a spacing between any inserted tube or cable and the moving drive components of the centrifuge 640.

Idler shaft or pins 664 are mounted and supported within the lower case shell 660 to allow the pins 664 to physically support the pulleys 666, 668. The idler pulleys 666, 668 are mounted on the pins 664 by bearings to freely rotate about the central axis of the pins 664 during operation of the centrifuge 640. The idler pulleys 666, 668 are included to facilitate translation of the drive or motive force provided or imparted by the drive belt 26 to the lower case shell 660 to the rotor base 644, as will be discussed in more detail with reference to FIGS. 20 and 21, and to physically support the internal drive belt 670 within the centrifuge 640. The drive belt 26 is driven by the side-mounted motor 24 (shown in FIG. 1) and contacts the lower case shell 660 to force the lower case shell 660 to rotate about its central axis. The lower case shell 660 is in turn mounted on the base 674 in a manner that allows the lower case shell 660 to freely rotate on the base 674 as the drive belt 26 is driven by the side-mounted motor 26. The base 674 is mounted to a stationary base 12 (shown in FIG. 1) such that the base 674 is substantially rigid and does not rotate with the lower case shell 660.

Figure 20:
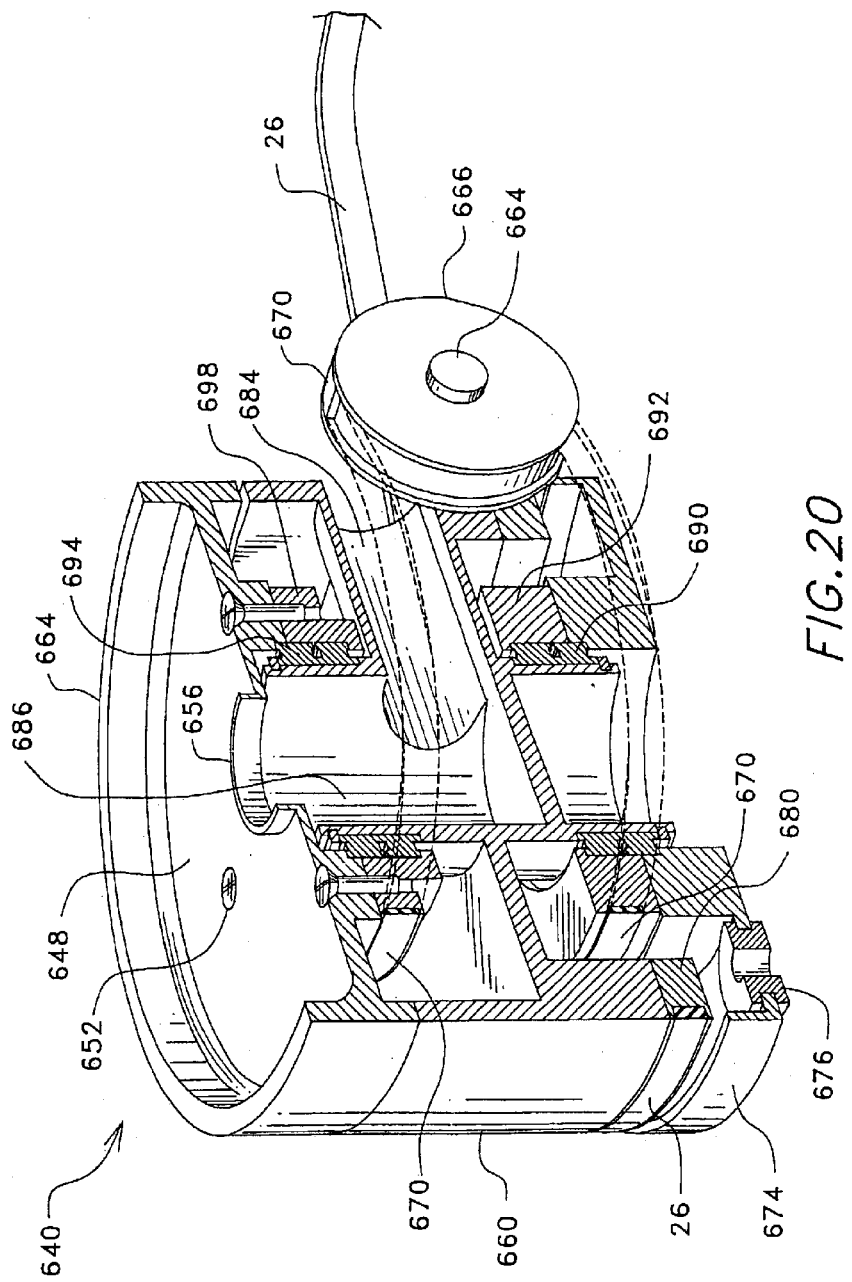
FIG. 20 is a cutaway side view of the centrifuge of FIG. 19 illustrating the internal pulley drive system utilized to achieve a desired drive ratio and illustrating the rotor base configured for receiving a centrifuge bag.
Figure 21:
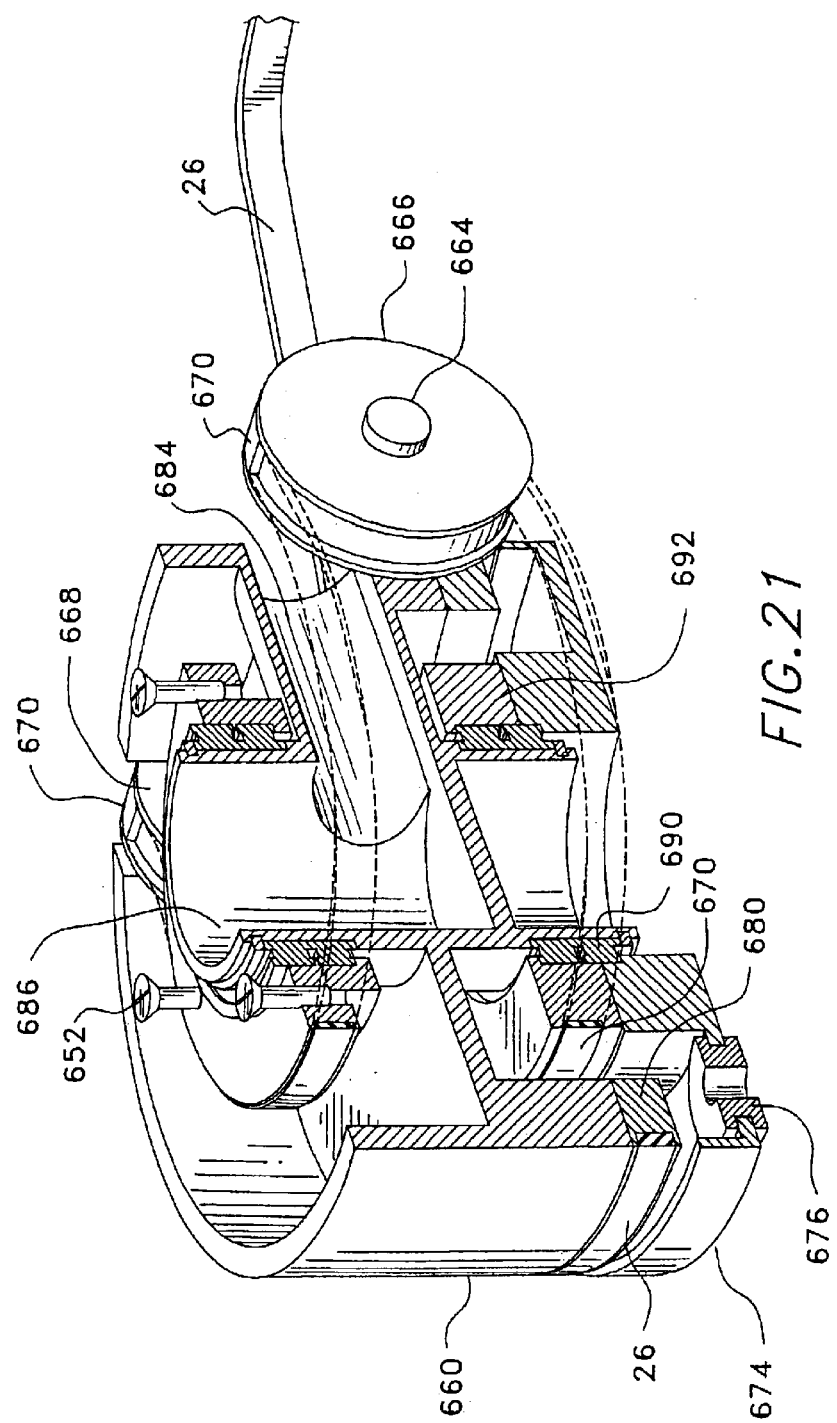
FIG. 21 is a cutaway side view similar to FIG. 20 with the rotor base removed to better illustrate the top pulley and the location of both idler pulleys relative to the installed internal drive belt.
Figure 22:
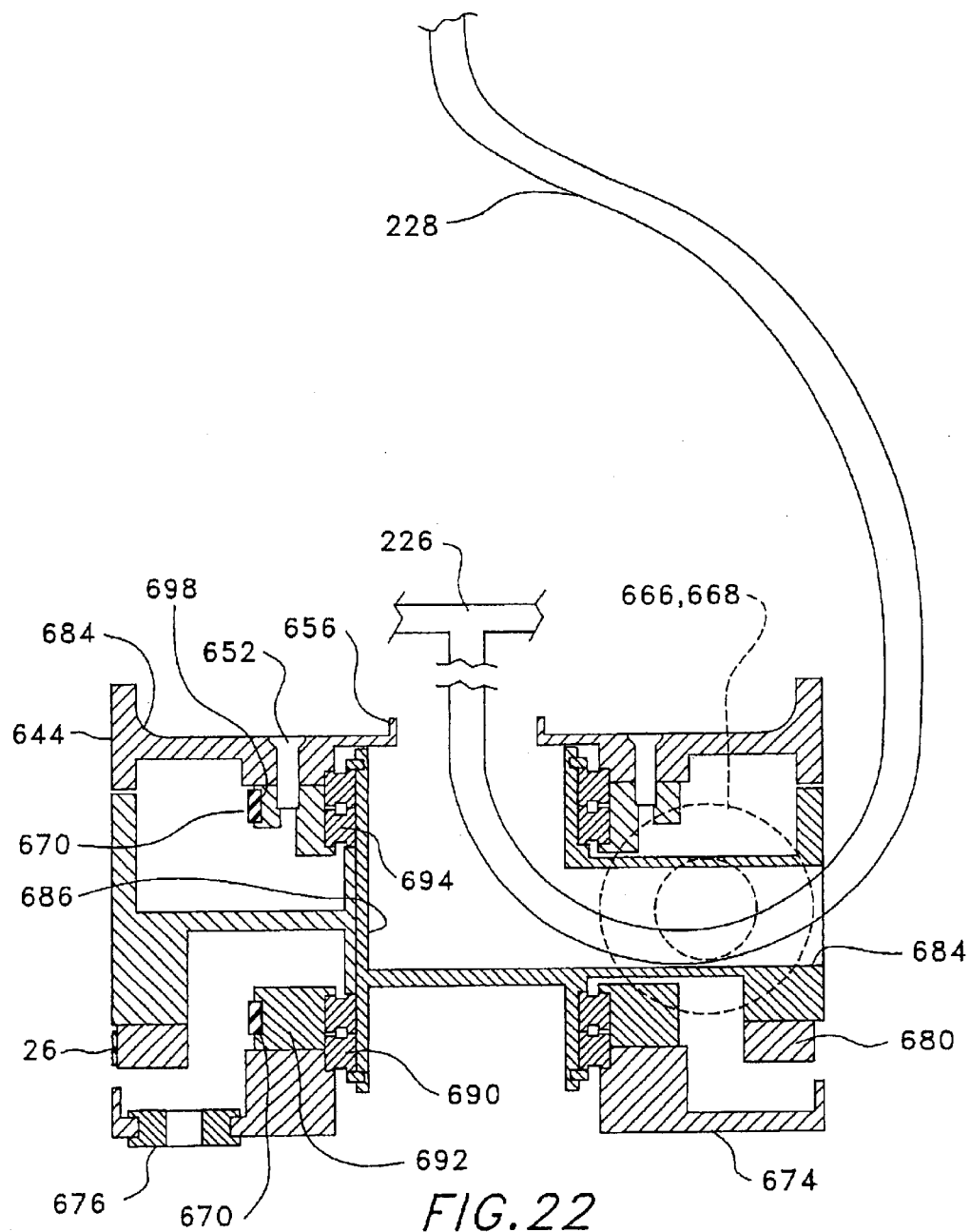
FIG. 22 is a sectional view of the centrifuge of FIG. 20 further illustrating the internal pulley drive system an showing the routing of the centrifuge tube (or umbilical cable).

Referring now to FIGS. 20-22, the centrifuge 640 is shown with a cutaway view to more readily facilitate the discussion of the use of the internal pulley assembly to obtain a desired output to input ratio, such as two to one. As shown, the base 674 includes vibration isolators 676 fabricated of a vibration absorbing material such as rubber, plastic, and the like through which the base 674 is mounted relatively rigidly to the stationary base 12 (of FIG. 1). The drive belt 26 from the side-mounted motor 24 (of FIG. 1) contacts (frictionally or with the use of teeth and the like as previously discussed) a drive pulley 680, which is rigidly mounted to the lower case shell 660. As the drive belt 26 is driven by the motor 24, the lower case shell 660 through drive pulley 680 rotates about its center axis (which corresponds to the center axis of the centrifuge 640). This rotation rate of the lower case shell 660 can be thought of as the input rotation rate or speed.

To obtain a desired, higher rotation rate at the rotor base 644, the lower case shell 660 is mounted on the base to freely rotate about the centrifuge center axis with bearings 690 that mate with the base 674. The bearings 690 are held in place between the bottom pulley 692 and the base 674, and the bottom pulley 692 is rigidly attached (with bolts or the like) to the base 674 to remain stationary while the lower case shell 660 rotates. The illustrated bearings 690 are two-piece bearings which allow the lower case shell 660 to rotate on the base 674. An internal drive belt 670 is provided and inserted through the lower case shell 660 to contact the outer surfaces of the bottom pulley 692. The belt 670 preferably is installed with an adequate tension to tightly mate with the bottom pulley 692 such that frictional forces cause the belt 670 to rotate around the stationary bottom pulley 692. This frictional mating can be enhanced using standard rubber belts or belts with teeth (and of course, other drive devices such as chains and the like may be substituted for the belt 670).

The internal drive belt 670 passes temporarily outside the centrifuge 640 to contact the outer surfaces of the idler pulleys 666 and 668. These pulleys 666, 668 do not impart further motion to the belt 670 but rotate freely on pins 664. The idler pulleys 666, 668 are included to allow the rotation about the centrifuge center axis by lower case shell 660 to be translated to another pulley (i.e., top pulley 698) that rotates about the same axis. To this end, the idler pulleys 666, 668 provide non-rigid (or rotable) support that assists in allowing the belt 670 to be twisted without binding and then fed back into an upper portion of the lower case assembly 660 (as shown clearly in FIGS. 20 and 21). As the internal drive belt 670 is fed into the lower case assembly 660, the belt 670 contacts the outer surfaces of a top pulley 698.

During operation of the centrifuge 640, the movement of the internal drive belt 670 causes the top pulley 698 to rotate about the centrifuge center axis. The idler pulleys 666 and 668 by the nature of their placement and orientation within the centrifuge 640 relative to the pulleys 692 and 698 cause the rotor base 644 to rotate in the same direction as the lower case shell 660. Significantly, the top pulley 698 rotated about the centrifuge center axis at twice the input rotation rate because it is mounted to the lower case shell 660 via bearings 694 (preferably, a two piece bearing similar to bearings 690 but other bearing configurations can be used) which are mounted to the center shaft 686 of the lower case shell 660 to frictionally contact an inner surface of the top pulley 698. Since the internal drive belt 670 is rotating about the bottom pulley 692 and the idler pulleys 666, 668 are rotating about the centrifuge central axis by drive belt 26, the top pulley 698 is turned about the centrifuge central axis in the same direction as the lower case shell 660 but at twice the rate.

In other words, the drive force of the drive belt 26 and the internal drive belt 670 are combined by the components of the centrifuge 640 to create the output rotation rate. While a number of output to input drive ratios may be utilized, as discussed previously, a 2:1 ratio is generally preferable, and the centrifuge 640 is preferably configured such that the second, faster rotation rate of the top pulley 698 is substantially twice that of the lower case shell 660. The use of an internal drive belt 670 in combination with two pulleys rotating about the same axis and the structural support for the pulleys within a rotating housing results in a centrifuge that is very compact and that operates effectively at a 2:1 drive ratio with relatively low noise levels (which is desirable in many medical settings).

The 2:1 drive ratio obtained in the top pulley 698 is in turn passed on to the rotor base 644 by rigidly attaching the rotor base 644 to the top pulley 698 with fasteners 652. Hence, a centrifuge bag placed on the recessed surface 648 of the rotor base 644 is rotated at a rate twice that of the umbilical cable 228 that is fed into lower case shell 660, which effectively controls binding as discussed above. The bearing 694 (one or more pieces) wrap around the entire center shaft 686 of the lower case shell 660. To provide a path for the umbilical cord 228 to pass through the centrifuge 640 to the rotor base 644 (which during operation will be enclosed with a rotor top or cover as shown in FIG. 1), the rotor base 644 includes the cable port 656 and the center shaft 686 is configured to be hollow to form a center cable guide. This allows an umbilical cable 228 to be fed basically parallel to the centrifuge center axis to the centrifuge bag (not shown). The lower case shell 660 includes the side cable port 662 to provide for initial access to the centrifuge 640 and also includes the side cable guide (or tunnel) 684 to guide the cable 228 through the lower case shell 660 to the hollow portion of the center shaft 686. The side port 662 and the side cable guide 684 are positioned substantially centrally between the two idler pulleys 666, 668 to position the cable 228 a distance away from the internal drive belt 670 to minimize potential binding and wear.

The centrifuge 640 illustrated in FIGS. 19–22 utilizes two-piece bearings for both the bottom and top pulleys 692 and 698, respectively, and to provide a path for the umbilical cable 228 a central "blind" pathway (via side cable guide 684, the hollow center of the center shaft 686, and cable ports 656, 662) was provided in the centrifuge 640. While effective, this "blind" pathway can in practice present binding problems as the relatively stiff cable 228 is fed or pushed through the pathway. To address this issue, an alternate centrifuge embodiment 700 is provided and illustrated in FIGS. 23 and 24. In this embodiment, the upper portions of the centrifuge 700 include a guide slot between the idler pulleys 666, 668 that enables an umbilical cable 228 to be fed into the centrifuge 700 from the top with the no components to block the view of the operator inserting the cable 228.

To allow a guide slot to be provided, the contiguous upper bearing 694 in the centrifuge 640 are replaced with bearing members that have at least one gap or separation that is at least slightly larger than the outer diameter of the cable 228. A number of bearing members may be utilized to provide this cable entry gap and are included in the breadth of this disclosure. As illustrated, the centrifuge 700 includes a rotor base 702 that is rigidly fastened with fasteners 704 to the top pulley 698 (not shown) to rotate with this pulley at the output rate (e.g., twice the input rate) and to receive and support a centrifuge bag on recessed surface 716. The rotor base 702 further includes the cable port 718 which is useful for aligning the center of the bag and cable 228 with the center of the centrifuge 700.

To allow ready insertion of the cable 228 in the centrifuge 700, the rotor base 702 further includes a cable guide slot 712 which as illustrated is a groove or opening in the rotor base 702 that allows the cable 228 to be inserted downward through the centrifuge 700 toward the side cable guide 724 of the lower case shell 720. The lower case shell 720 also includes a cable guide slot 722 cut through to the top of the side cable guide 724. Again, the guide slots 712 and 724 are both located in a portion of the centrifuge 700 that is between the idler pulleys 666, 668 to position an inserted cable 228 from contacting and binding with the internal drive belt 670, which basically wraps around 180 degrees of the top pulley or lower case shell 720.

Figure 23:
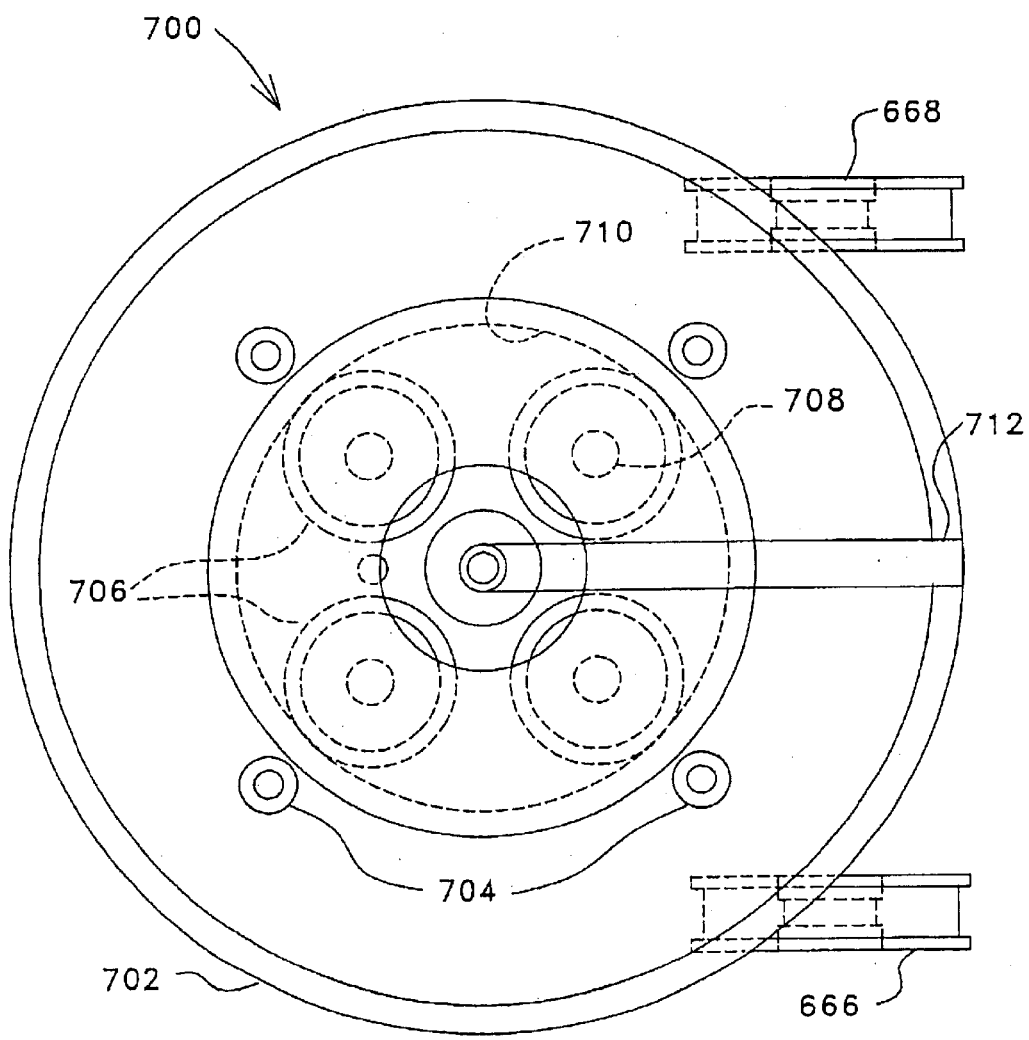
FIG. 23 is a top view of a further alternate centrifuge similar to the centrifuge of FIG. 19 but including internal, separate bearing members (illustrated as four cam followers) that allows the inclusion of guide shaft to be cut through portions of the centrifuge for positioning of the centrifuge tube (or umbilical cable).
Figure 24:
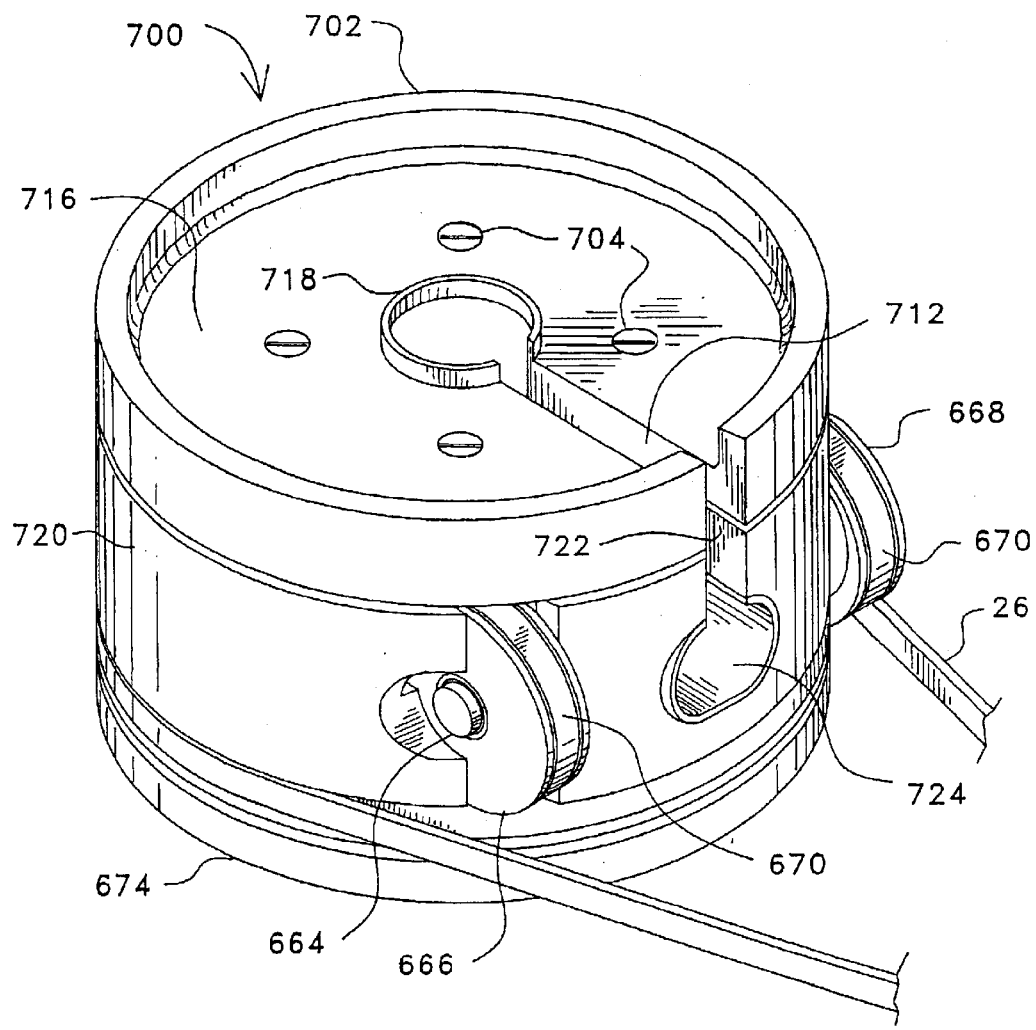
FIG. 24 is a perspective view similar to FIG. 19 illustrating the centrifuge embodiment of FIG. 23 further illustrating the guide slot and showing that the centrifuge can be driven by an external drive belt.

As shown in FIG. 23, the bearing members 706 are spaced apart and preferably, at least one of these spaces or gaps is large enough to pass through the cable 228 to the center shaft of the lower case shell 720. As illustrated, four cam followers are utilized for the bearing members 706, although a different number may be employed. The cam followers 706 are connected to the top pulley to enable the top pulley to rotate and are connected, also, to the center shaft of the lower case shell 720 to rotate with the lower case shell 720. The cam followers 706 ride in a bearing groove 710 cut in the lower case shell 720. To provide an unobstructed path for the cable 228, the cable guide slots 712 and 722 are positioned between the two cam followers 706 adjacent the idler pulleys 666, 668, and preferably the guide slots 712, 722 are positioned substantially centrally between the pulleys 666, 668. The guide slots 712, 722 are positioned between these cam followers 706 to position the cable 228 on the opposite side of the centrifuge 700 as the contact surfaces between the internal drive belt 670 and the top pulley 698 (shown in FIGS. 20–22). In this manner, the use of separated bearing members 706 in combination with a pair of cable guide slots 712, 722 allows an operator to readily install the umbilical cable 228 without having to blindly go through the inside of the drive system and minimizes binding or other insertion difficulties.

A. Flexible, Disposable Centrifuge Bag

One embodiment of disposable, flexible centrifuge bag 226 is more particularly illustrated in FIGS. 25 and 26. The bag is an integral two stage self-balancing disposable design. The disposable centrifuge bag 226 has a substantially flat, toroidal- or doughnut-shaped configuration having outer and inner perimeters 238 and 240, respectively, and comprises radially extending upper and lower sheets 234, 236 formed from a substantially flexible material. The upper and lower sheets 234, 236 are superimposed and completely sealed together at outer perimeter 238 by a heat weld, rf (radio frequency) weld or other comparable method of adhering two surfaces. Inner perimeter 240 defines core 242 of bag 226. In one embodiment of the invention, centrifuge bag 226 further comprises an inlet tube 248 sandwiched between upper and lower sheets 234, 236 and extending from the center of core 242 defined by inner perimeter 240 to the outer perimeter 238 and an outlet tube 250 sandwiched between upper and lower sheets 234, 236 and extending from the center of the core 242 to the outer perimeter 238. When upper and lower sheets 234, 236 are sealed together at inner perimeter 240, inlet and outlet tubes 248, 250 are thereby sealed therebetween. Inlet and outlet tubes 248, 250 are each in fluid communication with the interior of centrifuge bag 226 and the environment outside centrifuge bag 226. The length of outlet tube 250 is shorter than the length of inlet tube 248.

In one embodiment of this invention, outlet tube 250 is a straight tube as shown in FIG. 31. Alternatively, outlet tube 250 includes a bent fitting 252 fluidly connected to the distal end of outlet tube 250 (FIGS. 25 and 26). The bent fitting 252 may be of any number of configurations, although preferably bent fitting 252 is shaped in the form of a "T", "curved T", a "J", or an "L", as illustrated in FIGS. 27, 28, 29 and 30, respectively. Alternatively, outlet tube 250 and bent fitting 252 may be one contiguous molded unit rather than two connected pieces. Preferably, bent fitting 252 is in the shape of a "T" or a "curved T" as illustrated in FIGS. 27 and 28, respectively. The "T" or "curved T" design of bent fitting 252 ensures that the desired blood component (fraction) will be removed from the sides of the bent fitting 252, rather than from a fraction located above or below the bent fitting, as discussed below in detail.

When the centrifuge bag 226 is positioned in the annular groove 212 of the centrifuge rotor 202 as described above, it is critical that inlet and outlet tubes 248, 250 are seated in groove 222. Further, when rotor cover 206 is positioned over and removably secured to the centrifuge base 204, it is important that inlet and outlet tubes 248, 250 are also seated in groove 224. Seating inlet and outlet tubes 248, 250 in grooves 222, 224 ensures that centrifuge rotor 202 is held in a fixed position between rotor base 204 and rotor cover 206 such that the centrifuge bag 226 and centrifuge rotor 202 rotate together. That is, the fixed position of centrifuge bag 226 ensures that centrifuge bag 226 will not rotate independently of centrifuge bag 226 during centrifugation.

Inlet and outlet tubes 248, 250 are fluidly connected at their proximal ends to umbilical cable 228, which in this particular embodiment is a dual lumen tubing connecting centrifuge bag 226 to source and receiving containers 398, 400, respectively, for the introduction and removal of components from the centrifuge bag 226 during centrifugation (see FIG. 17). Dual lumen tubing 228 comprises inlet lumen 230, which connects inlet tube 248 of centrifuge bag 226 with source container 398, and outlet lumen 232, which connects outlet tube 250 centrifuge bag 226 with receiving container 400. In one embodiment, the inlet and outlet tubes 248, 250 are adapted at their proximal ends for inserting into the inlet and outlet lumens 230 and 232, respectively. Alternatively, connecting means 254 are inserted into the proximal ends of inlet and outlet tubes 248, 250 for connecting the tubes to the inlet and outlet lumens 230, 232 as illustrated in FIG. 26.

In operation, one end of umbilical cable 228 must be secured to rotor assembly 200 to prevent itself from becoming twisted during rotation of rotor assembly 200 by the coaxial half-speed rotation of drive shaft assembly 28, which imparts a like rotation with respect to the rotor 202 axis and consequently to the umbilical cable 228 that is directed through cable guide 102. That is, if rotor assembly 200 is considered as having completed a first rotation of 360° and drive shaft assembly 28 as having completed a 180° half-rotation in the same direction, the umbilical cable 228 will be subjected to a 180° twist in one direction about its axis. Continued rotation of rotor assembly 200 in the same direction for an additional 360° and drive shaft assembly 28 for an additional 180° in the same direction will result in umbilical cable 228 being twisted 180° in the opposite direction, returning umbilical cable 228 to its original untwisted condition. Thus, umbilical cable 228 is subjected to a continuous flexure or bending during operation of the centrifugal processing system 10 of the present invention but is never completely rotated or twisted about its own axis.

Figure 35:
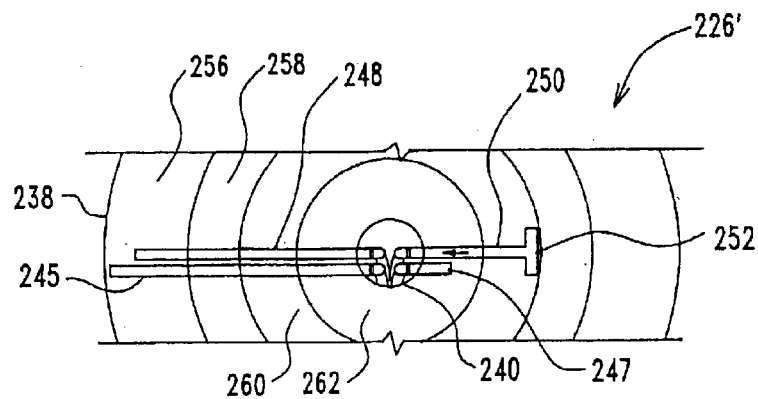

An alternative embodiment of a disposable centrifuge bag of this invention, shown in FIG. 35 comprises two or more inlet tubes and/or two or more outlet tubes, wherein the tubes are fluidly connected to a multiple lumen tubing.

The disposable centrifuge bag 226 is formed from a transparent, substantially flexible material, including but not limited to, polyvinyl chloride, polyethylene, polyurethane, ethylene vinyl acetate and combinations of the above or other flexible materials. Based upon the flexibility of the centrifuge bag 226, the profile of the flexible centrifuge bag 226, shown in FIGS. 25 and 26, is determined at least in part by the amount of fluid contained therein. The profile of centrifuge bag 226 is further defined by the interior configuration of the centrifuge rotor, as discussed below in detail. The ability to manipulate the profile of centrifuge bag 226 based on the interior configuration of the centrifuge rotor is utilized at least in part to maximize the volume of fluid medium that can be contained in centrifuge bag 226 during centrifugation, as will be discussed below.

Figure 32:
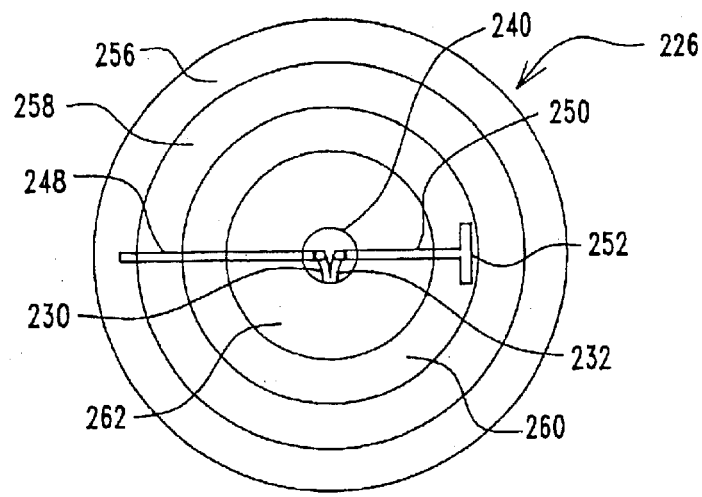
FIG. 32 is a top view of a disposable centrifuge bag of this invention after the centrifugation of whole blood, showing the separated blood components.

The fluid or medium to be centrifuged may be contained within source container 300. For example, when the centrifuge 20 of this invention is used to prepare an autologous platelet gel, the fluid (i.e., whole blood), may be withdrawn from the patient during or prior to surgery into source container 398 containing an anticoagulant. The anticoagulated whole blood is introduced to centrifuge bag 226 through inlet tube 248 via inlet lumen 230 after the centrifuge bag 226 has been positioned in the centrifuge rotor 202 and rotation thereof is initiated. As discussed above, securing centrifuge bag 226 in centrifuge base 204 in grooves 222, 224 holds the centrifuge bag 226 in a fixed position therebetween, such that the centrifuge bag 226 cannot move independently of the centrifuge rotor 202, and therefore the centrifuge bag 226 and rotor assembly 200 rotate concurrently at the same rate of rotation. Rotation of the centrifuge rotor 202 directs the heavier density constituents of the anticoagulated whole blood within the centrifuge bag 226 toward the outer perimeter 238 of the bag 226, while the lighter density constituents remain closer to an inner region, as illustrated in FIG. 32. More specifically, as illustrated in FIG. 32, when the fluid medium being separated is whole blood, the whole blood is separated within centrifuge bag 226 into a red blood cell fraction (256), a white blood cell fraction (258), a platelet rich plasma fraction (260), and a platelet poor plasma fraction (262). As will be appreciated by those of skill in the art, whole blood fractions, red blood cells and plasma are differently colored, and consequently the separation of the fractions can be easily detected by the operator. At an appropriate time during centrifuging, suction or other drawing means may be applied to the interior of centrifuge bag 226 via outlet lumen 232 to remove the desired fraction from the centrifuge bag 226. In a further embodiment, centrifuge cover 206 may further contain concentric index lines to assist the operator in viewing the positions of outlet tube 250 to the RBC plasma interface. Based on the speeds and times the location of the WBC and platelets can be varied with respect to the interface between the red blood cells and plasma. For example, if the rpm is held low (approximately 1,000–1,700, preferably 1,500) the plasma and platelets will separate from the RBC layer, as the rpm's are increased (1,400–1,700) the platelets will separate out of the plasma and reside at the plasma to RBC interface in greater concentrations. With increased speeds, the WBC's reside deeper into the RBC pack.

With further regard to bent fittings 252, in one embodiment a bent fitting is fluidly connected to the distal end of outlet tube 250. While bent fitting 252 is shown in FIG. 32 as having a "T" shape (FIG. 27), this is for illustrative purposes only. Thus, it will be appreciated that bent fitting 252 as shown in FIG. 32 could have a number of other configurations, such as those shown in FIGS. 25–31. The design of bent fitting 252 ensures that the desired component is withdrawn (e.g., the platelet rich plasma fraction 260) with less risk of contamination from withdrawing a portion of the adjacent fraction 258. Thus, in one embodiment, the desired fraction is withdrawn when its position overlaps with the position of bent fitting 252. Alternatively, the inlet tube 248 may be first used to draw off the red blood cell fraction 256, and when it is desirable to remove the predetermined fraction from the centrifuge bag 226, the predetermined fraction is drawn through bent fitting 252 and outlet tube 250 and directed to receiving container 400 via outlet lumen 232.

With continued reference to FIG. 32, as the separation of the fluid medium is initiated by centrifugation, substantially annular regions having constituents of a particular density or range of densities begin to form. For purposes of illustration, the separation of whole blood will be discussed, and as shown in FIG. 32 four regions are represented, each of which contains a particular type of constituent of a given density or range of densities. Moreover, it should be appreciated that there may be a given distribution of densities across each of the regions such that the regions may not be sharply defined. Consequently, in practice the regions may be wider (e.g., a larger radial extent) and encompass a range of densities of constituents.

In the example of FIG. 32, the first region 256 is the outermost of the four regions and contains red blood cells. The second region 258 contains white blood cells, which have a lower density than that of the red blood cells. The third region 260 contains the platelet rich plasma fraction, and the innermost region 262 contains the least dense platelet poor plasma fraction. In one embodiment, it may be desired to harvest the platelet rich plasma fraction in region 260. In order to remove the platelet rich plasma fraction from the centrifuge bag 226, vacuum or suction is provided via outlet lumen 232 to the centrifuge bag 226 to remove a desired portion of region 260. A portion of the fraction 260 that is in the area of the bent fitting 252 is drawn through bent fitting 252 and into an appropriate one of the collection containers 400 (FIG. 17).

Figure 33:
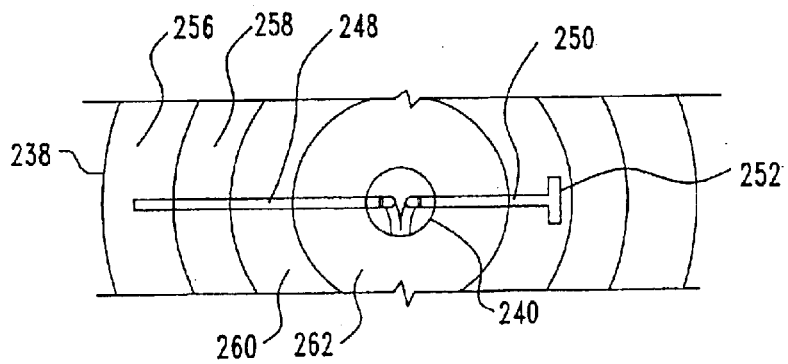
FIGS. 33–39 are schematic illustrations of one method of this invention for separating whole blood components using a disposable centrifuge bag of this invention.

More specifically, FIGS. 33–39 illustrate one method of this invention for the separation of whole blood components, which is a dynamic process. FIG. 33 shows one portion of the centrifuge bag 226, illustrating the separation of the whole blood components after infusion of an aliquot of whole blood into centrifuge bag 226 and centrifugation for approximately 60 seconds to 10 minutes at a rate of rotation between 0 and 5,000 rpms. It will be understood by those of skill in the art that faster speeds of rotation will separate the blood in a shorter prior of time.

FIG. 33 shows the four separated whole blood fractions, with the denser fractions closer to outer perimeter 238, and the less dense fractions closer to inner perimeter 240. While it is well-known that hematocrits (i.e., the volume of blood, expressed as a percentage, that consists of red blood cells) will vary among individuals, ranging from approximately 29%–68%, such variations are easily adjusted for as a result of the novel design of centrifuge bag 226 and consequently will not affect the isolation of any of the desired fractions as discussed below in detail. Thus, for illustrative purposes, it will be assumed that centrifugation of an initial infusion of an aliquot of anticoagulated whole blood will give the profile shown in FIG. 33. In one embodiment, it is desired to harvest the platelet rich plasma fraction 260. This may be achieved by performing a batch separation process or a continuous separation process as described below.

In one embodiment of a batch separation process of this invention for harvesting the platelet rich plasma fraction 260, centrifuge bag 226 has a design as shown in FIG. 32 wherein bent fitting 252 positioned approximately in the area where a platelet rich plasma fraction 260 is typically found after centrifugation of an aliquot of whole blood. This approximation is simplified by the placement of concentric indicator lines 205, 207, and 209, (not shown) in the upper surface of rotor cover 206, wherein the concentric lines 205, 207 and 209 correspond approximately with the edges of regions 260, 258, and 256, respectively. Alternative, concentric lines similar to 205, 207 and 209 may be directly imprinted onto the surface of centrifuge bag 226.

Figure 34:
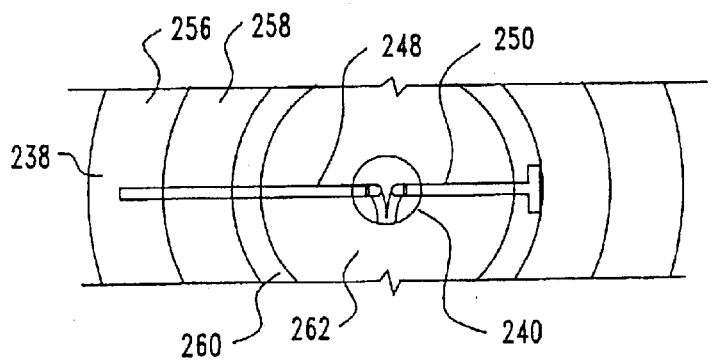

After centrifugation of an aliquot of blood contained in centrifuge bag 226, a substantial portion of the platelet rich plasma fraction 260 is withdrawn from centrifuge bag 226 through bent fitting 252 while centrifuge rotor 202 is still spinning. As the volume of the platelet rich plasma fraction 260 is reduced upon withdrawal, the innermost fraction 262 naturally moves in the direction of the outer perimeter 238 due to centrifugal force, as shown in FIG. 34. The withdrawal of platelet rich plasma fraction 260 is terminated at a point where the platelet poor plasma fraction 262 is close to bent fitting 252 and before any significant portion of platelet poor plasma fraction 262 could be withdrawn through bent fitting 252, as shown in FIG. 34. This point can be determined either visually by the operator by volume, or by a sensor, as described below in detail. After withdrawal of the desired platelet rich plasma fraction 260, inlet lumen 230 is disconnected from the whole blood source container 398 and connected to a disposal container, after which the remaining fluid in centrifuge bag 226 is evacuated through inlet tube 248 and directed to the disposal container. The inlet lumen is then reconnected to the whole blood source container, and the above-described batch process is repeated as many times as required until the necessary quantity of the desired fraction is isolated.

Alternatively, the above-described process can be performed as a continuous process wherein the step of disconnecting the inlet lumen 230 from the whole blood source 398 can be avoided. The continuous process separation of whole blood may be achieve by using a disposable centrifuge bag 226' as illustrated in FIGS. 35–39 comprising an inlet tube 248 and three outlet tubes 245, 247 and 250, wherein the tubes are connected to an umbilical cable comprising four lumens. More specifically, a disposable centrifuge bag for use in a continuous separation of whole blood comprises inlet tube 248 connected via an inlet lumen to a whole blood source container, a first outlet tube 250 connected to a first outlet lumen that is in turn connected to a platelet rich plasma receiving container, a second outlet tube 245 connected via a second outlet lumen to either a red blood cell receiving container or a waste container and a third outlet tube 247 connected via a third outlet lumen to a platelet poor plasma receiving container. In the continuous separation process, after withdrawal of the portion of platelet rich plasma or other cellular components as described above with reference to FIGS. 33 and 34. Centrifuge bag has the capacity to receive an additional volume (aliquot) of whole blood. Consequently, as shown in FIG. 35 infusion of an aliquot of whole blood is reinitiated through first inlet tube 248 with continued centrifugation until the capacity of the centrifuge bag 226' is reached. As a result of the additional volume of blood, the profile of the blood fractions in centrifuge bag 226' will approximately assume the profile shown in FIG. 35. As can be seen in FIG. 35, the additional volume of blood results in a shift of the location of the blood fractions, such that the platelet rich plasma fraction 260 has shifted back into the area of the bent fitting 252, and the platelet poor plasma fraction 262 has shifted back towards the inner perimeter 240 and away from the vicinity of the bent fitting 252. Additional platelet rich plasma 260 can now be removed from centrifuge bag 226' through outlet tube 250 as shown in FIG. 35.

Figure 36:
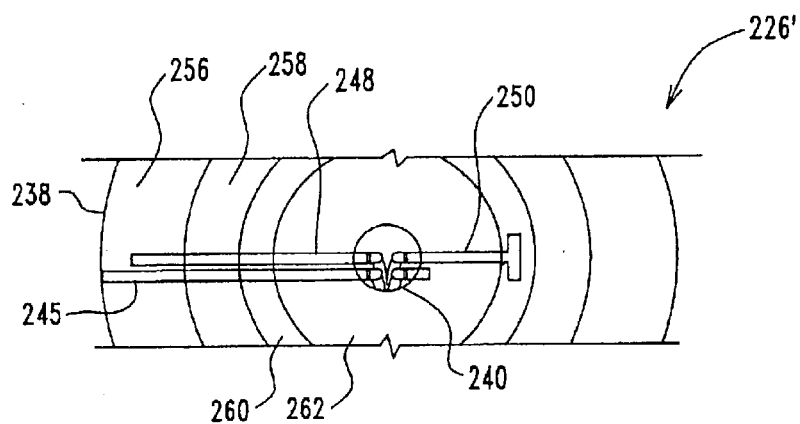

As described above, removal of an additional volume of the platelet rich plasma fraction 260 results in a shift in the location of the platelet poor plasma fraction 262 closer to the outer perimeter 238 and consequently closer to the vicinity of bent fitting 252, as shown in FIG. 36, at which point removal of platelet rich plasma is again temporarily terminated.

Figure 37:
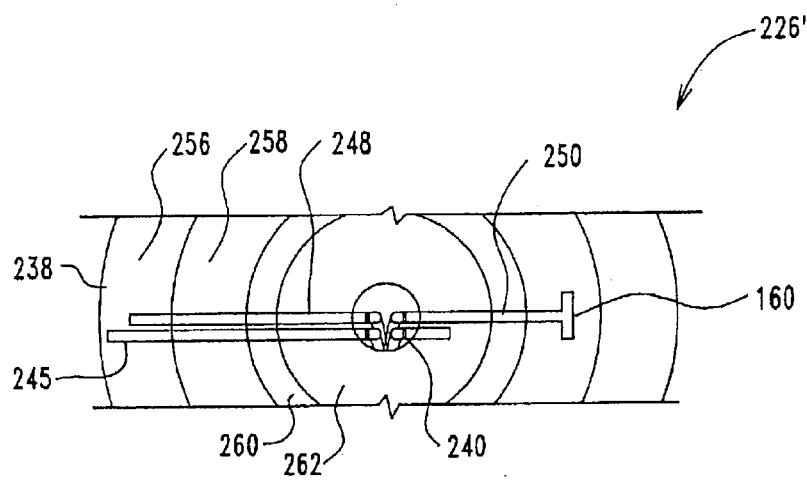

Additional infusions of whole blood aliquots to centrifuge bag 262' and removal of platelet rich plasma (by shifting the position of the platelet rich plasma fraction 260 relative to the position of the bent fitting 252) as described above may be repeated a number of times. Eventually, however, the continued infusion of whole blood followed by removal of only the platelet rich plasma fraction will necessarily result in a gradual increase in the volumes (and consequently the widths) of the remaining blood fractions 256, 258 and 260 in centrifuge bag 226'. In particular, the volume, and therefore the width, of the red blood cell fraction 256 will increase to the extent that the other fractions are pushed closer to the inner perimeter 240 (FIG. 37). As shown in FIG. 37, the increased volume of red blood cells now present in centrifuge bag 226' shifts the location of the fractions towards the inner perimeter 240 such that the white blood cell fraction 260 is now in the vicinity of the bent fitting 252 as opposed to the desired platelet rich plasma fraction 262.

Figure 38:
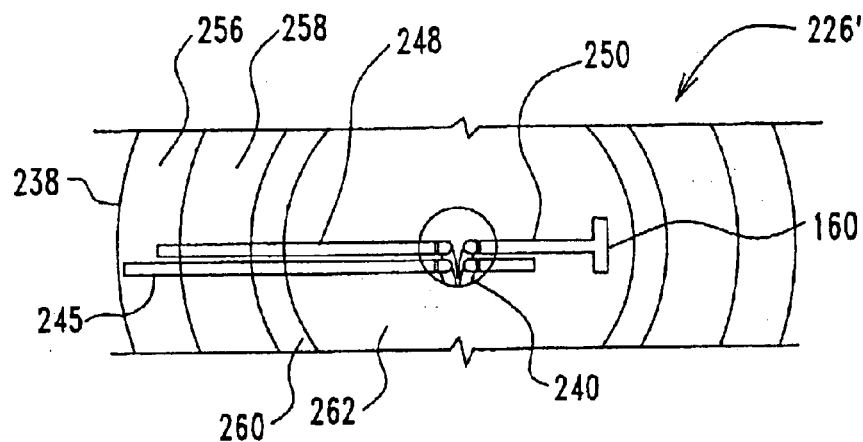
Figure 39:
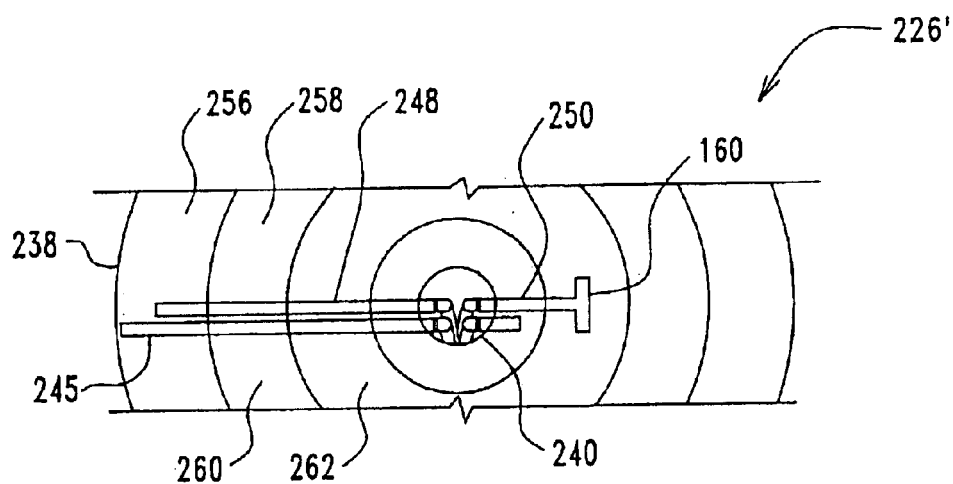

The novel design of centrifuge bag 226' advantageously provides means for shifting the fractions back to the desired locations when the situation shown in FIG. 37 arises. That is, second outlet 245 serves as an inlet conduit for introduction of whole blood aliquots into centrifuge bag 226', also serves the function of withdrawing fractions that are located close to the outer perimeter 238. This is achieved in part by attaching the second outlet lumen to either a red blood cell receiving container or a waste container having a suction means (e.g., syringe, pump, etc.) As shown in FIG. 38, second outlet tube 245, having its distal end close to outer perimeter 238, can be operated to withdraw a substantial volume of the red blood cell fraction 256, which in turn shifts the location of the remaining fractions 258, 260, 262. The withdrawal of the red blood cell fraction 256 may be monitored visually by the operator, or by other means such as a sensor. Alternatively, the positions of the fractions may be shifted by withdrawing the platelet poor plasma fraction 262 through third outlet tube 247, which is connected via a third outlet lumen to a platelet poor plasma receiving container.

FIG. 37 shows that, after withdrawal of a portion of the red blood cell fraction 256, the centrifuge bag 226' again has the capacity to receive an additional volume of whole blood for centrifugation. An additional infusion of an aliquot of whole blood through inlet tube 248 into the centrifuge bag 226' of FIG. 37 and centrifugation will produce the profile illustrated in FIG. 39. The above-described steps may be repeated as needed until the desired amount of platelet rich plasma has been harvested. All of the above-described steps occur while the centrifuge rotor 202 is spinning.

The above-described continuous separation method was illustrated in terms of performing the whole blood infusion step and the platelet rich plasma harvesting step sequentially. An alternative embodiment involves performing the infusion and harvesting steps substantially simultaneously, that is, the platelet rich plasma fraction is withdrawn at approximately the same time as an additional aliquot of whole blood is being added to the bag. This alternate embodiment requires that the centrifuge rotor spin at a rate that results in almost immediate separation of the blood components upon infusion of an aliquot of whole blood.

As stated previously, all of the above-described steps may be monitored either visually by the operator by volume, or by a sensor. If the steps are to be visually monitored, centrifuge cover 206 may further include one or more concentric indicator circles 205, 207, 209 (shown in FIGS. 17 and 18) which may be spaced from the center of cover 206 at distances approximately equal to the outer edges of regions 260, 258 256, respectively, to aid the operator in visualizing the positions of these regions with respect to 252.

FIGS. 33–39 illustrate one embodiment of how the design of centrifuge bags 226 and 226' permit the general locations of the various blood fractions to be shifted to allow for continuous harvesting of a desired blood fraction without the risk of contaminating the harvested blood fraction, and further allow for continual on-line harvesting of a large volume (10 to 5 L's) of blood using a small, portable centrifuge device comprising a 10 cc to 200 cc capacity disposable centrifuge bags 226 and 226'.

For example, the design of centrifuge bag 226 having inlet tube 248 and outlet tube 250 means that the desired component or fraction will be withdrawn from centrifuge bag 226 only through outlet tube 250, while the addition of whole blood aliquots or the removal of other components (e.g., red blood cell fraction 256) will proceed only through dual functional inlet tube 248. In this respect, the harvested fraction (e.g., platelet rich plasma fraction 260) is never withdrawn through inlet tube 248 which was previously exposed to other fluid media (e.g., whole blood or red blood cells). Thus, the design of centrifuge bag 226 offers a significant advantage over conventional centrifuge containers comprising only one tube which serves to both introduce the fluid medium to the container and to withdraw the harvested fraction from the container.

Furthermore, because of its unique design, the use of centrifuge bags 226 and 226' are independent of composition of the whole blood to be centrifuged. For example, as stated above, hematocrits (i.e., the percent volume of blood occupied by red blood cells) vary from individual to individual, and consequently the profile illustrated in FIG. 32 will vary from individual to individual. That is, the width of red blood cell fraction 256 may be wider or narrower, which in turn will result in the platelet rich plasma fraction 260 being positioned further away in either direction from bent fitting 252. However, as discussed above in detail with particular reference to FIGS. 33–34, the design of centrifuge bags 226 and 226' allow the location of the desired fraction to be shifted until it is in the region of bent fitting 252. Such shifting can be brought about, for example using centrifuge bag 226, by withdrawing the red blood cell fraction through inlet tube 248, or by adding whole blood aliquots through inlet tube 248.

Figure 40:
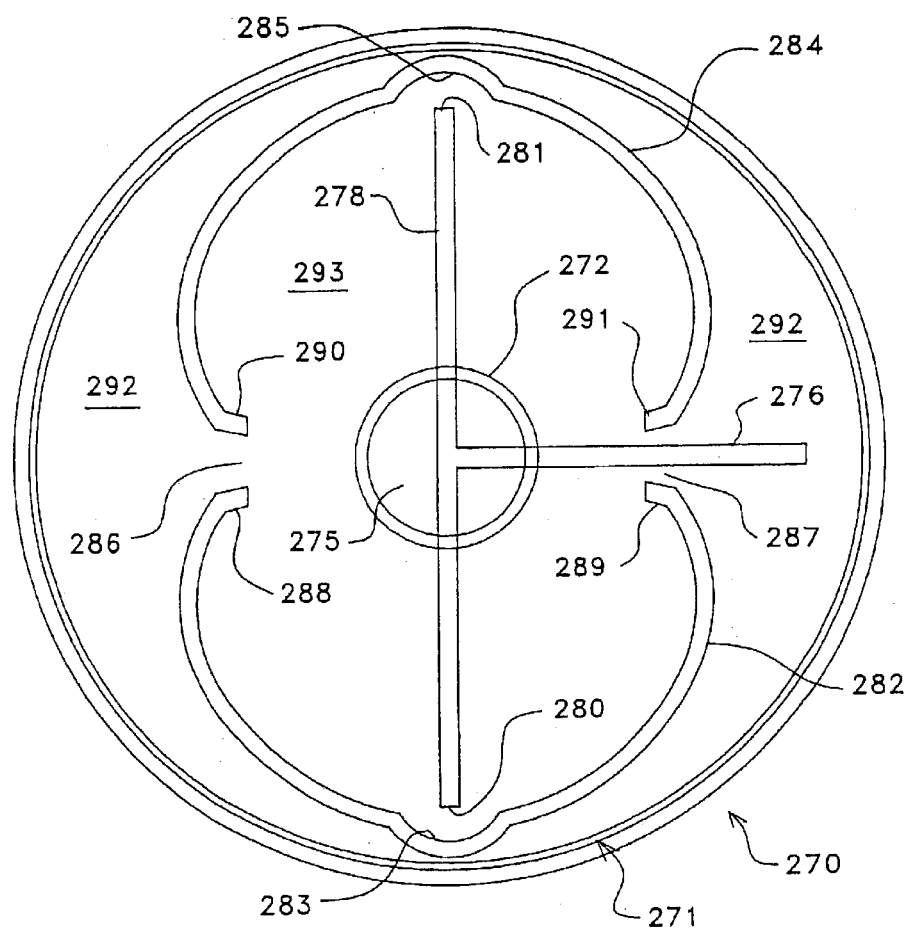
FIG. 40 is a top view of an alternate embodiment of a disposable centrifuge bag of the present invention having inner and outer chambers.

An alternative embodiment of a disposable, flexible centrifuge bag 270 is illustrated in FIG. 40. The disposable centrifuge bag 270 has a substantially flat, toroidal- or doughnut-shaped configuration having outer and inner perimeters 271 and 272, respectively, and comprises radially extending upper and lower sheets 273, 274 formed from a substantially flexible material. The upper and lower sheets 273, 274 are superimposed and completely sealed together at outer perimeter 271 by an rf weld, heat weld or other comparable method of adhering two surfaces. Inner perimeter 272 defines core 275 of centrifuge bag 270. In one embodiment of the invention, centrifuge bag 270 further comprises inlet tube 276 sandwiched between upper and lower sheets 273, 274 and radially extending from the center of core 275 to the outer perimeter 271, and outlet tube 278 sandwiched between upper and lower sheets 273, 274 and extending across the diameter of core 275 and having first and second distal ends 280, 281. When upper and lower sheets 273, 274 are sealed together at inner perimeter 272, inlet and outlet tubes 276, 278 are thereby sealed therebetween. Inlet and outlet tubes 276, 278 are each in fluid communication with the interior of centrifuge bag 270 and the environment outside centrifuge bag 270. Inlet tube 276 and outlet tube 278 are fluidly connected to umbilical cable 228 (not shown), which in this particular embodiment is a dual lumen tubing. Inlet tube 276 is fluidly connected at its proximal end to umbilical cable 228, preferably by an L-shaped connector (not shown), and outlet tube 278 is fluidly connected at its center to umbilical cable 228 via a T-shaped connector (not shown).

The disposable centrifuge bag 270 is formed from a transparent, substantially flexible material, including but not limited to, polyvinyl chloride, polyethylene, polyurethane, ethylene vinyl acetate and combinations of the above or other flexible materials.

Upper and lower sheets 273, 274 of centrifuge bag 270 are further sealed at two portions between the outer perimeter and the inner perimeter. That is, centrifuge bag 270 further comprises a first C-shaped seal 282 located between the outer and inner perimeters 271, 272 and having an first concave indentation or well 283 on the concave side of C-shaped seal 282, and a second C-shaped seal 284 located between the outer and inner perimeters 271, 272 and having a second concave indentation or well 285 on the concave side of C-shaped seal 284. First and second C-shaped seals 282 and 284 are formed by sealing portions of upper and lower sheets 273, 274 together by methods known in the art for sealing two surfaces, including but not limited to rf or heat welding. Ends 288 and 289 of first C-shaped seal 282 are bent inward towards the inner core 275, and likewise ends 290 and 291 of second C-shaped seal 284 are bent inward towards the inner core 275. First and second C-shaped seals 282, 284 have their concave sides facing each other such that the first and second indentations 283, 285 are diametrically opposed to each other. That is, when centrifuge bag 270 is viewed from the top as in FIG. 40, first and second C-shaped seals 282, 284 are mirror images of each other. First and second C-shaped seals 282, 284 together define an outer chamber 292 between the outer perimeter 271 and first and second C-shaped seals 282, 284, wherein the outer chamber 292 has a toroidal configuration and serves as a first processing compartment. First and second C-shaped seals 282, 284 together further define an inner chamber 293 between first and second C-shaped seals 282, 284 and inner perimeter 272, wherein the inner chamber 293 has a toroidal configuration and serves as a second processing compartment. The first and second C-shaped seals 282, 284 are positioned such that ends 288 and 290 are directly opposite and spaced apart from each other to define a first channel 286 therebetween, and such that ends 289 and 291 are directly opposite and spaced apart from each other to define a second channel 287 therebetween, wherein the first and second channels 286, 287 are diametrically opposed and provide fluid communication between the first processing compartment 292 and the second processing compartment 293. Inlet tube 276 extends through either channel 286 or channel 287, and the first and second distal ends 280, 281 of outlet tube 278 extend into first and second indentations 283, 285, respectively.

Centrifuge bag 270 is removably secured between rotor base 204 and rotor cover 206 of rotor 202 in a manner as described above so that centrifuge bag 270 is held in a fixed position relative to rotor base 204 and rotor cover 206 during rotation of the centrifuge rotor 202. As will be appreciated by those of skill in the art, alternative embodiments of rotor base 204 (FIG. 15) and rotor cover 206 (FIG. 16) will be required to accommodate the design of centrifuge bag 270. Thus, an alternate embodiment of rotor base 204 comprises raised column 218 comprising first and second grooves which are perpendicular to each other and extend the diameter of the raised base column 218, such that when rotor 202 is assembled, inlet tube 276 and outlet tube 278 of centrifuge bag 270 are seated in the first and second grooves, respectively, of raised base column 218. Similarly, an alternate embodiment of cover 206 comprises raised column 220 comprising first and second grooves which are perpendicular to each other and extend the diameter of the raised cover column 220, such that when rotor 202 is assembled, inlet tube 276 and outlet tube 278 are further seated in the first and second grooves, respectively, of raised cover column 220.

As stated above, inlet and outlet tubes 276, 278 are fluidly connected to umbilical cable 228, which in this particular embodiment is a dual lumen tubing connecting centrifuge bag 270 to source and receiving containers 398, 400, respectively, for the introduction of the fluid to be centrifuged in bag 270 and for the removal of one or more of the separated components from the centrifuge bag 270 during rotation of the centrifuge 20. Dual lumen tubing 228 comprises inlet lumen 230, which connects inlet tube 276 with source container 398, and outlet lumen 232, which connects outlet tube 278 with receiving container 400.

The fluid or medium to be centrifuged using centrifuge bag 270 may be contained within source container 398. For example, when the centrifuge 20 of this invention is used to prepare an autologous platelet gel, the fluid (i.e., whole blood), may be withdrawn from the patient during or prior to surgery into source container 398 containing an anticoagulant. The anticoagulated whole blood is introduced to centrifuge bag 270 through inlet tube 276 via inlet lumen 230 after the centrifuge bag 270 has been positioned in the centrifuge rotor 202 and rotation thereof is initiated.

Centrifuge bag 270 may be used for the separation and isolation of one or more components dissolved or suspended in a variety of fluid media, including, but not limited to, the separation of cellular components from biological fluids. For example, centrifuge bag 270 is useful for the concentration and removal of platelets from whole blood. Therefore, the following description of the separation of platelets from whole blood using centrifuge bag 270 is merely for purposes of illustration and is not meant to be limiting of the use of bag 270. The separation of a fluid medium such as whole blood in centrifuge bag 270 may be considered to be a two-stage separation process. The first stage of the separation of platelets from whole blood involves separation of a platelet suspension from the red blood cells. The platelet suspension is typically plasma rich in platelets, and it is commonly referred to as platelet-rich plasma (PRP). However, as used herein, the term "platelet suspension" is not limited to PRP in the technical sense, but is intended to encompass any suspension in which platelets are present in concentrations greater than that in whole blood, and can include suspensions that carry other blood components in addition to platelets. The second stage of the separation comprises separating platelets from the platelet suspension to produce a platelet concentrate. As used herein, the term "platelet concentrate" is intended to encompass a volume of platelets that results after a "platelet suspension" undergoes a subsequent separation step that reduces the fluid volume of the platelet suspension. The platelet concentrate may be a concentrate that is depleted of white blood cells and red blood cells.

Figure 41:
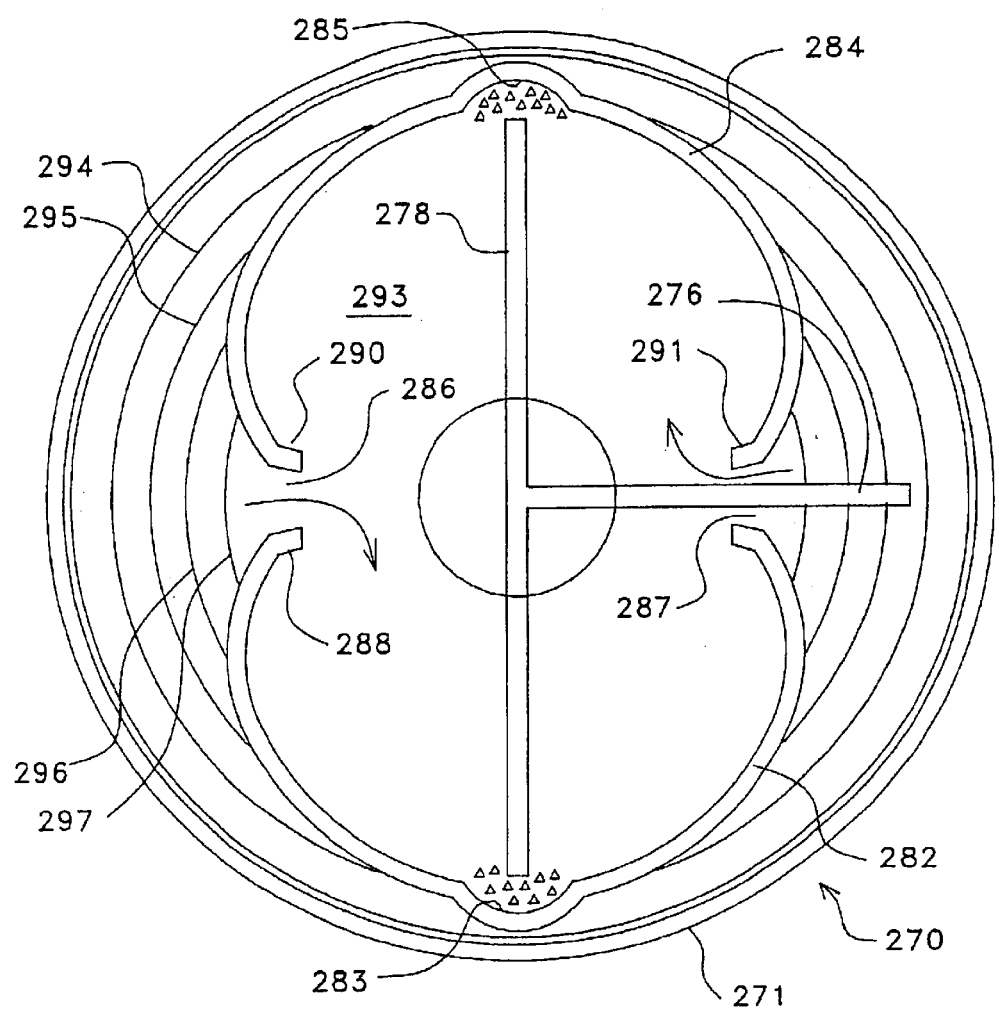
FIG. 41 is a top view of the disposable centrifuge bag shown in FIG. 34 illustrating movement of the red blood cell layer from the outer perimeter toward the inner perimeter.

With reference to FIG. 41, stage one of a whole blood separation process using centrifuge bag 270 begins with the introduction of an aliquot of whole blood into centrifuge bag 270 via inlet tube 276 during rotation of the centrifuge 20. As the aliquot of whole blood enters outer chamber 292 of centrifuge bag 270, it quickly separates radially under the influence of centrifugal force into various fractions within outer chamber 292 based on the densities of the components of the whole blood, including an outermost fraction containing the red blood cells which pack along the outer perimeter 271 of centrifuge bag 270, and an inner fraction comprising the platelet suspension. The platelet suspension after centrifugation of the first aliquot of whole blood is represented in FIG. 41 by ring 294. Continued infusion of whole blood into the first processing compartment 292 adds an additional volume of red blood cells and consequently pushes the platelet suspension inward as represented by ring 295. Additional infusions of whole blood will continue to push the platelet suspension further inward, as represented by rings 296 and 297 until the first processing compartment 292 is substantially filled with red blood cells (the remainder of the volume being plasma) such that the platelet suspension is pushed through channels 286 and 287 into second processing compartment 293. As discussed above, the ends 288, 289 and 290, 291 of C-shaped seals 282, 284, respectively, bend inward, which both helps to funnel the platelet suspension through channels 286, 287 and to minimize the amount of red blood cells that pass through channels 286, 287. The point at which the red blood cells are near the entrance of channels 286, 287 may be monitored either visually or by a sensor, as described below in detail. At this point the infusion of additional aliquots of whole blood is terminated, and the second stage of the two-stage separation process begins.

During stage two of the separation process, the platelet suspension which was pushed through channels 286, 287 into the second processing compartment 293 flow under the influence of centrifugal force towards positions within the second processing compartment 293 that have the greatest radial distances, that is, towards concave wells 283, 285, where the platelets, being the higher density component of the platelet suspension, begin to collect and pack. The platelets can then be withdrawn from concave wells 283, 285 through outlet tube 278. In the above-described two-stage process for the separation of a platelet suspension from whole blood, the first and second C-shaped seals 282, 284 thus serve as physical barriers between the red blood cells and the platelets to facilitate the separation and collection of platelets from whole blood. First and second concave wells 283, 285 act as reservoirs for containing the platelets as they are separated from the platelet suspension in the second stage of the separation process.

After withdrawal of the platelets from the wells 283 and 285, inlet lumen 230 is disconnected from the whole blood source container, after which the remaining components in centrifuge bag 270 are evacuated through inlet tube 276 by applying suction to inlet lumen 230 and are directed to a disposable container. The inlet lumen 230 is then reconnected to the whole blood source container, and the above-described batch process is repeated as many times as required until the desired quantity of platelets has been harvested.

Figure 42:
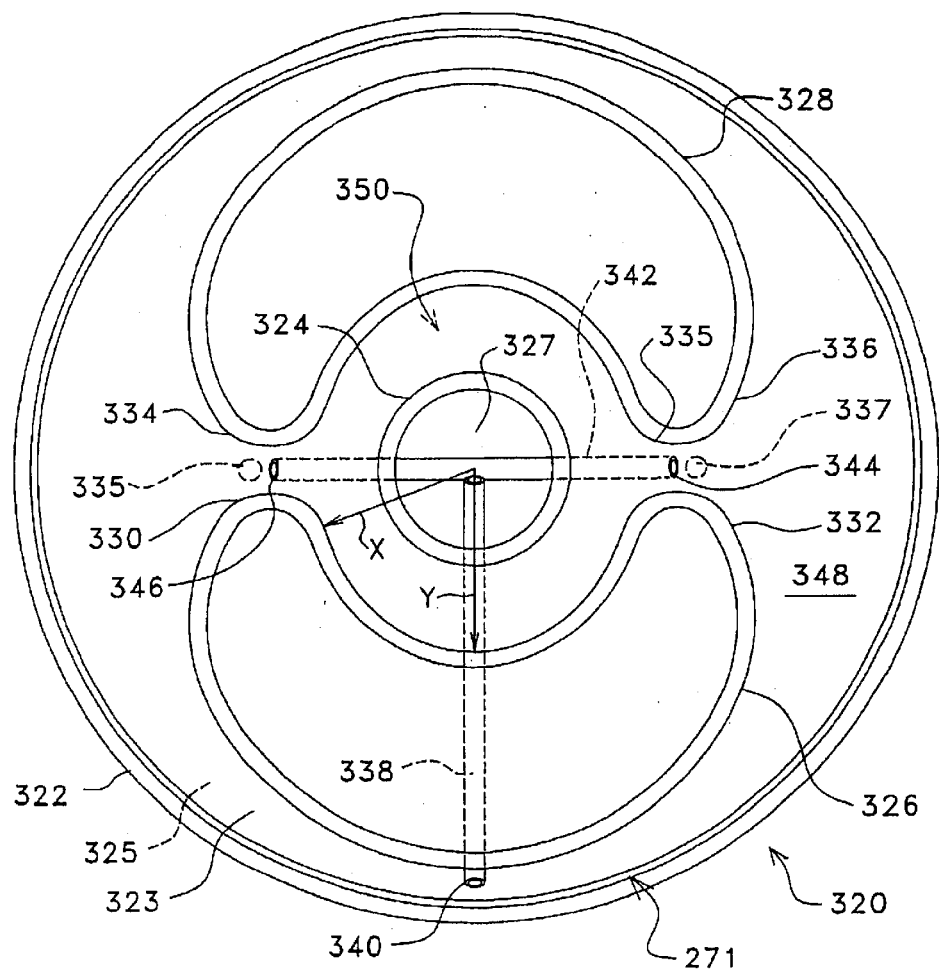
FIG. 42 is a bottom view of an alternate embodiment of a disposable centrifuge bag of the present invention having inner and outer chambers in fluid communication with outlet and inlet ports.

An alternative embodiment of a disposable, flexible centrifuge bag having inner C-shaped seals is illustrated in FIG. 42 as centrifuge bag 320. Disposable centrifuge bag 320 has a substantially flat, toroidal- or doughnut-shaped configuration having outer and inner perimeters 322 and 324, respectively, and comprises radially extending upper and lower sheets 323, 325 formed from a substantially flexible material. The upper and lower sheets 323, 325 are superimposed and completely sealed together at outer perimeter 322 by an rf weld, heat weld or other comparable method of adhering two surfaces. Inner perimeter 324 defines core 327 of bag 320.

Upper and lower sheets 323, 325 of centrifuge bag 320 are further sealed at two portions between the outer perimeter and the inner perimeter. That is, centrifuge bag 320 further comprises a first C-shaped seal 326 located between the inner and outer perimeters 322, 324, and a second C-shaped seal 328 located between the inner and outer perimeters 322, 324. The first and second C-shaped seals 326, 328 have their concave sides facing each other such that when centrifuge bag 320 is viewed from the top as in FIG. 36, first and second C-shaped seals 326 and 328 are mirror images of each other. First and second C-shaped seals 326, 328 together define an outer compartment 348 between the outer perimeter 322 and first and second C-shaped seals 326 and 328, wherein the outer compartment 348 has a toroidal configuration. First and second C-shaped seals further define an compartment 350 between first and second C-shaped seals 326, 328 and inner perimeter 324, wherein the inner compartment 350 has a doughnut shaped configuration. The ends 330 and 332 of first C-shaped seal 326 are slightly curved inward towards the inner core 327, and likewise ends 334 and 336 of second C-shaped seal 328 are slightly curved inward towards the inner core 327. The first and second C-shaped seals 326 and 328 are positioned such that ends 330 and 334 of first and second C-shaped seals 326, 328, respectively, are directly opposite and spaced apart from each other, thereby defining first channel 335 therebetween, and such that ends 332 and 336 of first and second seals 326 and 328, respectively, are directly opposite and spaced apart from each other, thereby defining second channel 337 therebetween, wherein the first and second channels 335 and 337 are diametrically opposed. First and second channels 335 and 337 provide fluid communication between the outer and inner compartments.

Centrifuge bag 320 further comprises an inlet port 340, in the lower sheet 325 for introducing fluid into outer compartment 348. Preferably the inlet port 340 is spaced 90 degrees from channel 335 however it could also be positioned at an angle greater or less than 90 degrees from channel 335. Centrifuge bag 320 further comprises first and second outlet ports 344, 346 in lower sheet 325 and positioned within channels 335 and 337 for withdrawing a fluid compartment from centrifuge bag 320.

In a preferred embodiment, centrifuge bag 320 comprises inlet tube 338 secured to the outside surface of upper sheet 323 or lower sheet 325 and radially extending from the center of core 327 towards the outer perimeter 322, wherein inlet tube 338 is fluidly connected at its distal end to inlet port 340. Inlet port 340 fluidly connects inlet tube 338 with the outer chamber 348 of centrifuge bag 320. Inlet tube 338 is fluidly connected at its proximal end to umbilical cable 228, preferably by an L-shaped connector (not shown). Further, in a preferred embodiment centrifuge bag 320 comprises outlet tube 342 secured to the outside surface of upper sheet 323 or lower sheet 325 and extending across the diameter of core 327, wherein one end of outlet tube 342 is fluidly connected to first outlet port 344 and the other end of outlet tube 342 is fluidly connected to second outlet port 346. Outlet tube is fluidly connected at its center to umbilical cable 228 via a T-shaped connector (not shown).

In an alternative embodiment of this invention, centrifuge bag 320 comprises inlet tube 338 sandwiched between upper and lower sheets 323, 325 and extending radially from the center of core 327 towards outer perimeter 322, wherein inlet tube 328 is fluidly connected at its distal end to inlet port 340, and outlet tube 342 sandwiched between upper and lower sheets 323, 325 and extending across the diameter of core 327, wherein one end of outlet tube 342 is fluidly connected to outlet port 344 and the other end of outlet tube 342 is fluidly connected to outlet port 346. When upper and lower sheets 323, 325 are sealed together at inner perimeter 324, inlet and outlet tubes 338, 342 are thereby sealed therebetween. Inlet tube 338 and outlet tube 342 are fluidly connected to umbilical cable 228 (not shown), which in this particular embodiment is a dual lumen tubing.

Centrifuge bag 320 is removably secured between rotor base 204 and rotor cover 206 of rotor 202 in a manner as described above so that centrifuge bag 320 is held in a fixed position relative to rotor base 204 and rotor cover 206 during rotation of the centrifuge rotor 202. As will be appreciated by those of skill in the art, alternative embodiments of rotor base 204 (FIG. 15) and rotor cover 206 (FIG. 16) as discussed above with respect to centrifuge bag 270 will be required to accommodate the design of centrifuge bag 370.

Centrifuge bag 370 may be used for the separation and isolation of one or more components dissolved or suspended in a variety of fluid media, including, but not limited to, the separation of cellular components from biological fluids. For example, centrifuge bag 370 is useful for the concentration and removal of platelets from whole blood. Therefore, the following description of the separation of platelets from whole blood using centrifuge bag 320 is merely for purposes of illustration and is not meant to be limiting of the use of bag 320. The separation of a fluid medium such as whole blood in centrifuge bag 320 may be considered to be a one-stage separation process. With reference to FIG. 36, centrifugation of whole blood begins with the introduction of an aliquot of whole blood into centrifuge bag 320 through inlet port 340 via inlet tube 338 during rotation of the centrifuge 20. Inlet tube 338 is fluidly connected via inlet lumen 230 of umbilical cable 228 to an anticoagulated whole blood source. As the aliquot of whole blood enters the outer chamber 348 of centrifuge bag 320, it quickly separates radially within outer chamber 348 into various fractions based on the densities of the components of the whole blood, including an outermost fraction containing the red blood cells which pack along the outer perimeter 322 of centrifuge bag 320, and inner fractions containing the platelets and plasma. Continued infusion of whole blood adds an additional volume of red blood cells and consequently pushes the fraction containing platelets inward. Additional infusions of whole blood will continue to push the platelet-containing fraction further inward until the chamber 348 is substantially filled with red blood cells (the remainder of the volume being plasma), such that the platelet-containing fraction is pushed into channels 335, 337 and into the vicinity of outlet ports 344, 346. As discussed above, the ends of C-shaped seals 326, 328 curve slightly inward, which both helps to funnel the platelet-containing fraction into channels 335, 337, and to minimize the amount of red blood cells that flow into channels 335, 337. The point at which the red blood cells are near the entrance of channels 335, 337 may be monitored either visually or by a sensor, as described below in detail. As the platelet-containing fraction enters the vicinity of outlet ports 344, 346, the infusion of whole blood is terminated, and suction or other drawing means is applied to outlet tube 342 to withdraw the platelet-containing fraction through outlet ports 344, 346.

After withdrawal of substantial portion of the platelet rich plasma, inlet lumen 230 is disconnected from the whole blood source container and connected to a disposal container, after which the remaining components in centrifuge bag 320 are evacuated through inlet port 34—by applying suction to inlet tube 276 and are directed to a disposal container. The inlet lumen 230 is then reconnected to the whole blood source container, and the above-described process is repeated as many times as required until the desired quantity of platelets has been harvested.

B. Rigid Centrifuge Container

As can be appreciated, it may be desirable to maximize the surface area of separated fraction to be harvested, since this maximizes the amount of the fraction which may be collected without increasing the potential for introducing impurities into the separation (e.g., adjacent, lighter density components may begin moving into the region of the fraction being harvested), and without increasing the size of the centrifuge to an undesirable degree.

In order to maximize the amount of the desired component (e.g., platelet rich plasma, white blood cells, or platelet poor plasma) which may be harvested, one embodiment of a centrifuge container of this invention for the separation of components in a fluid medium (e.g., whole blood), shown in FIGS. 45–52, is designed to position the desired component (e.g., platelet rich plasma) the platelet rich plasma at a region within the fixed centrifuge container or centrifuge bag so that the desired fraction has a maximum horizontal surface area (i.e., width). Thus, another embodiment of this invention comprises a centrifuge container 500 shown in FIG. 45. FIG. 45 is a side cross-sectional view of a rigid container 500 comprising a rigid, annular body 510 having an axial core 600 that is closed at the top end 610 and opened at the bottom end 620. Rigid container 500 further comprises an interior collection chamber 580 for receiving and holding the fluid medium to be centrifuged and having an outer perimeter 585 and an inner perimeter 590. The side, cross-sectional profile of chamber 580 is generally an off-centered "figure eight" or "dumbbell" shape, as shown in FIG. 46. As used herein, "figure eight" or "dumbbell" shaped means that the height of section A is approximately equal to the height of section C, and the heights of sections A and C are greater that the height of section B. Furthermore, as used herein, "off-center" means that the width $W_1$ from the center of section B to outer perimeter 585 is less than the width $W_2$ from the center of section B to inner perimeter 590 as shown in FIGS. 45 and 46.

Rigid container 500 further comprises inlet channel 550 extending radially from core 600 to a point near the outer perimeter 585 and is fluidly connected at its distal end with the outer area of chamber 580. Rigid container 500 further comprises outlet channel 554 extending radially from core 600 to the more central portion of chamber 580 (i.e., the narrow portion or "neck" of the figure eight cross-section) and is fluidly connected at its distal end with chamber 580. While the inlet and outlet channels 550, 554 are shown in FIG. 45 as being fluidly connected to the top end of chamber 580, the present invention also includes embodiments wherein both channels 550, 554 are in fluid communication with the bottom end of chamber 580, or wherein channel 550 is in fluid communication with the top end of chamber 580 and channel 554 is in fluid communication with the bottom end of chamber 580, or vice versa. Inlet and outlet channels 550, 554 are fluidly connected to dual lumen tubing 228 having an inlet lumen 230 and an outlet lumen 232. Rigid container 500 is removably secured to the upper surface 133 of upper bearing assembly 130 with appropriate screws, fasteners or the like (not shown). Inlet lumen 230 may be connected to a source for fluid medium, and outlet lumen 232 may be connected to a suction means for withdrawing the desired fraction from the chamber 580.

The configuration of chamber 580 is specifically designed to maximize the collection of platelet rich plasma by centrifugation of anticoagulated whole blood. More particularly, the shape of chamber 580 increases the width of the platelet rich plasma fraction when viewed from the top and decreases the depth of the platelet rich plasma fraction when viewed from the side, thus allowing the withdrawal of a greater amount of platelet rich plasma. This unique design can be better explained by comparing FIGS. 44 and 47. FIG. 44 shows a side profile of a rigid centrifuge container 500 as shown in FIG. 43, having a generally oval profile and containing whole blood that has been separated into four fractions by centrifugation. In FIG. 44, width $W_3$ indicates the relative horizontal width of the platelet rich plasma fraction to be harvested, and $D_1$ indicates the relative depth of the platelet rich plasma fraction. FIG. 47 shows a side profile of rigid centrifuge container 580 of this invention having the above-described off-centered figure eight shape and containing whole blood that has been separated into four fractions by centrifugation. In FIG. 47, width $W_4$ indicates the relative horizontal width of the platelet rich plasma fraction 260 to be harvested, and $D_2$ indicates the relative depth of the platelet rich plasma fraction 260. Width $W_4$ is necessarily wider than width $W_3$ in FIG. 44. Thus it can be easily appreciated that upon withdrawal of the platelet rich plasma fraction 260 from the oval shaped container shown in FIG. 44, platelet poor plasma fraction 262 will shift closer to the outlet tube 554 relatively quickly. In contrast the dumbbell shaped profile of chamber 580 shown in FIG. 47 significantly increases the width $W_4$ while decreasing the average depth $D_2$, and therefore a greater portion of the platelet rich plasma fraction 260 can be withdrawn with greater accuracy before the platelet poor plasma fraction 262 reaches the outlet tube 554.

In an embodiment where the platelet rich plasma is to be collected one could design chamber 580 as follows. The configuration of chamber 580, that is, the relative heights A, B, and C as shown in FIG. 46, will be determined based on the typical location of the platelet rich plasma fraction 260 after centrifugation of whole blood. For example, in a rigid centrifuge container 500 as illustrated in FIG. 45, having chamber 580 with a 30 ml capacity and a radius of approximately 65 mm measured from its rotational axis to the edge 630, the platelet rich plasma will collect in chamber 580 at a region at a radial position ranging from about 35 to about 60 mm from the axis. In this region of the chamber 580, as illustrated in FIG. 46, the chamber 580 has a height of about 10 mm such that the horizontal surface area "B" of this region, illustrated in FIG. 46, is about 4 mm². Consequently, it can be appreciated that because of the unique configuration of chamber 580, the surface area of the platelet rich plasma fraction 260 as illustrated in FIG. 47 may be maximized without undesirably increasing the overall size of the rigid centrifuge container 500. It will be appreciated by those skilled in the art that various geometric designs may be utilized depending on the fluid medium being centrifuged and the cellular fraction to be collected. The process for harvesting platelets from whole blood using rigid container 500 may be achieved in a manner similar to that described for bag 226

Rigid centrifuge container 500 may be made from any number of rigid, transparent materials that are capable of withstanding typical sterilization conditions, including but not limited to acrylic resins, polycarbonate, or any clear thermal plastic. Preferably rigid container 500 is made of a cost-effective material that is relatively inexpensive to dispose of C. Centrifuge Rotor Having a Complex Interior Geometry An alternate embodiment of a centrifuge rotor of this invention for holding flexible centrifuge bag 226 is illustrated in FIGS. 48–52. Generally and referring to FIGS. 48 and 49, the centrifuge rotor 755 is defined by a rotor base 760 (FIGS. 48, 50 and 52) having a lower channel 780, and a rotor cover 770 (FIGS. 49 and 51) having an upper channel 782. The annular interior chamber 784 (FIG. 48) of rotor 755 is defined by lower and upper channels 780, 782, and has a generally off-centered figure eight side cross-sectional configuration specifically designed to maximize the collection of platelet rich plasma by centrifugation of anticoagulated whole blood, as discussed below in detail.

Figure 51:
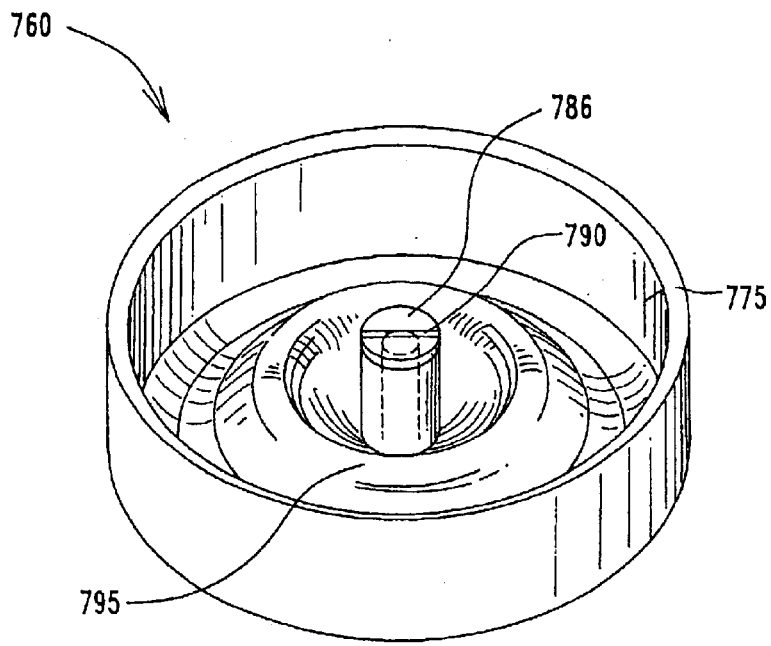
FIG. 51 is a perspective view of the rotor base of FIG. 50.
Figure 52:
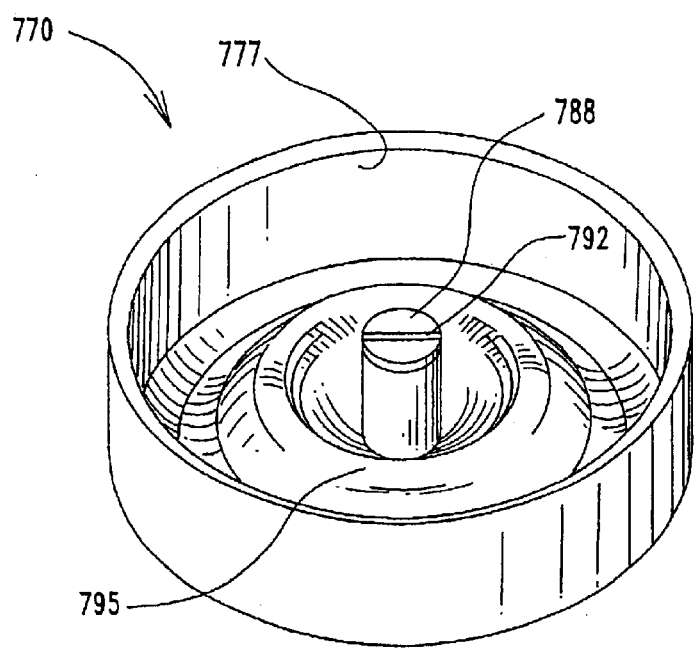
FIG. 52 is a perspective view of the rotor cover of FIG. 49.

As illustrated in FIGS. 51 and 52, rotor base 760 comprises raised annular rim 775 and raised column 786 which is axially disposed in the interior of rotor base 760. Raised column 786 further has a groove 790 (FIG. 52) extending the diameter of column 786. The height of rim 775 is equal to the height of column 786. As illustrated in FIG. 51, rotor cover 770 comprises raised annular rim 777 and raised column 788 which is axially disposed in the interior of cover 770. Raised column 788 further has a groove 792 (FIG. 52) extending the diameter of column 788. The height of rim 777 is equal to the height of column 788. Rotor base 760 and rotor cover 770 are preferably made from any number of rigid transparent materials including, but not limited to acrylic resins, polycarbonate, or any clear thermal plastic.

Figure 48:
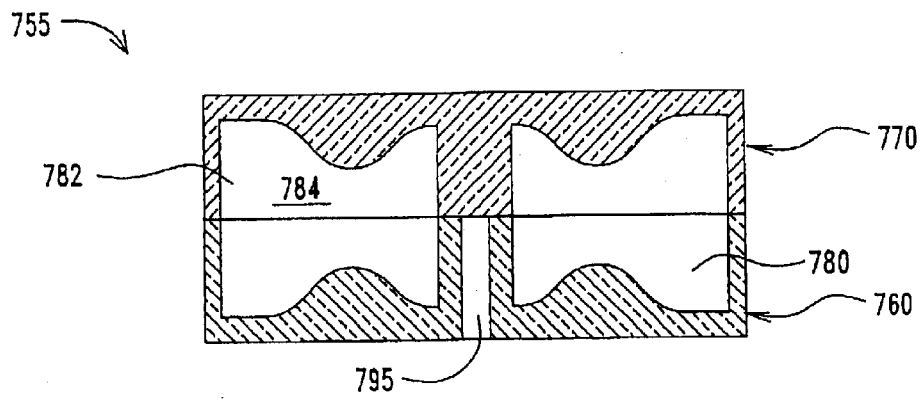
FIG. 48 is a side cross-sectional view of an alternative embodiment of an assembled centrifuge rotor of this invention comprising the rotor cover of FIG. 49 and the rotor base of FIG. 50.
Figure 49:
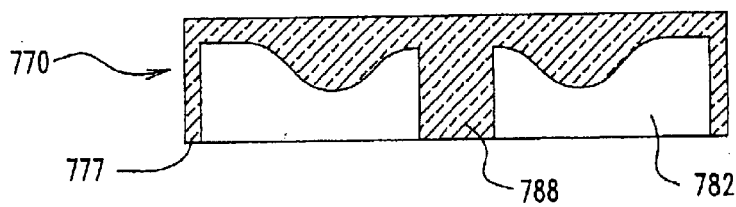
FIG. 49 is a side cross-sectional view of an alternative embodiment of a rotor cover of this invention.
Figure 50:
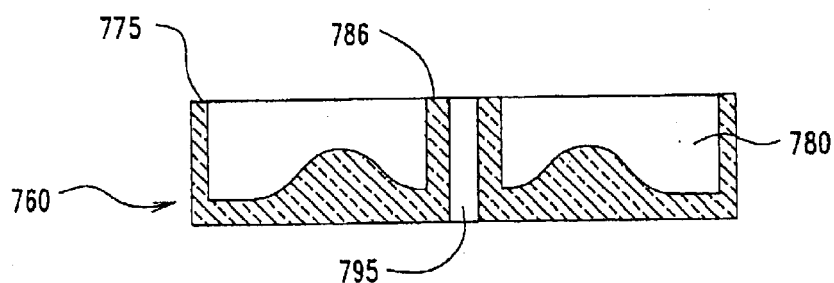
FIG. 50 is a side cross-sectional view of an alternative embodiment of a rotor base of this invention.

When centrifuge rotor 755 is to be assembled for use, flexible, doughnut-shaped centrifuge bag 226 having a center core 242 is placed in rotor base 760 such that center column 786 preferably, but not necessarily, extends through the core of centrifuge bag 226, and inlet and outlet tubes 248, 250 of bag 226 are seated in groove 790. Rotor cover 770 is superimposed on rotor base 760 such that grooves 790 and 792 are aligned and further so that inlet and outlet tubes 248, 250 are seated in groove 792. In one embodiment, when cover 770 is appropriately secured to base 760 (e.g., with screws, clamps, or the like), rims 775 and 777 are in complete contact with each other, and columns 786 and 788 are preferably in complete contact with each other, thereby creating chamber 784 (FIG. 48). Alternatively when cover 770 is secured to base 760 as described, the inner perimeter of bag 226 is secured between columns 786 and 788 such that the columns do not physically contact each other.

When the generally flat, flexible centrifuge bag 226 is contained within chamber 784 prior to the infusion of a fluid medium (e.g., whole blood), it will not fill the entire volume of chamber 784 but rather will have a radially extending, flat shape as centrifuge rotor 755 is spinning. However, after a sufficient volume of the fluid medium (e.g., whole blood) has been introduced into flexible bag 226 through inlet tube 248 such that bag 226 is substantially completely filled, it will be appreciated that filled centrifuge bag 226 will conform to the shape of chamber 784 and consequently will have a off-centered figure eight shaped cross-section.

The off-centered figure eight configuration of the chamber 784 is of approximately the same configuration as the rigid bag 500. Therefore, for the same reasons, the shape of chamber 784 (and consequently the shape of filled bag 226), will assume an off-centered figure eight shape wherein the width of the platelet rich plasma fraction is greatly increased relative to the width of a filled bag having an elliptical cross-sectional shape (see, for example, FIGS. 46 and 47).

As discussed above, a number of methods may be utilized to gauge the harvesting of the desired fraction (such as, but not limited to, platelet rich plasma) from the centrifuge bag. For instance, the separation of platelet rich plasma fraction may be indicated by visual observation of a concentric ring containing the platelet rich plasma (which will be a less colored fraction) and an outer red-colored concentric ring containing the red blood cells. In this case, when such fraction(s) have been separated, the platelet rich plasma may be withdrawn from centrifuge bag 226 by bent fitting 160 to direct the platelet rich plasma to the appropriate collector.

As an alternative to the foregoing, sensors may be incorporated as discussed in detail below to detect the presence of the platelet rich plasma fraction.

Based upon the foregoing, it can be appreciated that the centrifugal processing system 10 and the centrifuge rotors and bags of this invention have a plurality of features which are suited to harvesting platelet rich plasma, white blood cells, platelet poor plasma or red blood cells from a patient's whole blood in accordance with each of the aspects of the present invention. For example, as discussed above, hematocrits (the volume of blood occupied by red blood cells, expressed as a percentage) vary from individual to individual. Thus, depending on the amount of red blood cells present in a particular sample, the exact radial location of various blood components within the centrifuge bag after centrifugation will also vary. The centrifuge bags of this invention overcome this issue by having an inlet tube capable of not only introducing whole blood into the centrifuge bag, but also capable of withdrawing some of all of the red blood cell fraction as needed to shift the location of the fraction to be harvested into the area of the outlet tube. Such features are presented in centrifuge bags 226, 270, 320 and 500. Yet another embodiment of the centrifuge bags of this invention which overcomes problems with varying hematocrits is centrifuge bag 226' having multiple outlet tubes.

Additionally, the centrifugal processing system 10 effectively provides a closed system which enhances the potential for maintaining a desired degree of sterility associated with the entire procedure since materials can thus be both provided to and removed from the centrifuge bag during rotation of the centrifuge via, for instance, a dual lumen tubing connected to a fluid source (e.g., anticoagulated whole blood withdrawn from a patient before or during surgery) and collection containers (i.e., for the preparation of a platelet gel), without interrupting the process, and thus without significant exposure of the materials to environmental conditions.

Moreover, the portable size of the centrifugal processing system 10 in combination with the above-described features of shifting the separated fractions and maximizing the surface area of the harvested fraction allows for increased processing capabilities autologous platelet gel over larger, conventional centrifuges The on-line harvesting capabilities of the centrifugal processing system 10 allows for continuous, dynamic separation and collection of platelet rich plasma, white blood cells, red blood cells and platelet poor plasma, by adjusting the input and removal of fluid medium and separated fractions as described above. Further, the orientation of the flexible and rigid centrifuge bags of this invention and of the contents therein (e.g., being generally radially extending) is not significantly modified in the transformation from separation to harvesting of the various constituents. Moreover, vortexing throughout the contents of the centrifuge bags of this invention is reduced or eliminated since the centrifugal processing system 10 does not have to be decelerated or stopped for addition of fluid medium or removal of the various fractions therefrom.

Further, the general orientation of the flexible and rigid centrifuge bags of the invention (e.g., substantially horizontal) is maintained during removal of the desired whole blood fraction similar to the orientation of the centrifuge bags assumed during centrifugation to further assist in maintaining the degree of separation provided by centrifugation. Consequently, the potential is reduced for disturbing the fractions to the degree where the separation achieved is adversely affected.

Although the present invention has been described with regard to the separation of whole blood components, it will be appreciated that the methods and apparatus described herein may be used in the separation components of other fluid media, including, but not limited to whole blood with density gradient media; cellular components, or sub-sets of the four whole blood components previously defined.

Figure 53:
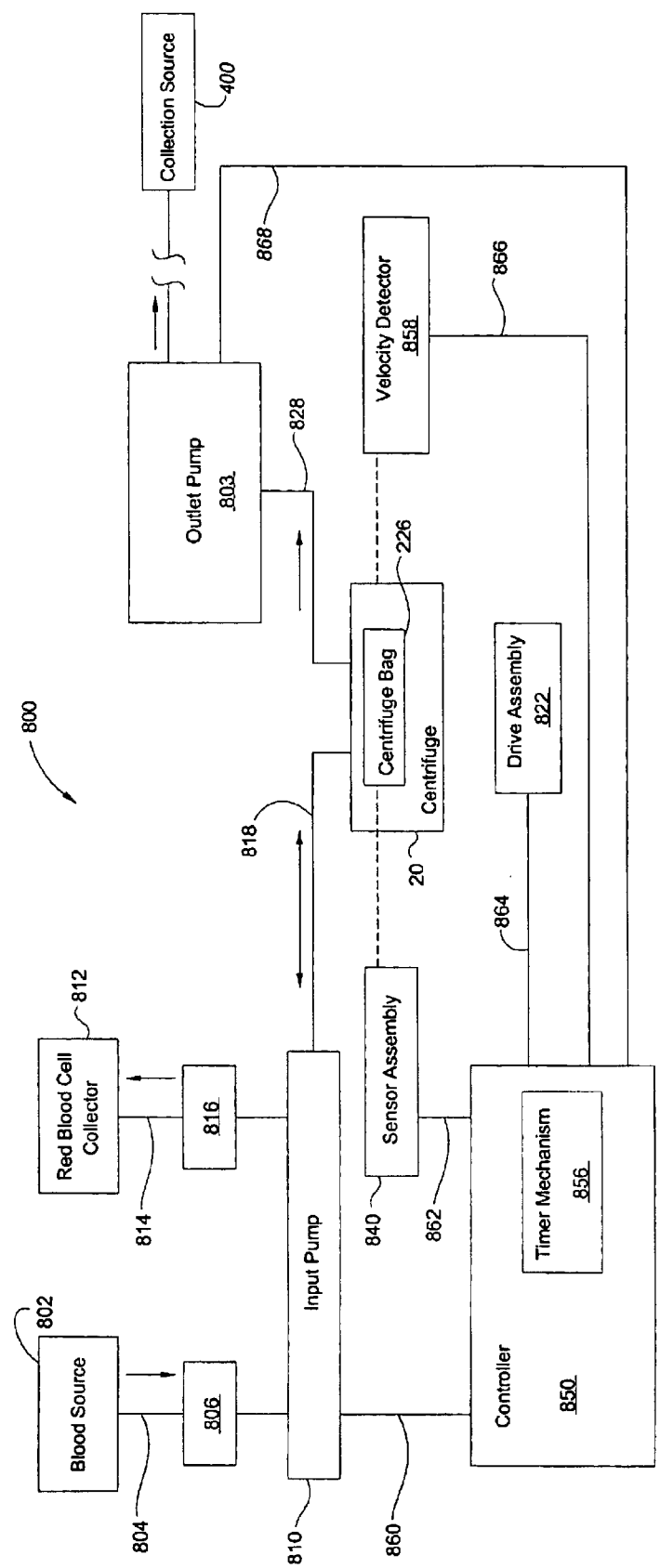
FIG. 53 is a block diagram illustrating the components of a centrifugal processing system of the present invention.

While blood separation and materials handling may be manually controlled, as discussed above, a further embodiment of the present invention provides for the automation of at least portions of the separation and material handling processes. Referring to FIG. 53, an automated centrifugal processing system 800 is illustrated that is generally configured to provide automated control over the steps of inputting blood, separating desired components, and outputting the separated components. The following discussion of the processing system 800 provides examples of separating platelets in a blood sample, but the processing system 800 provides features that would be useful for separating other components or fractions from blood or other fluids. These other uses for the processing system 800 are considered within the breadth of this disclosure. Similarly, the specific components discussed for use in the processing system 800 are provided for illustration purposes and not as limitations, with alternative devices being readily apparent to those skilled in the medical device arts.

In the embodiment illustrated in FIG. 53, the processing system 800 includes a blood source 802 connected with a fluid line 804 to an inlet pump 810. A valve 806, such as a solenoid-operated valve or a one-way check valve, is provided in the fluid line 804 to allow control of flow to and from the blood source 802 during operation of the inlet pump 810. The inlet pump 810 is operable to pump blood from the blood source 802 through the fluid line 818 to a centrifuge 20. Once all or a select portion of the blood in the blood source 802 have been pumped to a blood reservoir 824 of the centrifuge 820 the inlet pump 810 is turned off and the blood source 802 isolated with valve 806. The inlet pump 810 may be operated at later times to provide additional blood during the operation of the processing system 800 (such as during or after the removal of a separated component).

The centrifuge 20 preferably includes a flexible centrifuge bag, for example 226, 226', 270, or 320, positioned within the rotor 202 for collecting the input blood, or alternatively rotor 202 may be a rigid container having an off centered figure eight shaped chamber, which may collect blood directly as discussed previously. Thus, while the embodiment described below illustrates a centrifuge having bag 226, it is to be understood that the alternative centrifuge bags disclosed herein may be used in a similar manner. The centrifuge 20 as discussed above has an internal mid-shaft gear assembly 108 that provides the motive force to rotate the rotor assembly 200, and particularly the rotor 202, at a rotation rate that is adequate to create centrifugal forces that act to separate the various constituents or components of the blood in the rotor 202. The drive assembly 822 may comprise a number of devices useful for generating the motive force, such as an electric motor with a drive shaft connected to internal drive components of the centrifuge 20. In a preferred embodiment, the drive assembly 822 comprises an electric motor that drives a belt attached to an exterior portion of the centrifuge 20 and more particularly to the timing belt ring 44. To obtain adequate separation, the rotation rate is typically between about 0 RPM and 5000 RPM, and in one embodiment of the invention, is maintained between about 0 RPM and 5000 RPM.

As discussed in detail previously, components of particular densities assume radial positions or belts at differing distances from the central axis A of the rotor 202. For example, the heavier red blood cells typically separate in an outer region while lower density platelets separate into a region more proximal to the central axis of the rotor 202. Between each of these component regions, there is an interface at which the fluid density measurably changes from a higher to a lower density (i.e., as density is measured from an outer to an inner region), and this density interface is used in some embodiments of the centrifugal processing system 800 to identify the location of component regions (as will be discussed in more detail below). In a preferred embodiment, the drive assembly 822 continues to operate to rotate the centrifuge 20 to retain the separation of the components throughout the operation of the centrifugal processing system 800.

Once blood separation has been achieved within the rotor 202, the outlet pump 830 is operated to pump select components from the rotor 202 through outlet lumen 828. As discussed previously, in relation to the features of the disposable blood centrifuge bag 226, the centrifuge bag held within the rotor 202 preferably is configured to allow the selective removal of a separated blood component, such as platelets located in a platelet rich plasma region, by the positioning of an outlet lumen 232 a radial distance from the central axis of the centrifuge bag 226. Preferably, this radial distance or radial location for the outlet lumen is selected to coincide with the radial location of the desired, separated component or the anticipated location of the separated component. In this manner, the outlet pump 830 only (or substantially only) removes a particular component (such as platelets into container 400) existing at that radial distance. Once all or a desired quantity of the particular component is removed from the centrifuge bag 226, operation of the outlet pump 830 is stopped, and a new separation process can be initiated. Alternatively, in a preferred embodiment, additional blood is pumped into the centrifuge by 226 by further operating the inlet pump 810 after or concurrent with operation of the outlet pump 830.

A concern with fixing the radial distance or location of the outlet port is that each blood sample may have varying levels or quantities of different components. Thus, upon separation, the radial distance or location of a particular component or component region within the centrifuge bag 226 varies, at least slightly, with each different blood sample. Additionally, because of the varying levels of components, the size of the component region also varies and the amount that can be pumped out of the centrifuge bag 226 by the outlet pump 830 without inclusion of other components varies with each blood sample. Further, the position of the component region will vary in embodiments of the separation system 800 in which additional blood is added after or during the removal of blood by the outlet pump 830.

To address the varying location of a particular separated component, the centrifugal processing system 800 preferably is configured to adjust the location of a separated component to substantially align the radial location of the separated component with the radial location of the outlet port. For example, the centrifugal processing system 800 may be utilized to collect platelets from a blood sample. In this example, the centrifugal processing system 800 preferably includes a red blood cell collector 812 connected to the inlet pump 810 via fluid line 814 having an isolation valve 816 (e.g., a solenoid-operated valve or one-way check valve). Alternatively, the pump or syringe may also act as the valve. The inlet pump 810 is configured to selectively pump fluids in two directions, to and away from the centrifuge 820 through fluid line 818, and in this regard, may be a reversible-direction peristaltic pump or other two-directional pump. Similarly, although shown schematically with two fluid lines 804 and 814, a single fluid line may be utilized as an inlet and an outlet line to practice the invention.

Operation of the inlet pump 810 to remove fluid from the centrifuge bag 226 is useful to align the radial location of the desired separated component with the outlet tube 250 and inlet tube 248 of the centrifuge bag 226. When it is desired to align platelets or platelet rich plasma with the outlet tube 250, the inlet tube 248 connected to lumen 232 and 230, respectively, inlet tube 248 is preferably at a greater radial distance than the outlet tube 250. When suction is applied to the inlet lumen 230 by inlet pump 810, red blood cells are pumped out of the centrifuge bag 226 and into the red blood cell collector 812. As red blood cells are removed, the separated platelets (i.e., the desired component region) move radially outward to a new location within the centrifuge bag 226. The inlet pump 810 is operated until the radial distance of the separated platelets or platelet region from the central axis is increased to coincide with the radial distance or location of the outlet tube 250 of the centrifuge bag 226. Once substantial alignment of the desired component region and the outlet tube 250 is achieved, the outlet pump 830 is operated to remove all or a select quantity of the components in the aligned component region.

To provide automation features of the invention, the centrifugal processing system 800 includes a controller 850 for monitoring and controlling operation of the inlet pump 810, the centrifuge 20, the drive assembly 822, and the outlet pump 830. Numerous control devices may be utilized within the centrifugal processing system 800 to effectively monitor and control automated operations. In one embodiment, the controller 850 comprises a computer with a central processing unit (CPU) with a digital signal processor, memory, an input/output (I/O) interface for receiving input and feedback signals and for transmitting control signals, and software or programming applications for processing input signals and generating control signals (with or without signal conditioners and/or amplifiers). The controller 850 is communicatively linked to the devices of the centrifugal processing system 800 with signal lines 860, 862, 864, 866, and 868 which may include signal conditioning devices and other devices to provide for proper communications between the controller 850 and the components of the centrifugal processing system 800.

Once blood is supplied to the blood source container 802, the operator pushes the start button and the controller 850 transmits a control signal over signal line 864 to the drive assembly 822, which may include a motor controller, to begin rotating the centrifuge 20 to cause the components of the blood in centrifuge bag 226 to separate into radially-positioned regions (such as platelet rich plasma regions). After initiation of the centrifuge spinning or concurrently with operation of the drive assembly 822, the controller 850 generates a control signal over signal line 860 to the inlet pump 810 to begin pumping blood from the blood source container 802 to the centrifuge bag 226 of the centrifuge 20. In some embodiments of the processing system 800, the drive assembly 822 is operable at more than one speed or over a range of speeds. Additionally, even with a single speed drive shaft the rotation rate achieved at the centrifuge 20 may vary. To address this issue, the processing system 800 may include a velocity detector 858 that at least periodically detects movement of the centrifuge bag 226 portion of the centrifuge 20 and transmits a feedback signal over signal line 866 to the controller 850. The controller 850 processes the received signal to calculate the rotation rate of the centrifuge 20, and if applicable, transmits a control signal to the drive assembly 822 to increase or decrease its operating speed to obtain a desired rotation rate at the centrifuge bag 226.

To determine when separation of the components in the centrifuge bag 226 is achieved, the processing system 800 may be calibrated to account for variations in the centrifuge 20 and drive assembly 822 configuration to determine a minimum rotation time to obtain a desired level of component separation. In this embodiment, the controller 850 preferably includes a timer mechanism 856 that operates to measure the period of time that the centrifuge 20 has been rotated by the drive assembly 822 (such as by beginning measuring from the transmission of the control signal by the controller 850 to the drive assembly 822). When the measured rotation time equals the calibrated rotation time for a particular centrifuge 20 and drive assembly 822 configuration, the timing mechanism 856 informs the controller 850 that separation has been achieved in the centrifuge bag 226. At this point, the controller 850 operates to transmit control signal over signal line 860 to the input pump 810 to cease operation and to the outlet pump 830 over signal line 868 to initiate operation to pump a separated component in the component region adjacent the outlet port of lumen 232 of centrifuge bag 226 through fluid line 828. In another embodiment where rotation time is utilized by controller 850, the velocity feedback signal from the velocity detector 858 is utilized by the controller 850 to adjust the rotation time as necessary to obtain the desired level of component separation. For example, the centrifugal processing system 800 can be calibrated for a number of rotation rates and the corresponding minimum rotation times can be stored in a look up table for retrieval by the controller 850 based on a calculated rotation rate. Rotational rates may be varied either manually or automatically to optimize cellular component position and or concentration.

Because the location of component separation regions varies during separation operations, a preferred embodiment of the centrifugal processing system 800 includes a sensor assembly 840 to monitor the separation of components within the centrifuge bag and to transmit feedback signals over line 862 to the controller 850. As will be understood by those skilled in the art, numerous sensor devices exist for detecting the presence of certain components in a fluid, and specifically a blood, sample. Many of these devices comprise a source of radiant energy, such as infrared, laser, or incandescent light, and a compatible radiant energy-sensitive detector that reacts to the received energy by generating an electric signal. Briefly, these radiant energy devices are useful because the detected signal varies in a measurable fashion with variances in the density of the material through which beams of the radiant energy are passed. According to the invention, the sensor assembly 840 may comprise any of these well-known types of radiant energy source and detector devices and other sensor devices useful for measuring the existence of constituents of fluids such as blood.

The source and the detector of the sensor assembly 840 are preferably located within the centrifugal processing system 800 to allow monitoring of the centrifuge bag 226 and, particularly, to identify the presence of a particular blood component in a radial position coinciding with the radial position of the outlet port of the centrifuge bag 226. In one embodiment, the radiation beams from the source are transmitted through a "window" in the centrifuge bag 226 that has a radial location that at least partially overlaps the radial location of the outlet port. During operation of the centrifugal processing system 800, the feedback signals from the detector of the sensor assembly 840 allow the controller 850 to identify when a density interface has entered the window. This may occur for a number of reasons. The change in density may occur when red blood cells are being removed by operation of the inlet pump 810 to remove fluid from the centrifuge bag 226 via the inlet tube 248. The change in density may also occur when a denser component is being added to the centrifuge bag 226 causing the particular blood component to be pushed radially inward. In the centrifugation of whole blood, this occurs when additional blood is added by operation of the input pump 810 and red blood cells collect in a region radially outward from the platelet region.

To account for differing movement of the density interface, the window of the radiation source may be alternatively positioned radially inward from the location of the outlet tube 250 of the centrifuge bag 226. By positioning the window inward from the outlet tube 250, the controller 850 can identify when the outlet pump 830 has nearly removed all of the particular component of the monitored region and/or when the inlet pump 810 has removed a quantity of denser components causing the monitored region to move radially outward. The controller 850 can then operate to send control signals to turn off the outlet pump 830 or the inlet pump 810 (as appropriate) to minimize the amount of undesired components (lower density components) that enter the outlet tube 250. Alternatively, the sensor assembly 840 may have two radiation sources and detectors, and the second window of the sensor assembly 840 may be located a distance radially outward from the outlet tube 250. With two sensing windows, the sensor assembly 840 is operable to provide the controller 850 information about a density interface moving radially inward toward the outlet tube 250 (such as when red blood cells are added). In response, the controller 850 can generate a control signal to the inlet pump 810 to operate to pump the denser components, such as red blood cells, out of the centrifuge bag 226. Two sensing windows also allow the controller 850 to detect a density interface moving outward, which allows the controller 850 to shut off the outlet pump 830 (and/or the inlet pump 810 to stop evacuating processes) and/or to start the inlet pump 810 to add additional blood.

Figure 54:
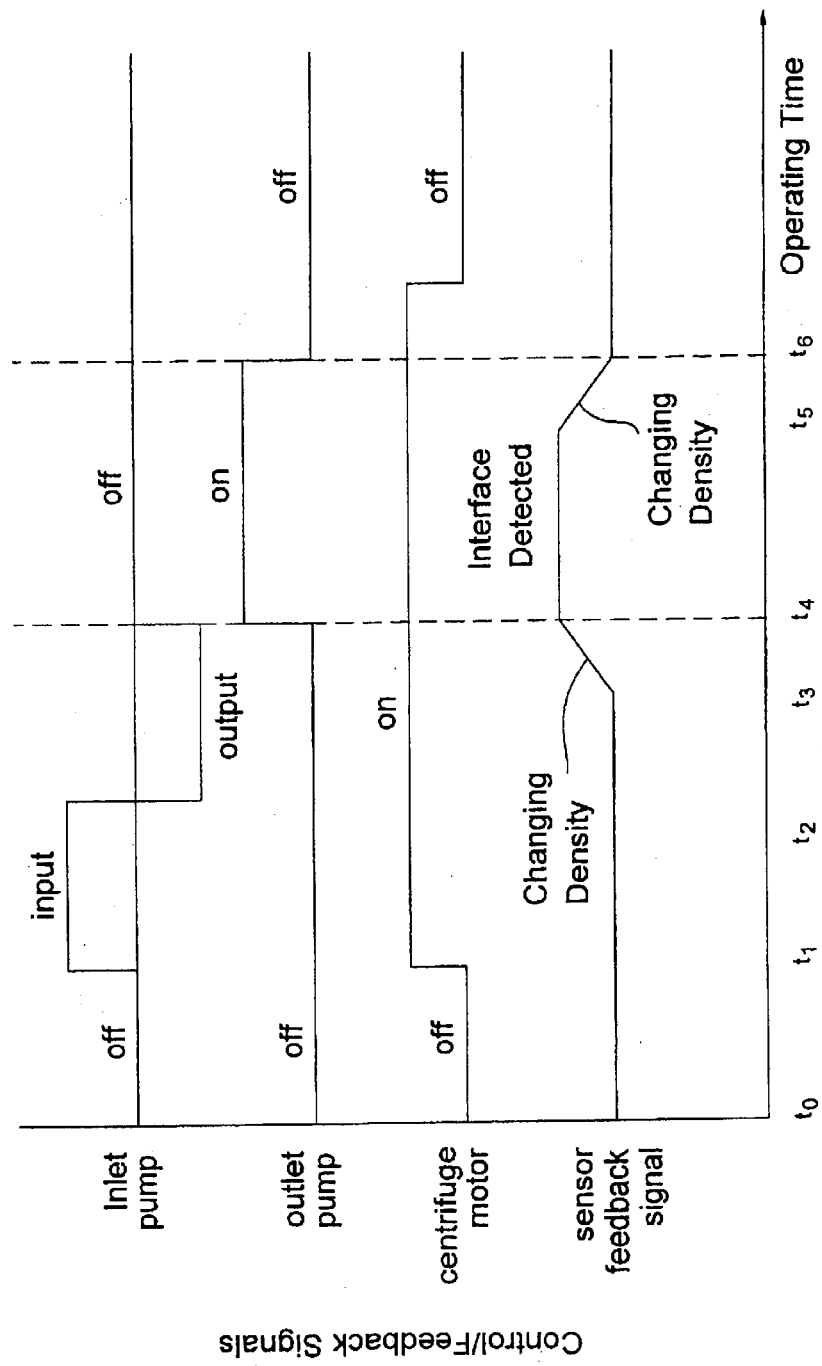
FIG. 54 is a graph illustrating the timing and relationship of transmission of control signals and receipt of feedback signals during operation of one embodiment of the automated centrifugal processing system of FIG. 53.

To further clarify operation of the processing system 800, FIG. 54 is provided which illustrates the timing and relationship of control signals generated by the controller 850 and the receipt of feedback signals from the sensor assembly 840. In this embodiment, the radiation detector of the sensor assembly 840 is positioned adjacent outlet tube (inlet to the outlet pump 830) in the centrifuge bag 226 to sense density changes in the fluid flowing past the outlet tube 250. As illustrated, operation of the processing system 800 begins at time $t_0$, with the inlet pump 810, the outlet pump 830, and the centrifuge drive assembly 822 all being off or not operating. At time $t_1$, the controller 850 operates in response to operator input or upon sensing the blood source 802 is adequately filled (sensor not shown) to generate a control signal on line 864 to begin operating the centrifuge drive assembly 822 to rotate the centrifuge bag 226. In some embodiments, this control signal over line 864 also contains rotation rate information to initially set the operating speed of the drive assembly 822. Concurrently or at a selected delay time, the controller 850 generates a control signal on line 860 to start the inlet pump 810 in a configuration to pump fluid to the centrifuge bag 226 over fluid line 818. The sensor assembly 840 provides an initial density feedback signal to the controller 850 on line 862, which the controller 850 can process to determine an initial or unseparated density adjacent the outlet tube. Alternatively, the controller 850 may be configured to request a feedback signal from the sensor assembly 840 after a set delay period (as measured by the timer mechanism 856) to allow separation of the components being pumped into the centrifuge bag 226 (such as the calibrated, minimum rotation time discussed above) into regions.

At time $t_2$, the controller 850 functions to align the region having the desired density, such as a region comprising a higher density of platelets, adjacent the detector of the sensor assembly 840 (i.e., adjacent the outlet tube). To achieve alignment, the controller 850 transmits a control signal over line 860 to the inlet pump 810 to stop pumping fluid to the centrifuge bag 226, to reverse pumping directions including shutting valve 806 and opening valve 816, and to begin pumping components having a higher density then the particular, desired component from the centrifuge bag 226 to the collector 812. For example, when the centrifugal processing system 10 is operated to separate and collect platelets or platelet rich plasma, the inlet pump 810 at time, $t_2$, is operated to pump out the red blood cell fraction by applying suction at the inlet tube 248 to the centrifuge bag 226. At time $t_3$, the density of the fluid adjacent the outlet tube 250 begins to change as denser components are removed by the inlet pump 810, and the sensor feedback signal being transmitted to the controller 850 changes in magnitude. The sensor feedback signal continues to change in magnitude (either becoming stronger or weaker depending on the particular sensor utilized and the material being collected) until at time $t_4$, when the controller 850 processes the feedback signal and determines that the density of the adjacent fluids is within a desired range. This transition can also be thought of as detecting when an interface between two regions of differing densities passes by the location of the detector of the sensor assembly 840.

With the region of the desired, separated component aligned with the outlet tube 250, the controller 850 operates at time $t_4$, to send a control signal over line 860 to stop operations of the inlet pump 810. Also, at time $t_4$, or at any time thereafter, the controller 850 generates a control signal over line 868 to begin operation the outlet pump 830 to apply suction at the outlet tube 250 of the centrifuge bag 226 to remove the desired component, such as the platelet rich plasma fraction, from the centrifuge bag 226. At time $t_5$, the sensor feedback signal again begins to change in magnitude as the density of the fluid near the outlet tube 250 begins to change, such as when platelet poor plasma begins to enter the sampling window of the sensor assembly 840. At time $t_6$, the density of the fluid adjacent the outlet tube 250 and, hence, in the sampling window is outside of a desired density range (e.g., the fluid has less than a predetermined percentage of platelets or other desired fluid component). In response, the controller 850 transmits a control signal on line 868 to halt operations of the outlet pump 830. Of course, the controller 850 can be operated to transmit the signal to the outlet pump 830 at any time prior to time $t_6$, such as at a time after time $t_5$, when the density of the adjacent fluid begins to change but prior to time $t_6$ or based on volume removed. The controller 850 can then operate any time after time $t_6$, to halt operation of the centrifuge drive assembly 822. Further, as discussed above, operations of the separation centrifugal processing system 800 can be repeated with the inlet pump 810 being operated to add additional fluid, e.g., blood, after time $t_6$. Alternatively, the inlet pump 810 and the outlet pump 830 may be operated concurrently to add an additional volume of blood with a corresponding new amount of the component being collected after time $t_4$, to extend the period of time between detection of the interface at time $t_4$ and the detection of an out of range density at time $t_6$.

In the above discussion of the automated processing system 800, a sensor assembly 840 was shown in FIG. 53 schematically, and it was noted that the location of a radiant energy source and a detector may be any location within the processing system 800 useful for obtaining an accurate measurement of separating blood components within the centrifuge bag 226. For example, the source and detector can be both positioned within the centrifuge 20 at a location adjacent the centrifuge bag 226. In this embodiment, problems may arise with providing proper signal and power line connections to the source and sensor and with accounting for the rotation of the centrifuge and portions of the sensor assembly 840. Hence, one preferred embodiment of the processing system 800 provides for an externally positioned sensor assembly 840 including source and detector to simplify the structure of the centrifuge 20 while still providing effective density determinations of fluids within the blood reservoir.

Figure 55:
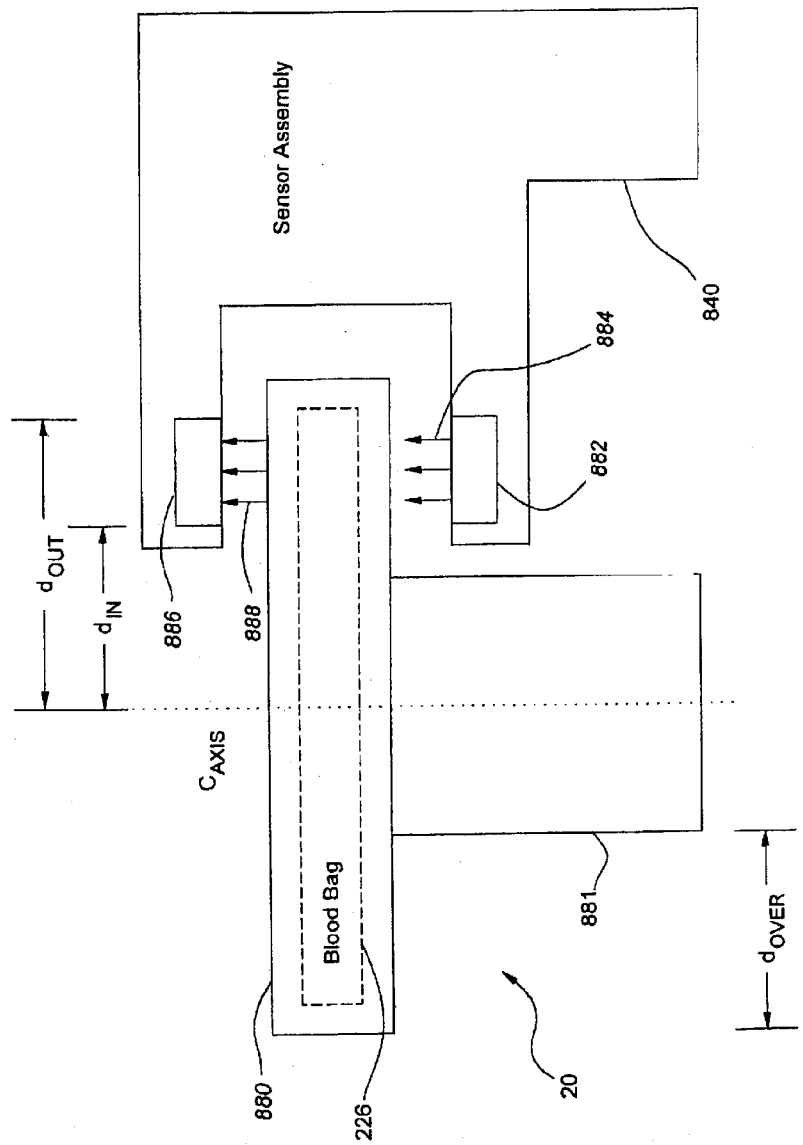
FIG. 55 is a side view of an alternative embodiment of the automated centrifugal processing system of FIG. 53 showing a centrifuge having a rotor wherein the reservoir extends over the outer diameter of the centrifuge portion that facilitates use of an externally positioned sensor assembly.

FIG. 55 illustrates a general side view of the relevant components of this external sensor embodiment of the centrifugal processing system 800. Generally, the centrifuge 20 comprises a rotor extension portion 880 and a drive portion 881, which is connected to the drive assembly 822 (connection not shown). Both the centrifuge 20 and the rotor extension portion 880 rotate about a central or rotation axis, $C_{axis}$, of the centrifuge 20. As discussed in more detail with respect to the internal gearing features of the centrifuge 20, the drive portion 881 spins in a ratio of 2 to 1 (or other suitable ratio) relative to the reservoir extension portion 880 to control twisting of inlet and outlet fluid lines to the rotor extension portion 880. The internal gearing features of the centrifuge 20 also enable the centrifuge 20 to effectively obtain rotation rates that force the separation of components with differing densities while limiting the risk that denser components, such as red blood cells, will become too tightly packed during separation forming a solid, dense material that is more difficult to pump or remove from the centrifuge 20.

Referring again to FIG. 55, the rotor extension portion 880 is shown located on the upper end of the centrifuge 20 and includes a centrifuge bag 226 or other receptacle. Preferably, the rotor extension portion 880 is fabricated from a transparent or partially transparent material, such as any of a number of plastics, to allow sensing of fluid densities. The rotor extension portion 880 extends a distance, $d_{over}$, beyond the outer edge of the centrifuge 20 as measured radially outward from the central axis, $c_{axis}$. The distance, $d_{over}$, is preferably selected such that the desired component, such as the platelet rich plasma fraction, to be collected readily separates into a region at a point within the centrifuge bag 226 that also extends outward from the centrifuge 20. In this regard, the rotor extension portion 880 is also configured so that the centrifuge bag 226 extends within the rotor extension portion 880 to a point near the outer circumference of the rotor extension portion 880. The distance, $d_{over}$, selected for extending the rotor extension portion 880 is preferably selected to facilitate alignment process (discussed above) and to control the need for operating the input pump 810 to remove denser components. In one embodiment, the distance, $d_{over}$, is selected such that during separation of a typical blood sample center of the platelet rich region is about one half the extension distance, $d_{over}$, from the circumferential edge of the centrifuge 20.

The sensor assembly 840 is entirely external to the centrifuge 20 as shown in FIG. 55. The sensor assembly 840 includes a source 882 for emitting beams 884 of radiant energy into and through the rotor extension portion 880 and the included centrifuge bag 226. Again, as discussed previously, the radiant energy source 882 may be nearly any source of radiant energy (such as incandescent light, a strobe light, an infrared light, laser and the like) useful in a fluid density sensor and the particular type of detector or energy used is not as important as the external location of the source 882. The sensor assembly 840 further includes a detector 886 that receives or senses beams 888 that have passed through the centrifuge bag 226 and have impinged upon the detector 886. The detector 886 is selected to be compatible with the source 882 and to transmit a feedback signal in response sensing the energy beams 888. The detector 886 (in combination with the controller 850 and its processing capacities) is useful for detecting the density of fluids in the centrifuge bag 226 between the source 882 and the detector 886. Particularly, the sensor assembly 840 is useful for identifying changes in fluid density and interfaces between fluids with differing densities. For example, the interface between a region containing separated red blood cells and a region containing the platelet rich plasma fraction, and the interface between the platelet rich plasma region and a platelet-poor plasma region.

With some source and detector configurations, a sampling window is created rather than a single sampling point (although a single sampling point configuration is useful as part of the invention as creating a window defined by a single radial distance). The sampling window is defined by an outer radial distance, $d_{OUT}$, from the central axis, $c_{axis}$, and an inner radial distance, $d_{IN}$. As may be appreciated, for many source and detector configurations the size of the sampling window may be rather small approximating a point and may, of course vary in cross-sectional shape (e.g., circular, square, rectangular, and the like). As discussed previously, it is preferable that the sensor assembly 840 be positioned relative to the reservoir extension portion 880 and the centrifuge bag 226 such that the sampling window created by the source 882 and detector 886 at least partially overlaps the radial position of the region created during separation processes containing a component of particular density, such as platelets. This may be a calibrated position determined through calibration processes of the centrifuge 20 in which a number of blood (or other fluid) samples are fully separated and radial distances to a particular region are measured. The determined or calibrated position can then be utilized as a initial, fixed location for the sensor assembly 840 with the source 882 and detector 886 being positioned relative to the rotor extension portion 880 such that the sampling window overlaps the anticipated position of the selected separation region. Of course, each sample may vary in content of various components which may cause this initial alignment to be inaccurate and operations of the centrifugal processing system 800 may cause misalignment or movement of regions. Hence, alignment processes discussed above preferably are utilized in addition to the initial positioning of the sampling window created by the sensor assembly 840.

In an alternate embodiment, the sensor assembly 840 is not in a fixed position within the separation system 800 and can be positioned during separation operations. For example, the sensor assembly 840 may be mounted on a base which can be slid radially inward toward the centrifuge 20 and radially outward away from the centrifuge 20 to vary the distances, $d_{IN}$ and $d_{OUT}$. This sliding movement is useful for providing access to the centrifuge bag 226, such as to insert and remove a disposable bag. During operation, the sensor assembly 840 would initially be pushed outward from the centrifuge 20 until a new bag was inserted into the centrifuge bag 226. The sensor assembly 840 could then be slid inward (or otherwise moved inward) to a calibrated position. Alternatively, the centrifugal processing system 800 could be operated for a period of time to achieve partial or full separation (based on a timed period or simple visual observation) and then the sensor assembly 840 slid inward to a position that the operator of the centrifugal processing system 800 visually approximates as aligning the sampling window with a desired region of separated components (such as the platelet rich plasma region). The effectiveness of such alignment could then readily be verified by operating the sensor assembly 840 to detect the density of the fluids in the centrifuge bag 226 and a calculated density (or other information) could be output or displayed by the controller 850. This alternate embodiment provides a readily maintainable centrifugal processing system 800 while providing the benefits of a fixed position sensor assembly 840 and added benefits of allowing easy relative positioning to obtain or at least approximate a desired sample window and separation region alignment.

Figure 56:
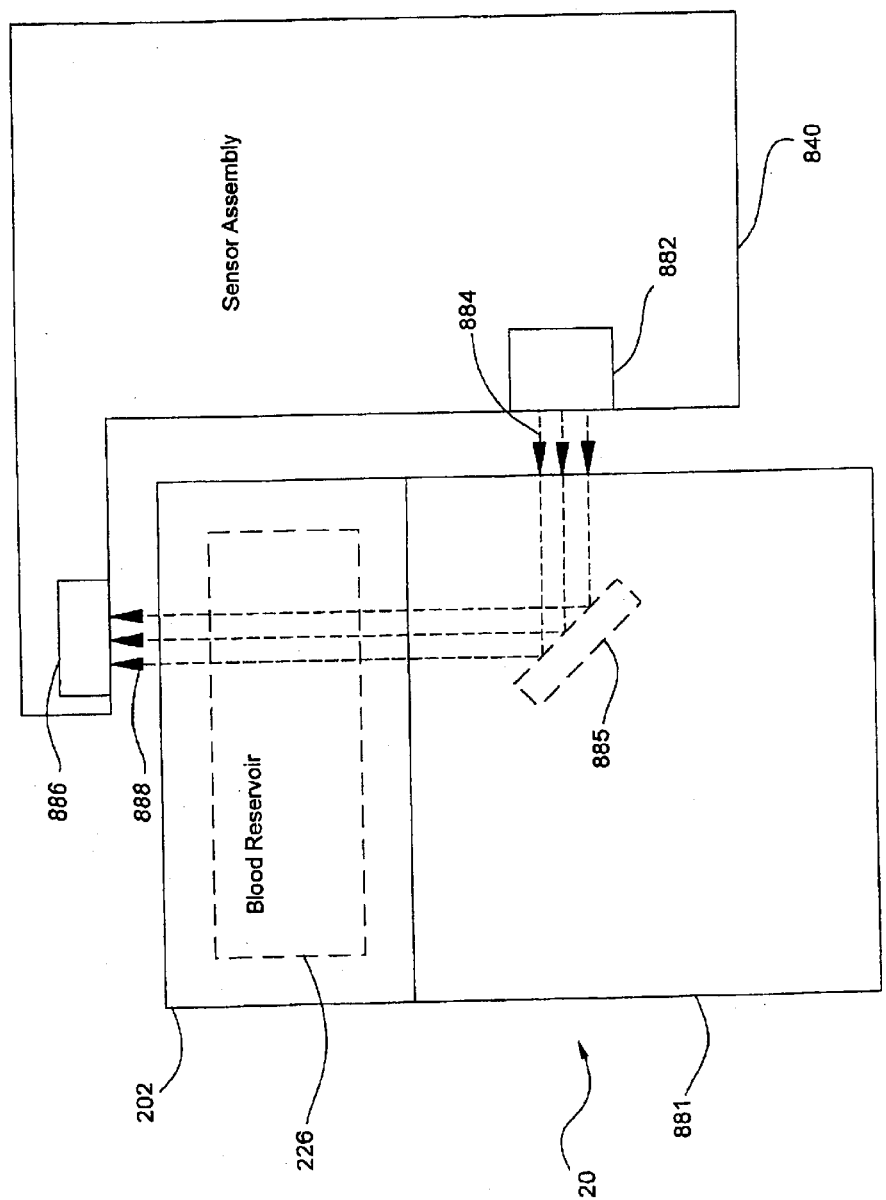
FIG. 56 is a side view of a further alternative embodiment of the external sensor assembly feature of the centrifugal processing system of the invention without an extended rotor and illustrating the positioning of a reflector within the centrifuge.
Figure 57:
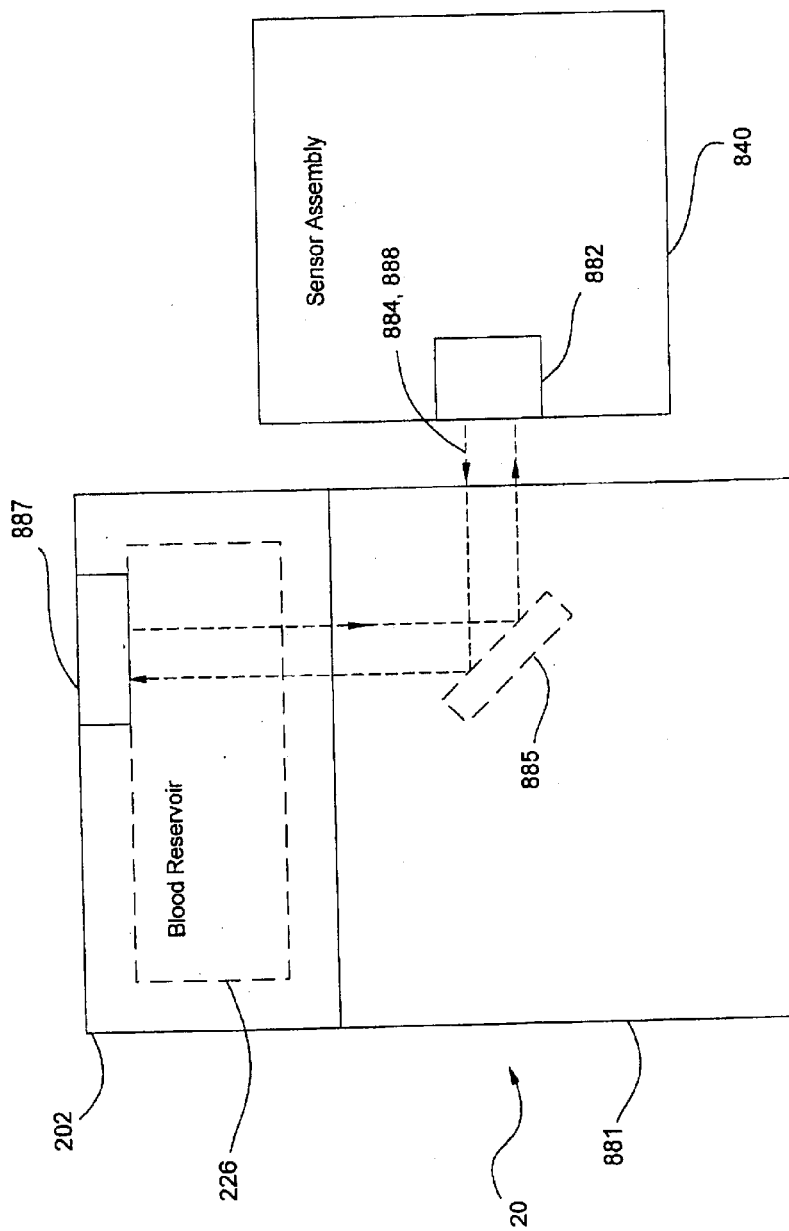
FIG. 57 is a side view of yet another embodiment of the external sensor assembly feature of the centrifugal processing system of the invention illustrating a single radiant energy source and detector device.

In some situations, it may be preferable to not have a rotor extension portion 880 or to modify the rotor extension portion 880 and the sensor assembly 840 such that the extension is not significant to monitoring the separation within the blood reservoir or centrifuge bag 226. Two alternative embodiments or arrangements are illustrated in FIGS. 56 and 57 that provide the advantages of an external sensor assembly 840 (such as an external radiation source and detector). With these further embodiments provided, numerous other expansions of the discussed use of an external sensor will become apparent to those skilled in the arts and are considered within the breadth of this invention.

Referring to FIG. 56, a rotor 202 is illustrated that has no extending portion (although some extension may be utilized) and contains the centrifuge bag 226. Again, the rotor 202 and centrifuge bag 226 are preferably fabricated from plastics or other materials that allow radiation to pass through to detect changes in densities or other properties of fluid samples within the centrifuge bag 226. In this embodiment of the sensor assembly 840, the radiation source 882 and the detector 886 are not positioned on opposing sides of the rotor 202. Instead, a reflector 885 (such as a mirror and the like) is positioned within the drive portion 881 of the centrifuge to receive the radiation beams 884 from the radiation source 882 and direct them through the portion 880 and centrifuge bag 226. The detector 886 is positioned within the sensor assembly 840 and relative to the centrifuge 20 to receive the deflected or reflected beams 888 that have passed through the fluid sample in the centrifuge bag 226. In this manner, the sampling window within the centrifuge bag 226 can be selected to align with the anticipated location of the fraction that is to be collected upon separation. In a preferred embodiment, the sampling window at least partially overlaps with the location of the outlet tube of the blood reservoir or centrifuge bag 226.

In one embodiment, the drive portion is fabricated from a non-transparent material and a path for the beams 884 from the radiation source 884 to the reflector 885 is provided. The path in one preferred embodiment is an opening or hole such as port 154 or 156 (FIG. 14) in the side of the drive portion 881 that creates a path or tunnel through which the beams 884 travel unimpeded. Of course, the opening may be replaced with a path of transparent material to allow the beams to travel to the reflector 885 while also providing a protective cover for the internals of the drive portion 881. A path is also provided downstream of the reflector 885 to allow the beams 884 to travel through the drive portion 881 internals without or with minimal degradation. Again, the path may be an opening or tunnel through the drive portion leading to the portion 202 or be a path created with transparent materials. The beams 884 in these tunnel path embodiments enter the drive portion 881 one time per revolution of the drive portion 881, which provides an acceptable rate of sampling. Alternatively, a reflector 885 may readily be provided that extends circumferentially about the center axis of the drive portion 881 to provide a sampling rate equivalent to the rate of beam 884 transmission. Of course, the positions of the radiation source 882 and the detector 886 may be reversed and the angle of the reflector 885 and transmission of the beams 884 may be altered from those shown to practice the invention.

A further embodiment of an external sensor assembly 840 is provided in FIG. 57. In this embodiment, the radiation source 882 also acts as a radiation detector so there is no need for a separate detector. In this more compact external sensor configuration, the radiation source and detector 882 transmits beams 884 into the rotating drive portion 881 through or over the path in the drive portion 881. The reflector 885 reflects the beams 884 toward the rotor 202 and the centrifuge bag 226 to create a sampling window within the centrifuge bag 226 in which density changes may be monitored. After passing through the centrifuge bag 226 and included fluid sample, the beams 888 strike a second reflector 887 that is positioned within the rotor 202 to reflect the beams 888 back over the same or substantially the same path through the centrifuge bag 226 to again strike the reflector 885. The reflector 885 directs the beams 888 out of the drive portion 881 and back to the radiation source and detector 882 which, in response to the impinging beams 888, transmits a feedback signal to the controller 850 for further processing.

In one embodiment, the beams 884 enter the driving portion 881 once during every revolution of the driving portion 881. The portion 880 is preferably rotating twice for every rotation of the driving portion 881, as discussed in detail above, and hence, the second reflector 887 is aligned to receive the beams 888 only on every other rotation of the driving portion 881. Alternatively, a pair of reflectors 887 may be positioned in the rotor 202 such that the beams 888 may be received and reflected back through the centrifuge bag 226 once for every rotation of the driving portion 881. In yet a further embodiment, the reflector 885 and second reflector 887 may expand partially or fully about the center axis of the centrifuge 20 (with corresponding openings and/or transparent paths in the driving portion 881) to provide a higher sampling rate.

Figure 58:
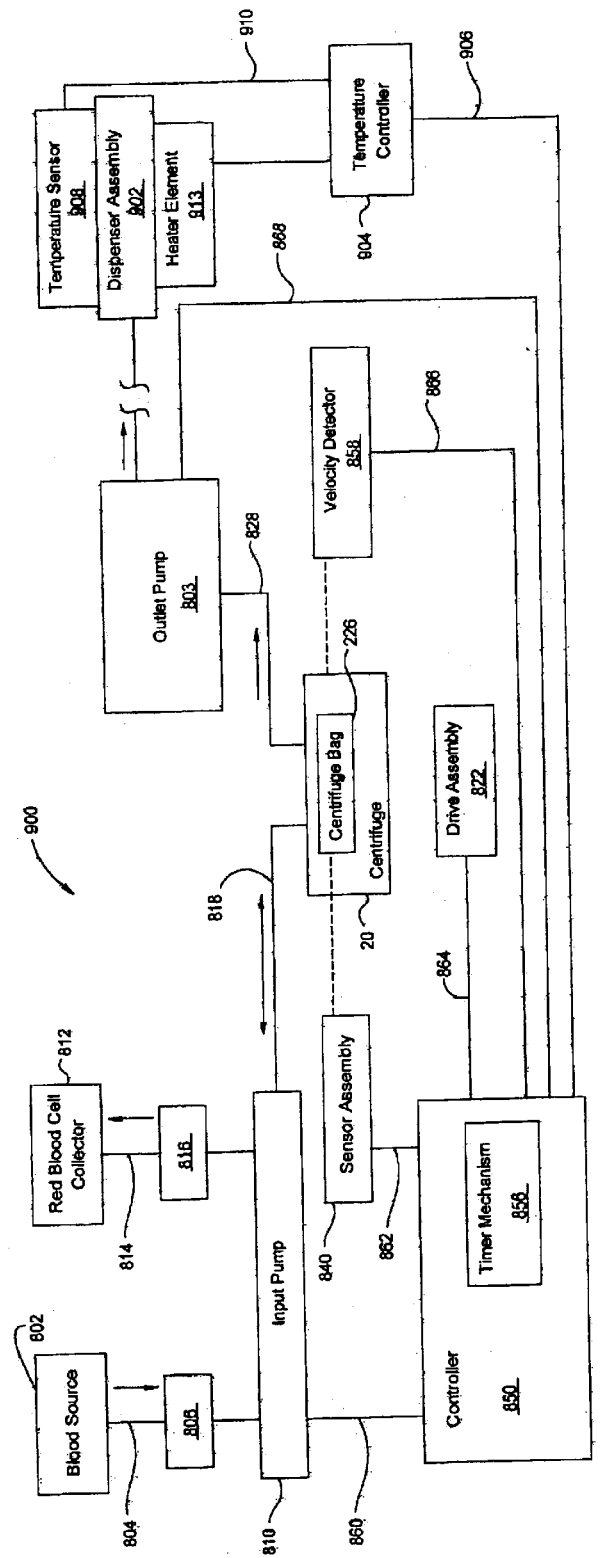
FIG. 58 is a block diagram of a an automated centrifugal processing system, similar to the embodiment of FIG. 47, including components forming a temperature control system for controlling temperatures of separated and processed products.

According to an important feature of the invention, temperature control features are provided in an alternate embodiment of the automated processing system invention 900, as illustrated in FIG. 58. Providing temperature controls within the processing system 900 can take many forms such as controlling the temperature of input fluid samples from the blood source 802, monitoring and controlling the temperature of fluids in the centrifuge bag 226 to facilitate separation processes, and controlling the operating temperature of temperature sensitive components of the processing system 900. These components include but are not limited to, red blood cells, white blood cells, plasma, platelet rich plasma or any of these components mixed with other drugs, proteins or compounds. In a preferred embodiment of the invention, a temperature control system is included in the processing system 900 to heat components removed from the centrifuge bag 226 by the outlet pump 830 to a desired temperature range. For example, when the processing system 900 is utilized in the creation of autologous platelet gel, a dispenser assembly 902 is included in the processing system 900 and includes chambers or syringes for collecting and processing platelet rich plasma drawn from the centrifuge 20. As part of the gel creation process, it is typically desirable to activate the platelets in the harvested platelet rich plasma fraction prior to the use of the gel (e.g., delivery to a patient). The temperature control system is useful in this regard for raising, and for then maintaining, the temperature of the platelets in the dispenser assembly to a predetermined activation temperature range. In one embodiment of the gel creation process, the activation temperature range is 25° C. to 50° C. and preferably 37° C. to 40° C., but it will be understood that differing temperature ranges may readily be utilized to practice the invention depending on the desired activation levels and particular products being processed or created with the processing system 900.

Referring to FIG. 58, the temperature control system of the processing system 900 includes a temperature controller 904 that is communicatively linked to the controller 850 with feedback signal line 906. The controller 850 may be utilized to initially set operating temperature ranges (e.g., an activation temperature range) and communicate these settings over feedback signal line 906 to the temperature controller 904. Alternatively, the temperature controller 904 may include input/output (I/O) devices for accepting the operating temperature ranges from an operator or these ranges may be preset as part of the initial fabrication and assembly of the processing system 900. The temperature controller 904 may comprise an electronic control circuit allowing linear, proportional, or other control over temperatures and heater elements and the like. In a preferred embodiment, the temperature controller 904 includes a microprocessor for calculating sensed temperatures, memory for storing temperature and control algorithms and programs, and I/O portions for receiving feedback signals from thermo sensors and for generating and transmitting control signals to various temperature control devices (e.g., resistive heat elements, fan rotors, and other devices well-known to those skilled in the heating and cooling arts).

As illustrated, a temperature sensor 908 comprising one or more temperature sensing elements is provided to sense the temperature of the dispenser assembly 902 and to provide a corresponding temperature feedback signal to the temperature controller 904 over signal line 910 (such as an electric signal proportional to sensed temperature changes). The temperature sensor 908 may be any temperature sensitive device useful for sensing temperature and, in response, generating a feedback signal useful by the temperature controller 904, such as a thermistor, thermocouple, and the like. In a preferred embodiment, the temperature sensor 908 is positioned within the dispenser assembly 902 to be in heat transferring or heat sensing contact with the syringes or other chambers containing the separated product which is to be activated. In this manner, the temperature controller 904 is able to better monitor whether the temperature of the relevant chambers within the dispenser assembly 902 is within the desired activation temperature range.

To maintain the chambers of the dispenser assembly 902 within a temperature range, a heater element 913 is included in the temperature control system and is selectively operable by the temperature controller 904 such as by operation of a power source based on signals received from the temperature sensor 908. The heater element 913 may comprise any number of devices useful for heating an object such as the chambers of the dispenser assembly 902, such as a fluid heat exchanger with tubing in heat exchange contact with the chambers. In a preferred example, but not as a limitation, electrical resistance-type heaters comprising coils, plates, and the like are utilized as part of the heater element 913. Preferably, in this embodiment, the resistive portions of the heater element 913 would be formed into a shape that conforms to the shape of the exterior portion of the chambers of the dispenser assembly 902 to provide efficient heat transfer but preferably also allow for insertion and removal of the chambers of the dispenser assembly 902. During operation of the separation system 900, the temperature controller 904 is configured to receive an operating temperature range, to receive and process temperature feedback signals from the temperature sensor 908, and in response, to selectively operate the heater element 913 to first raise the temperature of the chambers of the dispenser assembly 902 to a temperature within the operating temperature range and to second maintain the sensed temperature within the operating range.

For example, a desired operating range for activating a gel or manipulating other cellular components and their reactions onto themselves or with agents may be provided as a set point temperature (or desired activation temperature) with a tolerance provided on either side of this set point temperature. The temperature controller 904, in this example, may operate the heater element 913 to raise the temperature of the chambers of the dispenser assembly 902 to a temperature above the set point temperature but below the upper tolerance temperature at which point the heater element 913 may be shut off by the temperature controller 904. When the temperature sensed by the temperature sensor 908 drops below the set point temperature but above the lower tolerance temperature, the temperature controller 904 operates the heater element 913 to again raise the sensed temperature to above the set point temperature but below the upper tolerance temperature. In this manner, the temperature controller 904 effectively maintains the temperature of the chambers in the dispenser assembly 902 within a desired activation temperature range (which, of course, may be a very small range that approximates a single set temperature). In one embodiment, the temperature controller is or operates as a proportional integral derivative (PID) temperature controller to provide enhanced temperature control with smaller peaks and abrupt changes in the temperature produced by the heater element 913. Additionally, the temperature controller 904 may include visual indicators (such as LEDs) to indicate when the sensed temperature is within a set operating range and/or audio alarms to indicate when the sensed temperature is outside the set operating range.

In another embodiment, the heater element 913 is configured to operate at more than one setting such that it may be operated throughout operation of the processing system 900 and is not shut off. For example, the heater element 913 may have a lower setting designed to maintain the chambers of the dispenser assembly 902 at the lower end of the operating range (e.g., acceptable activation temperature range) with higher settings that provide heating that brings the chambers up to higher temperatures within the set operating range. In another embodiment, the heater element 913 is configured to heat up at selectable rates (e.g., change in temperature per unit of time) to enhance the activation or other processing of separated liquids in the dispenser assembly 902. This feature provides the temperature controller 904 with control over the heating rate provided by the heater element 913.

Figure 59:
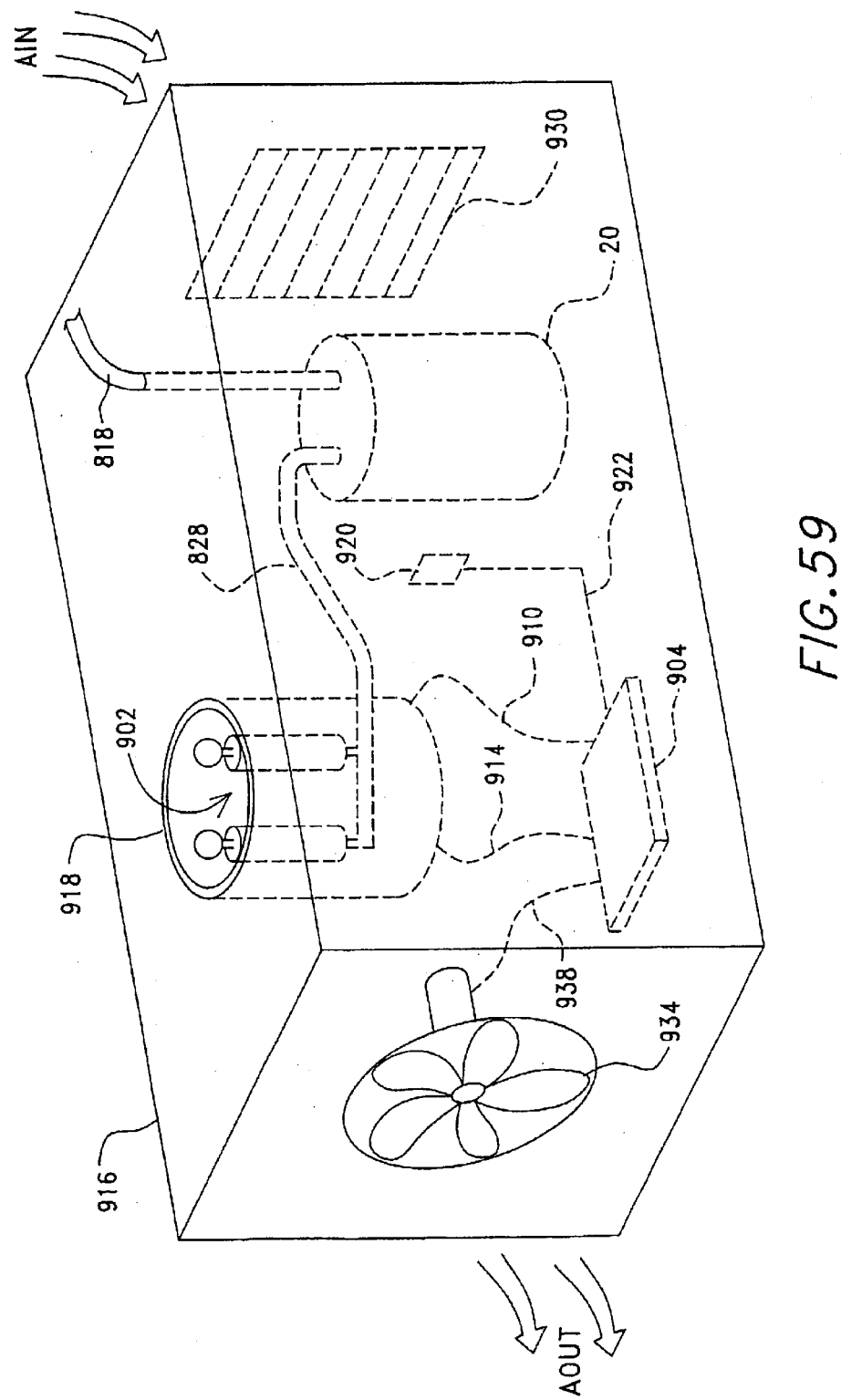
FIG. 59 is a perspective view of components of the temperature control system of FIG. 58.

As discussed previously, the invention provides features that combine to provide a compact separation system that is particularly adapted for onsite or field use in hospitals and similar environments where space is limited. FIG. 59 illustrates one preferred arrangement of the centrifugal processing system 900 of FIG. 58 that provides a compact profile or footprint while facilitating the inclusion of a temperature control system. An enclosure 916 is included as part of the temperature control system to provide structural support and protection for the components of the temperature control system. The enclosure 916 may be fabricated from a number of structural materials, such as plastic. The enclosure 916 supports a heater housing 918 that is configured to allow insertion and removal of the chambers and other elements of the dispenser assembly 902. The heater housing 918 has a wall that contains the heater element 913 (not shown in FIG. 59) which is connected via control line 914 to the temperature controller 904. The temperature sensor 908 (not shown in FIG. 59) is also positioned within the heater housing 918, and as discussed with reference to FIG. 58, is positioned relative to the chambers of the dispenser assembly 902 to sense the temperature of the chambers, and the contained fluid, during operation of the system 900. A temperature feedback signal is transmitted by the temperature sensor 908 over line 910 to temperature controller 904, which responds by selectively operating the heater element 913 to maintain the temperature within the heater housing 918 within a selected operating range.

Because the separation system 900 includes temperature sensitive components, such as the controller 850, the temperature control system preferably is configured to monitor and control the temperature within the enclosure 916. As illustrated, a temperature sensor 920 is included to sense the ambient temperature within the enclosure 916 and to transmit a feedback signal over line 922 to temperature controller 904. An air inlet 930, such as a louver, is provided in the enclosure 916 to allow air, $A_{IN}$, to be drawn into and through the enclosure 916 to remove heated air and maintain the temperature within the enclosure 916 at an acceptable ambient temperature. To circulate the cooling air, a fan 934 is provided to pull the air, $A_{IN}$, into the enclosure 916 and to discharge hotter air, $A_{OUT}$, out of the enclosure 916. The fan 934 is selectively operable by the temperature controller 904 via control signals over line 938. The size or rating of the fan 934 may vary in embodiments of the invention and is preferably selected based on the volume of the enclosure 916, the components positioned within the enclosure 916 (e.g., the quantity of heat generated by the separation system 900 components), the desired ambient temperature for the enclosure 916, and other cooling design factors.

Figure 60:
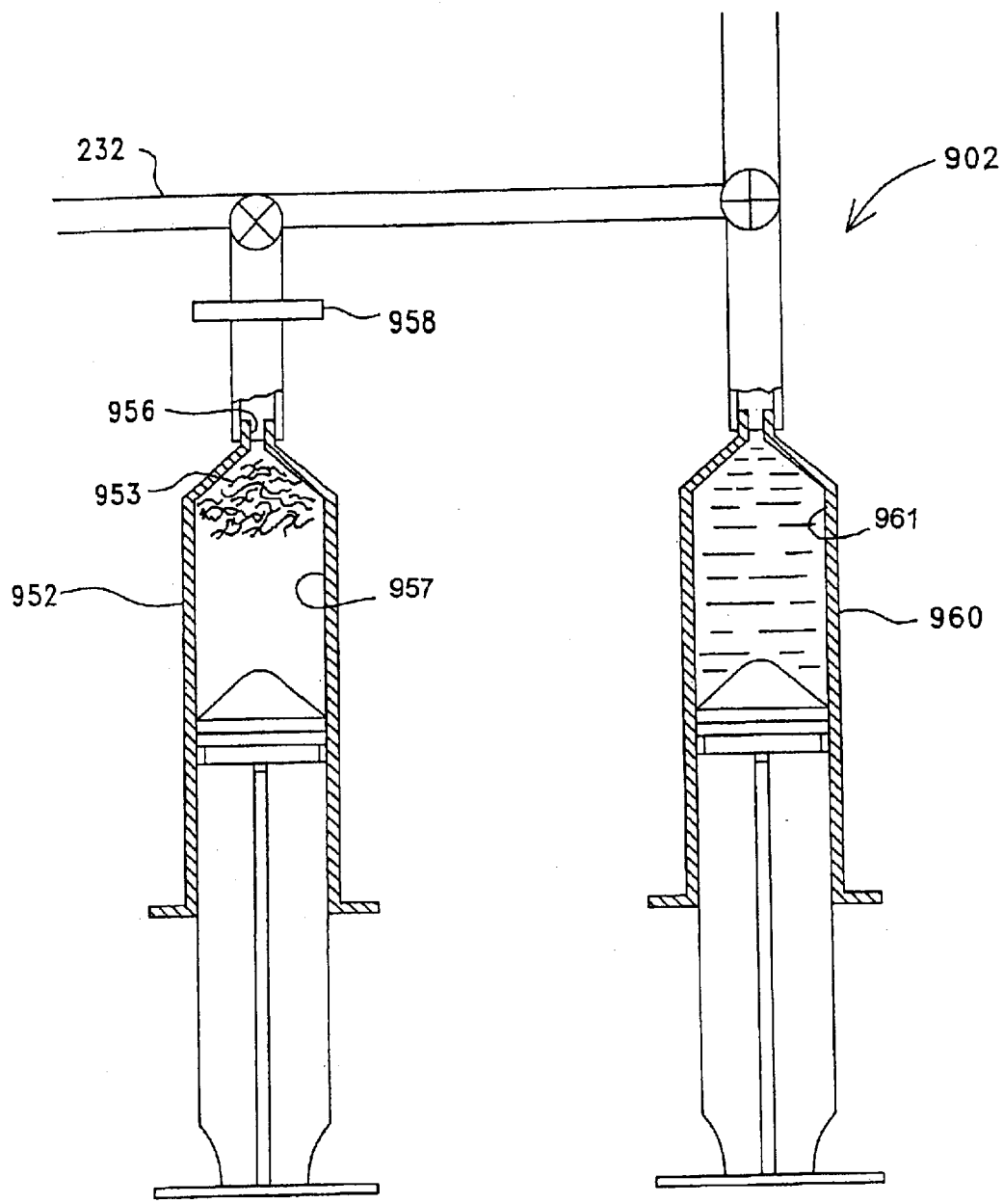
FIG. 60 is schematic and sectional view of the dispenser of the present invention.

In an alternate embodiment of the present invention a dispenser 902, as shown in FIG. 60, is provided, for manipulating the cellular fraction which has been isolated and collected via outlet lumen 232. In general, the present invention relates to a dispenser 902 which allows for a manual or automated manipulation of a two-phase method for forming an autologous platelet gel 970 composition wherein all of the blood components for the platelet gel 970 are derived from a patient to whom the platelet gel 970 will be applied.

The methods of the present invention for preparing an autologous platelet gel 970 composition, discussed in further detail below, are represented in the flow diagrams depicted in FIGS. 61–63. As discussed previously, the methods of the present invention begins by forming anticoagulated whole blood 396 which is achieved by collecting a patient's whole blood 394 in a source container 398 having an anticoagulation agent, such as sodium citrate (citrate) or heparin. Preferably, the whole blood 394 is collected and mixed with a 3.8% solution of sodium citrate (referred to herein as "citrate collection medium") specifically in a 9:1 ratio of blood to citrate collection medium. A 3.8% solution of sodium citrate is prepared by adding 3.8 grams of sodium citrate per 100 ml of water. While a 3.8% sodium citrate collection medium is that which is frequently used to collect and preserve blood, the person skilled in this art will recognize that the ratio of sodium citrate to whole blood could be in the range of about 10.9–12.9% mMol final concentration.

Figure 61:
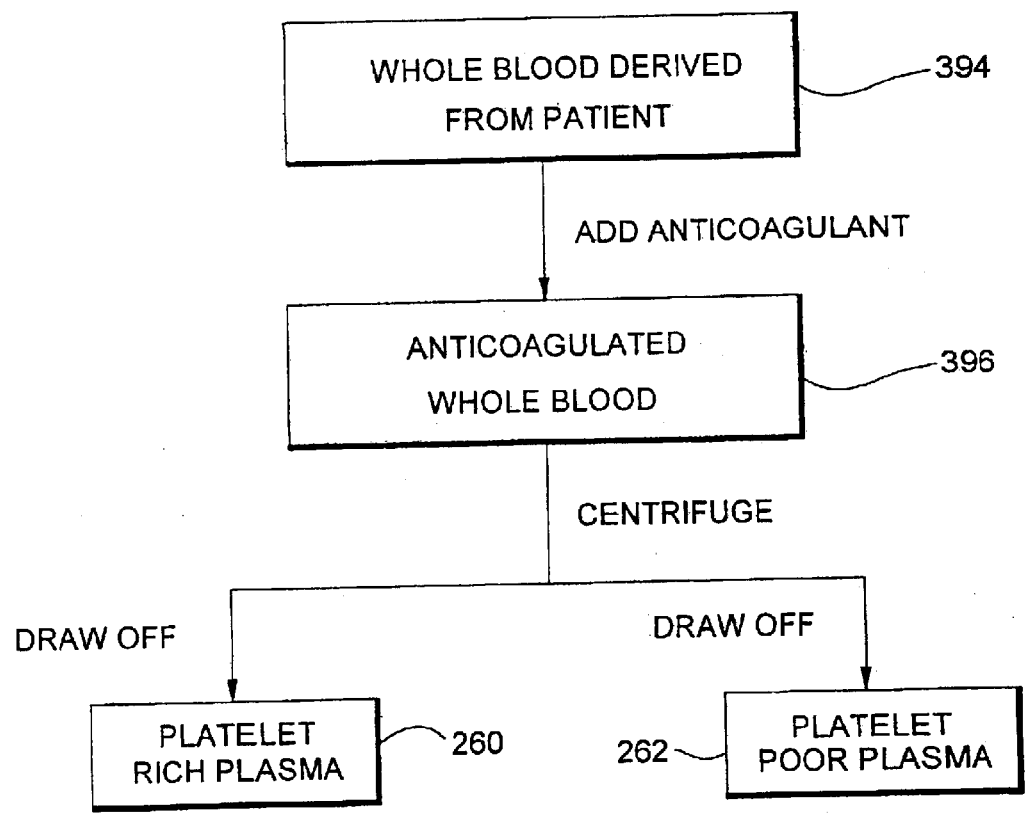
FIG. 61 is a flow diagram representing the method for isolating platelet rich plasma and platelet poor plasma for use in preparing a platelet gel of the present invention.

First, as discussed in detail previously and depicted in FIG. 61, platelet rich plasma 260 and/or platelet poor plasma 262 are formed by centrifuging a quantity of anticoagulated whole blood 396 that was previously drawn from the patient. The platelet rich plasma 260 is first drawn from the centrifuge bag 226 and into collection chamber 400. Collection chamber 400 is preferably a syringe, but any container that will not contact activate the collected fraction is acceptable. The platelet rich plasma 260 can be pumped via outlet pump 803 (FIG. 53) into a collection chamber 400 or the desired fraction can be drawn directly into dispenser 902.

Figure 62:
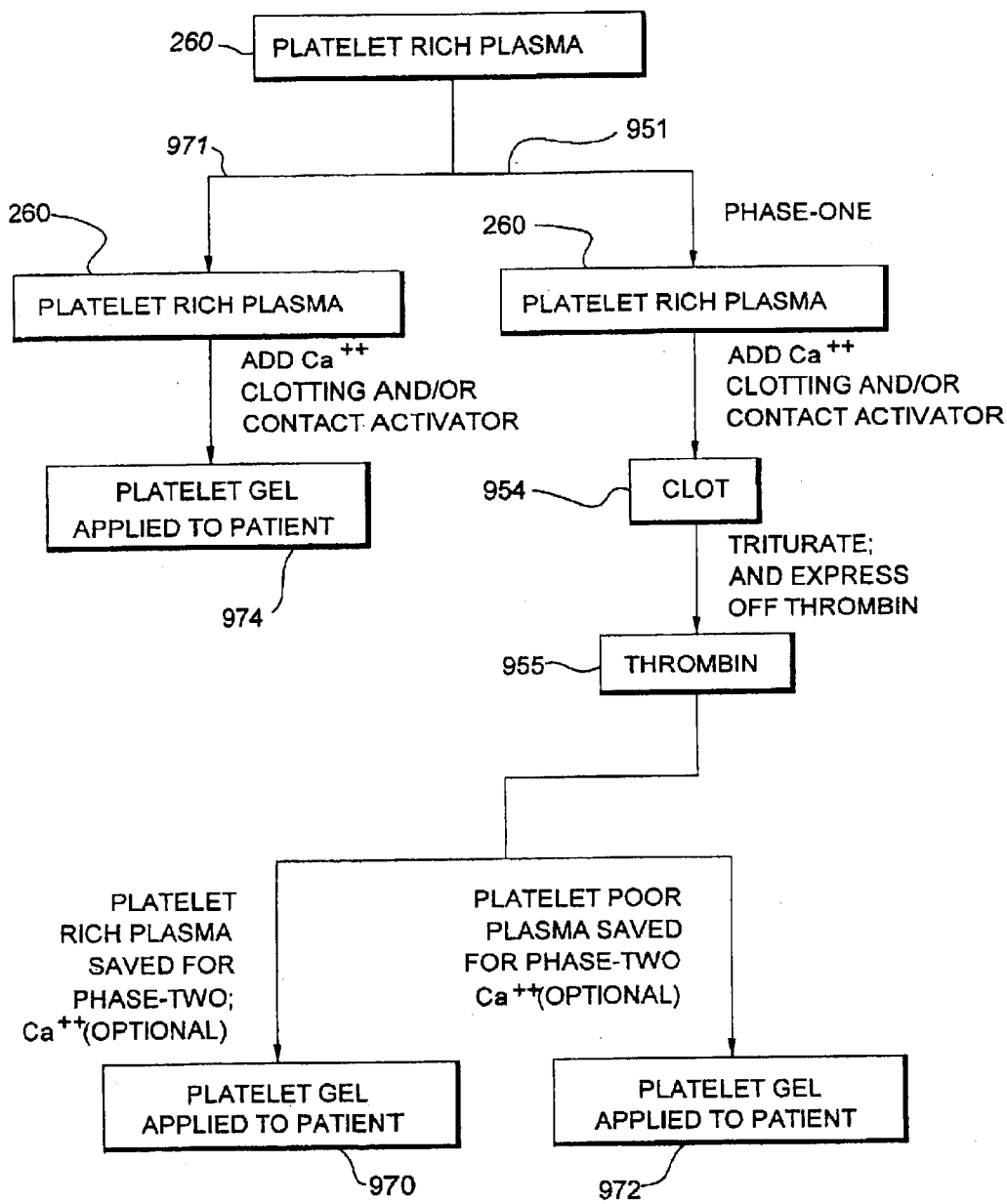
FIG. 62 is a flow diagram representing the final portion of the method for preparing a platelet gel of the present invention using platelet rich plasma as a starting material.

In the preferred embodiment, depicted in FIG. 62 according to route 951, the platelet rich plasma 260, in centrifuge bag 226, is divided into two portions and stored in vessels 952 and 960. The first portion is approximately ¼ to ½ of the total volume of platelet rich plasma 260 and is utilized in phase-one to prepare the thrombin, while the second portion of platelet rich plasma 260 is utilized in phase-two vessel 960. Once the platelet rich plasma 260 or alternatively the platelet poor plasma 262 (shown in FIG. 61) is obtained, the preferred methods to obtain thrombin and then produce the platelet gel compositions in an expedited manner, that is, in less than three minutes, are detailed diagrammatically in routes 951 or 981, shown in FIGS. 62 and 63, respectively and discussed in detail below. If, however, a longer clotting time, that is, in a range of two to eight minutes, is desirous the method to obtain the platelet gel composition of the present invention can proceed along the routes 971 and 987, which are also detailed diagrammatically in FIGS. 63 and 63, respectively and discussed in detail below.

Phase-one according to the preferred embodiment (FIG. 62) begins by restoring the clot-forming process. To accomplish this, an agent (restoration agent) capable of reversing the effects of the anticoagulation agent is added back into the first portion of the platelet rich plasma 260 stored in vessel 952. Preferably, the restoration agent can be vessel 952 itself or the restoration agent is contained within vessel 952 prior to the introduction of platelet rich plasma 260; however, the restoration agent may also be introduced later. It is furthermore preferable that the contact activator be a material such as but not limited to glass wool 953 or silica, aluminum, diatomaceous earth, kaolin, etc., or non-wettable surfaces such as plastic, siliconized glass, etc. Chemical activators, such as kaolin, can also be used to speed up the clotting time; however, their subsequent removal would also be necessary. In the preferred embodiment, a plastic syringe is the preferred container used to collect the desired fraction. In the presently preferred embodiment of the invention, the reversal of the anticoagulant is accomplished using calcium chloride. However, any substance which is known or found to be functionally equivalent to calcium chloride, such as, calcium gluconate or calcium carbonate, in restoring the coagulation activity of citrated blood may be used in the practice of the present invention. Thus, although calcium chloride is the presently preferred calcium salt for use in the invention, any calcium salt which functions in a similar manner to calcium chloride may be used in the invention. Similarly, although many blood coagulation reactions are currently believed to require calcium ions as cofactors, any substance which is known or subsequently found to be functionally equivalent to calcium in facilitating these coagulation reactions may be used, either individually or in combination with calcium, in the practice of the present invention. If the anticoagulation agent used was heparin, then heparinase or any other suitable anticoagulant reversing compound would be used to reverse the effect of the anticoagulation agent. The concentration of the restoration agent used to reverse the anticoagulation will depend in part, upon the concentration of the anticoagulation agent in the platelet rich plasma 260 and the stoichiometry of the chelating and coagulation reactions. However, the concentration of the restoration agent used to reverse the anticoagulation must be sufficient to achieve clot formation.

Upon restoration of the platelet rich plasma 260 as shown in FIG. 62, a clot 954 will naturally form. The resulting clot 954 is then triturated by squeezing the clot 954 through glass wool 953 which serves not only as a contact activator but also as a filter, thus expressing thrombin 955. Alternatively, or in addition a filter 958 having a large micron pore size thereby allowing the removal of clot debris and any activator or solids that are present. Filter 958 is positioned at the outlet 956 of vessel 952. In the preferred embodiment, the thrombin 955 is then mixed with the second portion of platelet rich plasma (PRP) 260 contained within vessel 960 to form the platelet gel composition 970 of the present invention in less than three minutes and in quantities sufficient for clinical use.

Other additives can be added to the above-described process to increase the concentration of thrombin formed by the intrinsic pathway or the extrinsic pathway.

As discussed in detail above, restoring the clotting cascade function of citrated plasma by addition of calcium chloride and exposure to an activating agent such as glass wool can generate autologous thrombin. The yield of autologous thrombin by this method however, may be low due to incomplete conversion of prothrombin and the inactivation of generated thrombin by fibrin and antithrombin III. The addition of modifying agents, such as epsilon aminocaproic acid, to the plasma may improve the yield by reducing the amount of thrombin neutralization. The greatest improvement in thrombin yield, however, will be achieved by providing a thromboplastic material upon which the necessary clotting factors will assemble to maximize the rate of prothrombin conversion. The activated platelet membrane provides such a stimulant surface and also enriches the necessary factor V activity by secreting additional factor V during platelet degranulation. The addition of exogenous lipoprotein and/or thromboplastic material to the plasma environment may also serve to maximize the thrombin generation by activation of both intrinsic and extrinsic clotting cascades. Additional amplification of autologous thrombin generation may also be attained by pretreatment of PRP and/or PPP to block or remove both antithrombin-III and fibrinogen prior to conversion of prothrombin to thrombin. Such modification may be attained by use of appropriate adsorptive agents, antibodies or precipitating reagents.

In an alternative embodiment, thrombin 955 is mixed with the platelet poor plasma 262 of phase-two thereby forming the autologous platelet gel composition 972 of the present invention in less than three minutes.

A third embodiment of the present invention, route 971, shown in FIG. 62, contemplates collecting the original quantity of platelet rich plasma (PRP) 260 derived from the anticoagulated whole blood 396 in a container, having a wettable surface, such as glass. The platelet rich plasma 260 is then recalcified and the platelet gel composition 974 forms. The desired platelet gel composition 974 will require approximately two to eight minutes to form as opposed to less than a three minute formation as was described in the preferred embodiment.

Figure 63:
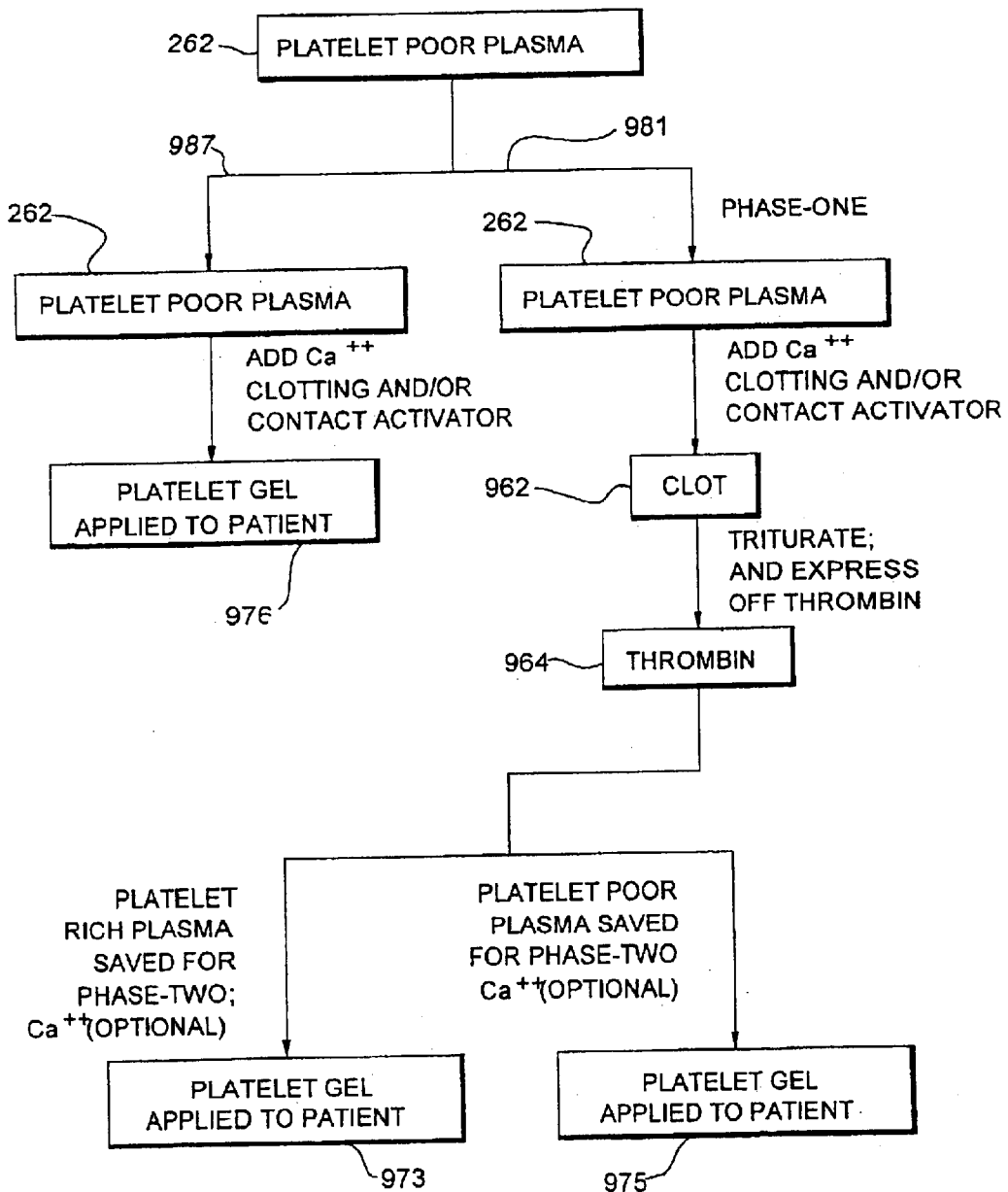
FIG. 63 is a flow diagram representing the final portion of the method for preparing a platelet gel of the present invention using platelet poor plasma as a starting material.

In the fourth embodiment depicted diagrammatically by route 981 in FIG. 63, the platelet poor plasma 262, rather then the platelet rich plasma 260, is divided into two portions, as discussed previously in the preferred embodiment. The first portion, used in phase-one, which is approximately ¼ to ½ the original volume is stored in a vessel 952 having a wettable surface, then the restoration agent, preferably calcium chloride, is added directly to the platelet poor plasma 262. Surface activation of the restored platelet poor plasma 262 occurs as result of the vessel's surface and/or the glass wool 953 or other surface or chemical activators and a clot 962 thus forms. The resulting clot 962 is triturated, as described previously, and the thrombin 955 is collected. Thrombin 955 is then mixed with the platelet rich plasma 260 of phase-two thereby forming the platelet gel sealant composition 973.

In the fifth embodiment, thrombin 955 is mixed with the platelet poor plasma 262 of phase-two thereby forming the platelet gel composition 975 in less than three minutes.

The sixth embodiment follows route 987, shown in FIG. 63 wherein the original quantity of platelet poor plasma 262 is collected in a container having a wettable surface, such as glass. The platelet poor plasma 262 is then recalcified and the platelet gel composition forms.

The tensile strength of the platelet gel compositions of the present invention can be effected by the addition of calcium ions. Consequently, if a stronger bioadhesive sealant composition is desired using the methods discussed above and disclosed in routes 951 and 981, in FIGS. 62 and 62, respectively, more calcium ions may be added at the time the serum is introduced into the platelet rich plasma 260 or the platelet poor plasma 262. Alternatively, if the method of preparing the platelet gel compositions follows routes 971 and 987, depicted in FIGS. 62 and 63, respectively, then calcium ions may be introduced directly into the platelet rich plasma 260 or the platelet poor plasma 262 and the platelet gel compositions 974 and 976, respectively, will form.

As discussed in further detail below, the time period necessary for the formation of the platelet gel composition of the present invention is dependent on the quantity of serum added. A 1:4, 1:2 and 3:4 ratio of serum to platelet rich plasma or platelet poor plasma results in the formation of the platelet gel composition in approximately 90, 55 and 30 seconds, respectively. Furthermore, due to the fact that thrombin is autocatalytic, it is important that the serum be used within five hours of preparation, preferably within two hours and ideally immediately. Alternatively, the serum can be chilled or frozen indefinitely.

The platelet gel compositions of this invention may be used for sealing a surgical wound by applying to the wound a suitable amount platelet rich plasma or platelet poor plasma. Moreover, due to the fact that the platelet gel compositions of the present invention have been prepared solely from blood components derived from the patient that is to receive the platelet gel there is a zero probability of introducing a new blood transmitted disease to the patient. The methods of the present invention may be further modified so that the formed platelet gel composition functions not only as a haemostatic agent, but also as an adjunct to wound healing and as a matrix for delivery of drugs and proteins with other biologic activities. For example, it is well known that fibrin glue has a great affinity to bind bone fragments which is useful in bone reconstruction, as in plastic surgery or the repair of major bone breaks. Consequently, in keeping with the autologous nature of the platelet gel composition of the present invention autologous bone from a patient can be ground or made into powder or the like, and mixed into the platelet rich plasma obtained in phase-two of the methods of the present invention. Autologous thrombin is then mixed in with the platelet rich plasma and bone fragments in an amount sufficient to allow the resulting gel to be applied to the desired locale where it congeals. Other materials that may be utilized are, but not limited to, gelatin collagen, degradable polymers, hyaluronic acid, carbohydrates and starches.

In instances where the desired platelet gel composition of the present invention is to further function as a delivery device of drugs and proteins with other biologic activities the method of the present invention may be modified as follows. Prior to adding the thrombin, obtained in phase-one, to the platelet rich plasma of phase-two a wide variety of drugs and proteins with other biologic activities may be added to the platelet rich plasma of phase-two. Examples of the agents to be added to the platelet rich plasma prior to the addition of the serum include, but are not limited to, analgesic compounds, such as Lidocaine, antibacterial compounds, including bactericidal and bacteriostatic compounds, antibiotics (e.g., adriamycin, erythromycin, gentimycin, penicillin, tobramycin), antifungal compounds, anti-inflammatories, antiparasitic compounds, antiviral compounds, anticancer compounds, such as paclitaxol enzymes, enzyme inhibitors, glycoproteins, growth factors (e.g. lymphokines, cytokines), hormones, steroids, glucocorticosteroids, immunomodulators, immunoglobulins, minerals, neuroleptics, proteins, peptides, lipoproteins, tumoricidal compounds, tumorstatic compounds, toxins and vitamins (e.g., Vitamin A, Vitamin E, Vitamin B, Vitamin C, Vitamin D, or derivatives thereof). It is also envisioned that selected fragments, portions, derivatives, or analogues of some or all of the above may be used.

A number of different medical apparatuses and testing methods exist for measuring and determining coagulation and coagulation-related activities of blood. These apparatuses and methods can be used to assist in determining the optimal formulation of activator, that is, thrombin, calcium and plasma necessary to form the platelet gel composition of the present invention. Some of the more successful techniques of evaluating blood clotting and coagulation are the plunger techniques illustrated by U.S. Pat. No. 4,599,219 to Cooper et al., U.S. Pat. No. 4,752,449 to Jackson et al., and U.S. Pat. No. 5,174,961 to Smith, all of which are assigned to the assignee of the present invention, and all of which are incorporated herein by reference.

Automated apparatuses employing the plunger technique for measuring and detecting coagulation and coagulation-related activities generally comprise a plunger sensor cartridge or cartridges and a microprocessor controlled apparatus into which the cartridge is inserted. The apparatus acts upon the cartridge and the blood sample placed therein to induce and detect the coagulation-related event. The cartridge includes a plurality of test cells, each of which is defined by a tube-like member having an upper reaction chamber where a plunger assembly is located and where the analytical test is carried out, and a reagent chamber which contains a reagent or reagents. For an activated clotting time (ACT) test, for example, the reagents include an activation reagent to activate coagulation of the blood. A plug member seals the bottom of a reagent chamber. When the test commences, the contents of the reagent chamber are forced into the reaction chamber to be mixed with the sample of fluid, usually human blood or its components. An actuator, which is a part of the apparatus, lifts the plunger assembly and lowers it, thereby reciprocating the plunger assembly through the pool of fluid in the reaction chamber. The plunger assembly descends by the force of gravity, resisted by a property of the fluid in the reaction chamber, such as its viscosity. When the property of the sample changes in a predetermined manner as a result of the onset or occurrence of a coagulation-related activity, the descent rate of the plunger assembly there through is changed. Upon a sufficient change in the descent rate, the coagulation-related activity is detected and indicated by the apparatus.

Figure 64:
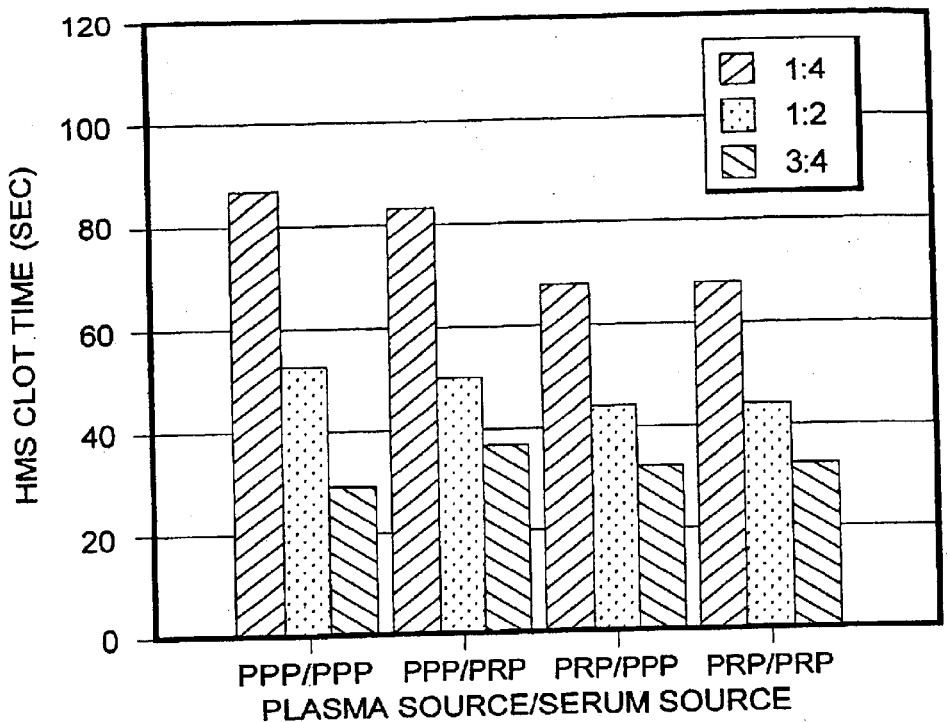
FIG. 64 is a graphic representation of the effect that the serum-to-plasma ratio has on clotting times.
Figure 65:
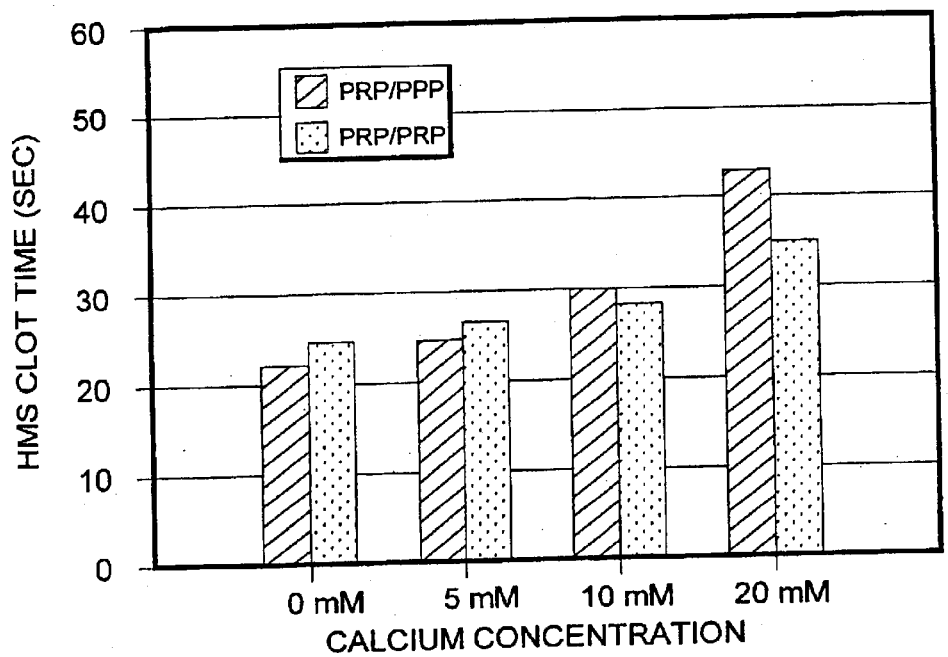
FIG. 65 graphically represents the effect of calcium addition on the clotting times of platelet rich plasma and platelet poor plasma.
Figure 66:
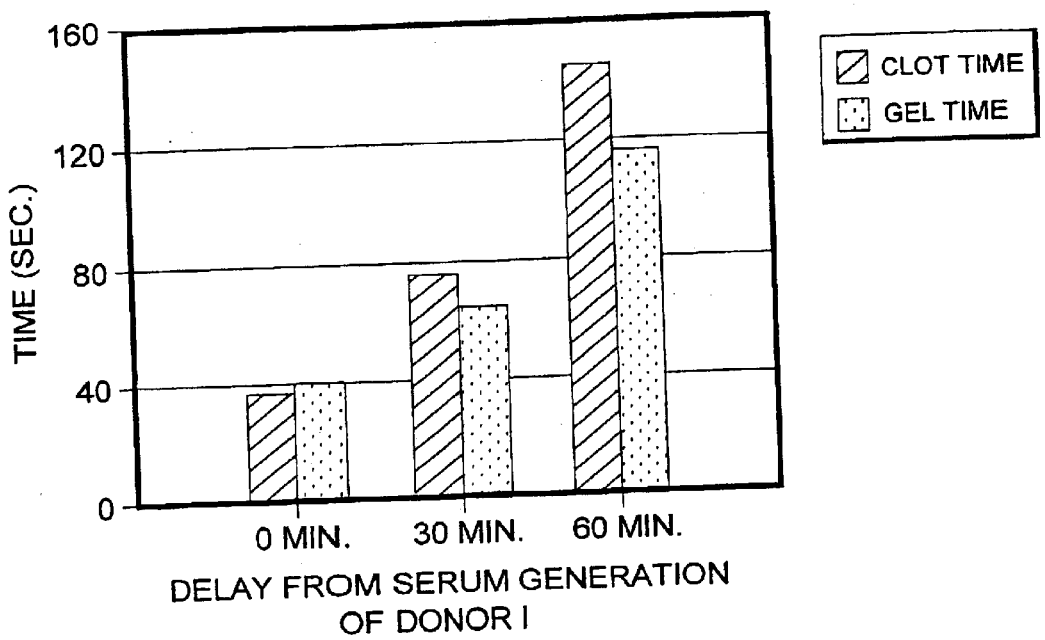
FIG. 66 is a graphic representation of the relationship between clotting time and actual gel time using blood drawn from a donor.
Figure 67:
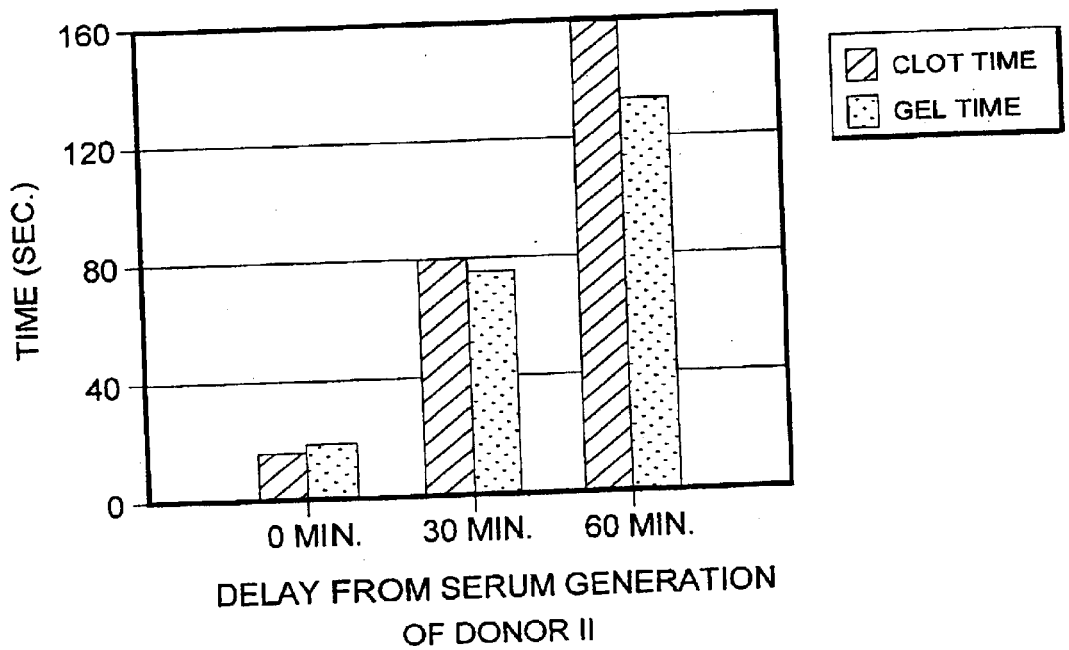
FIG. 67 is a graphic representation of the relationship between clotting time and actual gel time using blood drawn from a donor.
Figure 68:
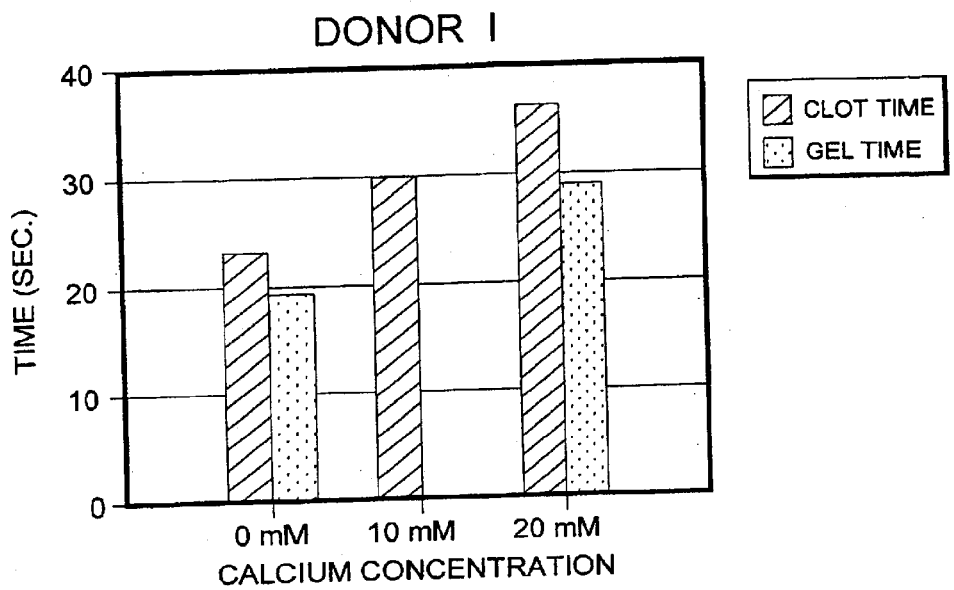
FIG. 68 graphically represents the effect of calcium addition on clotting times and gel times using blood drawn from a donor.
Figure 69:
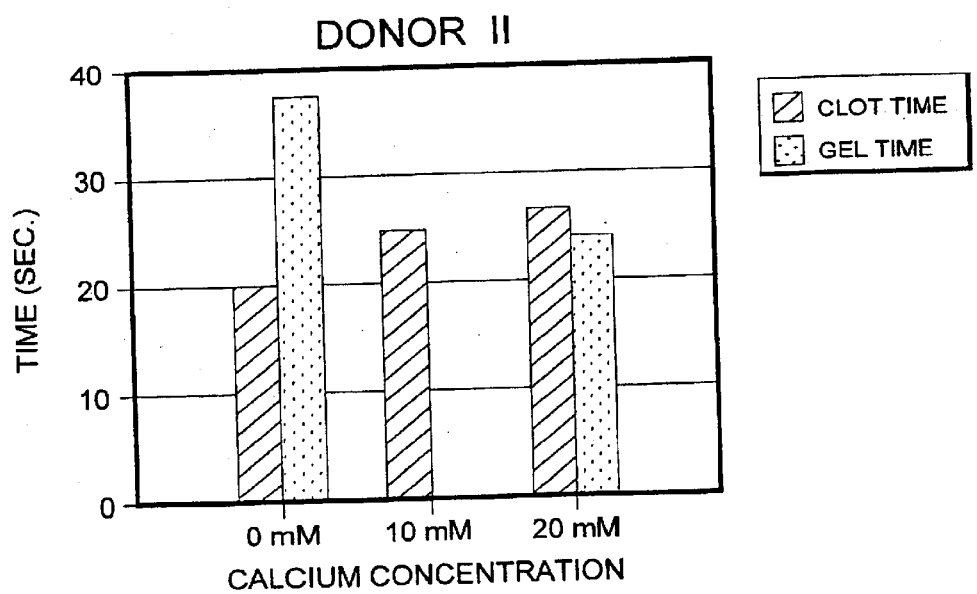
FIG. 69 graphically represents the effect of calcium addition on clotting times and gel times using blood drawn from a donor.

Using the methods discussed above, cartridges were assembled with serum obtained from either platelet rich plasma or platelet poor plasma, and $CaCl_2$ in the reagent chambers. Clotting time tests were performed by the automated process with either platelet rich plasma (PRP) or platelet poor plasma (PPP) dispersed into the reaction chambers of the cartridges. In the first experiment, the results of which are represented in FIG. 64, the amount of serum, the type of plasma from which the serum was derived, and the type of plasma the serum was mixed with were tested to determine the shortest clotting times. The ratios of serum to platelet rich plasma or platelet poor plasma that were studied included 1:4, 1:2, and 3:4. In the second set of experiments, the results of which are represented in FIGS. 66 and 67, the actual gel time for the platelet gel of the present invention was compared to the clotting time in the cartridge, wherein there is a 0, 30, or 60 minute delay of adding the serum from its generation. The third set of experiments, the results of which are represented in FIGS. 68 and 69, studied the effect of calcium addition on actual gel time versus clotting time in the cartridge. The final set of experiments, the results of which are represented in FIG. 65, studied the effect of adding calcium on clotting times.

Although clotting times varied among donors, comparisons of clotting times for individual donors show significant effects of the serum to plasma ratio and the calcium concentration. For all donors, the shortest clotting times occurred for the 3:4 ratio, with clotting times that were 47% shorter than those for the 1:4 ratio. Although the difference in clotting times for the 3:4 ratio and the 1:2 ratio was not statistically significant, the clotting times were consistently shorter using the 3:4 ratio for all donors. These results demonstrate that clotting times may be shortened by increasing the serum to platelet rich plasma ratio. Similarly, clotting times were significantly affected by the amount of calcium added, with the shortest clotting times obtained when no calcium was added, suggesting that the serum contained levels of calcium that were sufficient to recalcify the citrated platelet rich plasma. Preliminary results from the scale-up experiments suggest that experimental clotting times in the cartridges correlate with actual gel times.

The invention is further illustrated by the following non-limited examples. All scientific and technical terms have the meanings as understood by one with ordinary skill in the art. The specific examples which follow illustrate the methods in which the bioadhesive sealant compositions of the present invention may be prepared in a clinical setting and are not to be construed as limiting the invention in sphere or scope. The methods may be adapted to variation in order to produce compositions embraced by this invention but not specifically disclosed. Further, variations of the methods to produce the same compositions in somewhat different fashion will be evident to one skilled in the art.

EXAMPLES

The examples herein are meant to exemplify the various aspects of carrying out the invention and are not intended to limit the invention in any way.

Example 1

Preparation of Bioadhesive Sealant Composition Using Platelet Rich Plasma and Serum 6 cc's of platelet rich plasma are drawn into receiving chamber 961 and 3 cc's per PRP or PPP are drawn into receiving chamber 957 which further contains 0.33 cc's of 10% calcium chloride and glass wool. Clotting of the contents will occur in two to eight minutes in receiving chamber 957. The clot is then squeezed through optional filter 958 and the serum, produced therefrom, is added to the platelet rich plasma contained in receiving chamber 961 by either mixing or spraying the two components. The platelet rich plasma and the serum will gel within approximately three minutes.

The application of the gel using the syringe-type devices 902 as described above maybe less than desirable for may applications. Consequently, in an alternate embodiment the inactive blood component and thrombin can be mixed and/or injected into a mold having a desired geometric shape. The mold may be constructed of a material having a wettable surface, such as, but not limited to plastic. In particular, platelet gel of the present invention may be used to temporarily fill, cavities such as but not limited to holes left in the gum from tooth extraction and/or holes left in tissue or bone as a result of injury or surgical procedures. The present invention provides a simpler way of introducing platelet gel for specific uses, by providing that the platelet gel be pre-shaped or molded into a beneficial shape prior to being inserted into a cavity. In the case of tooth extraction the platelet gel may be shaped so as to achieve a basic conical shape. Other shapes such as, but not limited to rods, and rectangles are contemplated by this invention. The ability to cause the gel to be more, or less, solid and thus malleable may be achieved during the activation sequence of the gel formation.

The foregoing description is considered as illustrative only of the principles of the invention. Furthermore, since numerous modifications and changes will readily occur to those skilled in the art, it is not desired to limit the invention to the exact construction and processes shown as described above. Accordingly, all suitable modifications and equivalents may be resorted to falling within the scope of the invention as defined by the claims which follow.

The foregoing description is considered as illustrative only of the principles of the invention. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. Furthermore, since a number of modifications and changes will readily will readily occur to those skilled in the art, it is not desired to limit the invention to the exact construction and process shown described above. Accordingly, all suitable modifications and equivalents may be resorted to falling within the scope of the invention as defined by the claims which follow.

The embodiments of the invention in which an exclusive property or privilege is claimed are defined as follows:

1. A flexible, disposable centrifuge bag for receiving and holding a fluid sample, comprising:

an inlet tube having a distal end positioned at a first radial distance from the center axis of said centrifuge bag and an outlet tube having a distal end positioned at a second radial distance from the center axis of said centrifuge bag, said first radial distance being greater than said second radial distance; and upper and lower flexible sheets, said sheets having doughnut shaped configurations, inner perimeters defining a central core of said centrifuge bag, and outer perimeters, wherein said upper and lower sheets are superimposed and completely sealed together at their outer perimeters thereby defining the outer perimeter of said centrifuge bag, and wherein said tubes are sandwiched between said upper and lower sheets and extend from the central core of said centrifuge bag, whereby when said upper and lower sheets are sealed together at their inner perimeters said tubes are sealed between said upper and lower sheets at the inner perimeter.

2. The centrifuge bag of claim 1, wherein said inlet tube and said outlet tube are in fluid communication at their proximal ends with a dual lumen tubing.

3. The centrifuge bag of claim 2, wherein said dual lumen tubing comprises an inlet lumen fluidly connected to said inlet tube.

4. The centrifuge bag of claim 2, wherein said dual lumen tubing comprises an outlet lumen fluidly connected to said outlet tube.

5. The centrifuge bag of claim 1, wherein said outlet tube is fluidly connected at its distal end to a bent fitting.

6. The centrifuge bag of claim 5, wherein said bent fitting has a configuration selected from the group consisting of a T shape, a curved T shape, a J shape, or an L shape.

7. The centrifuge bag of claim 1, comprising an inlet tube and two or more outlet tubes.

8. The centrifuge bag of claim 7, wherein said tubes are fluidly connected to a tubing comprising multiple lumen, wherein the number of lumen equals the number of tubes.

9. The centrifuge bag of claim 8, wherein one of said outlet tubes is fluidly connected at its distal end to a bent fitting.

10. The centrifuge bag of claim 1, wherein said fluid comprises two or more components which separate into two or more fractions at varying radial distances within said bag during centrifugation, wherein a predetermined fraction is collected from said bag.

11. The centrifuge bag of claim 10, wherein said fluid is introduced into said bag via said inlet tube, and said predetermined fraction is withdrawn from said bag via said outlet tube.

12. The centrifuge bag of claim 10, wherein said fluid comprises whole blood and said predetermined fraction is platelet rich plasma, platelet poor plasma, white blood cells or red blood cells.

13. The centrifuge bag of claim 1, wherein said flexible sheets are polyvinyl chloride, polyethylene, polyurethane, ethylene vinyl acetate or combinations thereof.

14. The centrifuge bag of claim 1, wherein said centrifuge bag comprises concentric indicator lines imprinted on said centrifuge bag for monitoring the separation of said whole blood components, and wherein the distal end of said outlet tube is positioned relative to a predetermined indicator line.

15. A method of separating components contained in a fluid and harvesting a predetermined component, said method comprising:
  a) providing a flexible centrifuge bag comprising:
    i) at least one inlet tube;
    ii) at least one outlet tube; and
    iii) upper and lower flexible sheets, said sheets having doughnut shaped configurations, inner perimeters defining a central core of said centrifuge bag, and outer perimeters, wherein said upper and lower sheets are superimposed and completely sealed together at their outer perimeters, thereby defining the outer perimeter of said centrifuge bag, and wherein said inlet and outlet tubes are sandwiched between said upper and lower sheets and extend from the central core of said centrifuge bag, such that when said upper and lower sheets are sealed together at their inner perimeters, said inlet and outlet tubes are sealed between said upper and lower sheets at the inner perimeter;
  b) providing a centrifuge rotor;
  c) securing said flexible centrifuge bag in a horizontal position in said centrifuge rotor, whereby said centrifuge bag is fixably rotatable with said centrifuge rotor;
  d) rotating said centrifuge rotor;
  e) providing said fluid to said rotating centrifuge bag via said inlet tube, whereby said components of said fluid separate radially into two or more fractions based on their densities; and
  f) removing a fraction containing said predetermined component from said rotating centrifuge bag via said outlet tube.

16. The method of claim 15, wherein said inlet tube has a distal end positioned at a first radial distance from the center axis of said centrifuge bag and said outlet tube has a distal end positioned at a second radial distance from the center axis of said centrifuge bag, said first radial distance being greater than said second radial distance.

17. The method of claim 16, wherein said inlet and outlet tubes are fluidly connected to a dual lumen tubing having an inlet lumen in fluid communication with the proximal end of said inlet tube and an outlet lumen in fluid communication with the proximal end of said outlet tube.

18. The method of claim 17, wherein the distal end of said outlet tube is in flow communication with said fraction containing said predetermined component.

19. The method of claim 18, wherein said fluid is anti-coagulated whole blood and said predetermined component is selected from the group consisting of platelets. platelet rich plasma, platelet poor plasma, white blood cells or red blood cells.

20. The method of claim 19, wherein said inlet lumen is fluidly connected to an anticoagulated whole blood source.

21. The method of claim 17, wherein said dual lumen tubing is prevented from completely rotating about its axis during rotation of said centrifuge.

22. An apparatus for separating one or more predetermined components contained in a fluid sample, comprising:
  a rotatable centrifuge rotor; and
  a flexible centrifuge bag for receiving and holding said sample, said centrifuge bag horizontally positionable within and rotatable with said centrifuge rotor, said centrifuge bag comprising:
    at least one inlet tube and at least one outlet tube; and
    upper and lower flexible sheets, said sheets having doughnut shaped configurations, inner perimeters defining a central core of said centrifuge bag, and outer perimeters, wherein said upper and lower sheets are superimposed and completely sealed together at their outer perimeters, thereby defining the outer perimeter of said centrifuge bag, and wherein said tubes are sandwiched between said upper and lower sheets and extend radially from the central core of said centrifuge bag toward the bag outer perimeter, whereby when said upper and lower sheets are sealed together at their inner perimeters, said tubes are sealed between said upper and lower sheets at the inner perimeter.

23. The apparatus of claim 22, further comprising a multiple lumen tubing fluidly connected to said tubes, wherein the number of lumen equals the number of tubes.

24. The apparatus of claim 22, wherein said centrifuge bag comprises a inlet tube for introducing said sample into said bag, said inlet tube having a first length, and a first outlet tube for withdrawing a predetermined component separated from said sample, said first outlet tube having a second length, wherein said first length is greater than said second length.

25. The apparatus of claim 24, wherein said components separate at varying radial distances within said centrifuge bag based on their densities, wherein the distal end of said first outlet tube is positioned to be in flow communication with a fraction containing said predetermined component.

26. The apparatus of claim 23, wherein said tubing is prevented from completely rotating about its axis during rotation of said centrifuge.

27. The apparatus of claim 22, further comprising a bent fitting fluidly connected at the distal end of at least one of said outlet tubes.

28. The apparatus of claim 27, said bent fitting has a configuration selected from the group consisting of a T shape, a curved T shape, a J shape, or an L shape.

29. The apparatus of claim 22, wherein said fluid is whole blood and said predetermined component is platelet rich plasma, platelet poor plasma, white blood cells or red blood cells.

30. The centrifuge bag of claim 22, wherein said centrifuge bag comprises concentric indicator lines imprinted on said centrifuge bag for monitoring the separation of said whole blood components, and wherein the distal end of said outlet tube is positioned relative to a predetermined indicator line.

31. A flexible centrifuge bag for separating components of a fluid sample, comprising:
   upper and lower flexible sheets, said sheets having doughnut shaped configurations, inner perimeters defining a central core of said centrifuge bag, and outer perimeters, wherein said upper and lower sheets are superimposed and completely sealed together at their outer perimeters thereby defining the outer perimeter of said centrifuge bag;
   an outer first processing compartment;
   an inner second processing compartment disposed between said first processing compartment and said core and having diametrically opposed first and second indentations on its inner surface, wherein said first and second processing compartments are separated by first and second inner seals;
   two diametrically opposed channels, wherein said channels provide fluid communication between said first processing chamber and said second processing chamber;
   at least one inlet tube sandwiched between said upper and lower sheets and radially extending from the center of said core for introducing said fluid sample into said first processing compartment; and
   at least one outlet tube for withdrawing a select component from said second processing compartment, said outlet tube being sandwiched between said upper and lower sheets and extending across the diameter of said core, wherein one end of said outlet tube is proximal to said first indentation and the other end of said outlet tube is proximal to said second indentation, whereby when said upper and lower sheets are sealed together at their inner perimeters said inlet and outlet tubes are sealed between said upper and lower sheets at the inner perimeter.

32. The centrifuge bag of claim 31, wherein said first and second inner seals are C-shaped seals, wherein the concave sides of said first and second seals face each other, and wherein the ends of said seals define said channels.

33. The centrifuge bag of claim 31, wherein said tubes are fluidly connected to a multi lumen tubing.

34. The centrifuge bag of claim 33, said inlet tube is in fluid communication at its proximal end with an inlet lumen of a multi lumen tubing.

35. The centrifuge bag of claim 33, in said outlet tube is in fluid communication at its axis with an outlet lumen of a multi lumen tubing.

36. The centrifuge bag of claim 35, wherein said fluid sample is anticoagulated whole blood.

37. The centrifuge bag of claim 36, wherein said first processing compartment separates said whole blood into a red blood cell fraction and a platelet suspension.

38. The centrifuge bag of claim 37, wherein said second processing compartment separates platelets from said platelet suspension, wherein said platelets or white blood cells collect in said indentations.

39. The centrifuge bag of claim 31, wherein said components separated radially within said centrifuge bag base on their densities.

40. The centrifuge bag of claim 31, wherein said centrifuge bag comprises concentric indicator lines imprinted on said centrifuge bag for monitoring the separation of said whole blood components, and wherein the distal end of said outlet tube is positioned relative to a predetermined indicator line.

41. A flexible centrifuge bag for separating components of a fluid sample, comprising:
   upper and lower flexible sheets, said sheets having doughnut shaped configurations, inner perimeters defining a central core of said centrifuge bag, and outer perimeters, wherein said upper and lower sheets are superimposed and completely sealed together at their outer perimeters, thereby defining the outer perimeter of said centrifuge bag;
   a first C-shaped inner seal between said outer perimeter and said inner perimeter and having a first indentation on its concave side;
   a second C-shaped inner seal between said outer perimeter and said inner perimeter and having a second indentation on its concave side, wherein the concave side of said first inner seal faces the concave side of said second inner seal, and wherein said first and second indentations are diametrically opposed;
   a first channel defined by a first end of said first inner seal and a first end of said second inner seal;
   a second channel defined by a second end of said first inner seal and a second end of said second inner seal;
   an inlet tube sandwiched between said upper and lower sheets and extending from the center of the core of said centrifuge bag; and
   an outlet tube sandwiched between said upper and lower sheets and extending across the diameter of said core, wherein one end of said outlet tube is proximal to said first indentation and the other end of said outlet tube is proximal to said second indentation, whereby when said upper and lower sheets are sealed together at their inner perimeters, said inlet and outlet tubes are sealed between said upper and lower sheets at the inner perimeter.

42. The centrifuge bag of claim 41, wherein said outer perimeter together with said first and second inner seals define a first processing compartment.

43. The centrifuge bag of claim 41, wherein said inner perimeter together with said first and second inner seals define a second processing compartment.

44. The centrifuge bag of claim 41, wherein the distal end of said inlet tube is in fluid communication with said first processing compartment.

45. The centrifuge bag of claim 41, wherein said tubes are fluidly connected to a multiple lumen tubing comprising an inlet lumen an outlet lumen.

46. The centrifuge bag of claim 45, wherein said inlet tube is fluidly connected at its proximal end to said inlet lumen.

47. The centrifuge bag of claim 45, wherein said outlet tube is fluidly connected at its axis to said outlet lumen.

48. The centrifuge bag of claim 41, wherein said fluid sample is anticoagulated whole blood.

49. The centrifuge bag of claim 41, wherein said centrifuge bag comprises concentric indicator lines imprinted on said centrifuge bag for monitoring the separation of said whole blood components, and wherein the distal end of said outlet tube is positioned relative to a predetermined indicator line.

50. A disposable centrifuge bag for harvesting platelets from anticoagulated whole blood, comprising:
  upper and lower flexible sheets, said sheets having doughnut shaped configurations, inner perimeters defining a central core of said centrifuge bag, and outer perimeters, wherein said upper and lower sheets are superimposed and completely sealed together at their outer and inner perimeters;
  a first processing compartment for receiving said whole blood and separating said whole blood into a red blood cell fraction and a platelet suspension fraction;
  a second processing compartment for separating platelets from said platelet suspension fraction;
  channels for directing said platelet suspension fraction from said first processing compartment into said second processing compartment;
  an inlet tube for introducing whole blood into said first processing compartment; and
  an outlet tube for removing said platelets from said second processing compartment.

51. The centrifuge bag of claim 50, wherein said inlet tube extends radially from said central core and is sealed between the upper and lower sheets at the inner perimeter.

52. The centrifuge bag of claim 50, wherein said second processing chamber comprises diametrically opposed first and second wells for collecting and holding said platelets.

53. The centrifuge bag of claim 50, wherein said outlet tube extends across the diameter of said core and is sealed between said upper and lower sheets at the inner perimeter of said bag, wherein one end of said outlet tube is proximal to said first well and the other end of said outlet tube is proximal to said second well.

54. The centrifuge bag of claim 50, wherein said tubes are fluidly connected to a multiple lumen tubing comprising an inlet lumen and an outlet lumen.

55. The centrifuge bag of claim 54, wherein said inlet tube is fluidly connected at its proximal end to said inlet lumen.

56. The centrifuge bag of claim 54, wherein said outlet tube is fluidly connected at its axis to said outlet lumen.

57. The centrifuge bag of claim 50, wherein said red blood cell fraction and said platelet suspension separate from said whole blood in a path that extends radially from the rotational axis.

58. The centrifuge bag of claim 50, wherein said centrifuge bag comprises concentric indicator lines imprinted on said centrifuge bag for monitoring the separation of said whole blood components, and wherein the distal end of said outlet tube is positioned relative to a predetermined indicator line.

59. An apparatus for harvesting platelets from whole blood, comprising:
  a) a rotatable centrifuge rotor; and
  b) a flexible centrifuge bag comprising:
    upper and lower flexible sheets, said sheets having doughnut shaped configurations, inner perimeters defining a central core of said centrifuge bag, and outer perimeters, wherein said upper and lower sheets are superimposed and completely sealed together at their outer and inner perimeters;
    a first processing compartment for receiving said whole blood and separating said whole blood into a red blood cell fraction and a platelet suspension fraction;
    a second processing compartment for separating platelets from said platelet suspension fraction;
    channels for directing said platelet suspension fraction from said first processing compartment into said second processing compartment;
    an inlet tube for introducing whole blood into said first processing compartment; and
    an outlet tube for removing said platelets from said second processing compartment.

60. The apparatus of claim 59, wherein said inlet tube extends radially from said central core and is sealed between the upper and lower sheets at the inner perimeter.

61. The apparatus of claim 59, wherein said second processing chamber comprises diametrically opposed first and second wells for collecting and holding said platelets.

62. The apparatus of claim 59, wherein said outlet tube extends across the diameter of said core and is sealed between said upper and lower sheets at the inner perimeter of said bag, wherein one end of said outlet tube is proximal to said first well and the other end of said outlet tube is proximal to said second well.

63. The centrifuge bag of claim 59, wherein said tubes are fluidly connected to a multiple lumen tubing comprising an lumen and an outlet lumen.

64. The apparatus of claim 63, wherein said inlet tube is fluidly connected at its proximal end to said inlet lumen.

65. The apparatus of claim 63, wherein said outlet tube is fluidly connected at its axis to said outlet lumen.

66. The apparatus of claim 63, wherein said tubing is prevented from completely rotating about its axis during rotation of said centrifuge rotor.

67. The apparatus of claim 59, wherein said red blood cell fraction and said platelet suspension separate from said whole blood in a path that extends radially from the rotational axis.

68. A method for separating components contained in a fluid, comprising
  a) providing a flexible centrifuge bag comprising:
    i) upper and lower flexible sheets, said sheets having doughnut shaped configurations, inner perimeters defining a central core of said centrifuge bag, and outer perimeters, wherein said upper and lower sheets are superimposed and completely sealed together at their outer perimeters, thereby defining the outer perimeter of said centrifuge bag;
    ii) a first processing compartment;
    iii) a second processing compartment disposed between said first processing compartment and said core, said second processing compartment having two diametrically opposed indentations on the inner surface;

iv) two diametrically opposed channels, wherein said channels provide fluid communication between said first processing compartment and said second processing compartment;

v) an inlet tube for introducing said fluid into said first processing compartment, said inlet tube sandwiched between said upper and lower sheets and radially extending from the center of said core; and vi) an outlet tube for withdrawing a select one of said separated components from said second processing compartment, said outlet tube sandwiched between said upper and lower sheets and extending across the diameter of said core, wherein one end of said outlet tube is proximal to said first indentation and the other end of said outlet tube is proximal to said second indentation, whereby when said upper and lower sheets are sealed together at their inner perimeters, said inlet and outlet tubes are sealed between said upper and lower sheets at the inner perimeter;

b) providing a centrifuge rotor;

c) securing said flexible centrifuge bag in said centrifuge rotor, whereby said centrifuge bag is fixably rotatable with said centrifuge;

d) rotating said centrifuge rotor;

e) providing said fluid to said centrifuge bag via said inlet tube, whereby said components of said fluid separate radially into fractions based on their densities until said select component flows through said channels into said second processing compartment; and f) removing one or more of said components from said second processing compartment via said outlet tube.

69. The centrifuge bag of claim 68, wherein said tubes are fluidly connected to a multiple lumen tubing comprising an inlet lumen and an outlet lumen.

70. The method of claim 69, wherein said inlet tube is fluidly connected at its proximal end to said inlet lumen.

71. The method of claim 69, wherein said outlet tube is fluidly connected at its axis to said outlet lumen.

72. The method of claim 68, wherein said removed components are platelet rich plasma, platelet poor plasma, white blood cells or red blood cells.

73. A method for separating components contained in a fluid sample, comprising:

a) providing a flexible centrifuge bag for receiving said fluid sample, comprising:

i) upper and lower flexible sheets, said sheets having doughnut shaped configurations, inner perimeters defining a central core of said centrifuge bag, and outer perimeters, wherein said upper and lower sheets are superimposed and completely sealed together at their outer perimeters, thereby defining the outer perimeter of said centrifuge bag;

ii) a first C-shaped inner seal between said outer perimeter and said inner perimeter and having a first indentation on its concave side;

iii) a second C-shaped inner seal between said outer perimeter and said inner perimeter and having a second indentation on its concave side, wherein the concave side of said first C-shaped inner seal faces the concave side of said second C-shaped inner seal, and wherein said first and second indentations are diametrically opposed;

iv) a first channel defined by a first end of said first inner seal and a first end of said second inner seal;

v) a second channel defined by a second end of said first inner seal and a second end of said second inner seal;

vi) an inlet tube sandwiched between said upper and lower sheets and extending from the center of the core of said centrifuge bag to a point near said outer perimeter; and vii) an outlet tube sandwiched between said upper and lower sheets and extending across the diameter of said core, wherein one end of said outlet tube is proximal to said first indentation and the other end of said outlet tube is proximal to said second indentation, whereby when said upper and lower sheets are sealed together at their inner perimeters, said inlet and outlet tubes are sealed between said upper and lower sheets at the inner perimeter;

b) providing a centrifuge rotor;

c) securing said flexible centrifuge bag in said centrifuge rotor, whereby said centrifuge bag is fixably rotatable with said centrifuge rotor;

d) rotating said centrifuge rotor;

e) providing said fluid to said centrifuge bag via said inlet tube, whereby said components of said fluid separate radially into fractions based on their densities;

f) terminating said providing when a selected one of said components flows through said channels and collects in said indentations; and g) removing one or more of said separated components from said centrifuge bag via second outlet tube.

74. The centrifuge bag of claim 73, wherein said tubes are fluidly connected to a multiple lumen tubing comprising an inlet lumen and an outlet lumen.

75. The method of claim 74, wherein said inlet tube is fluidly connected at its proximal end to said inlet lumen.

76. The method of claim 74, wherein said outlet tube is fluidly connected at its axis to said outlet lumen.

77. A flexible centrifuge bag for separating components of a fluid sample, comprising:

upper and lower flexible sheets, said sheets having doughnut shaped configurations, inner perimeters defining a central core of said centrifuge bag, and outer perimeters, wherein said upper and lower sheets are superimposed and completely sealed together at their outer perimeters thereby defining the outer perimeter of said centrifuge bag;

an outer compartment;

an inlet port in said lower sheet and in fluid communication with said outer compartment;

an inner compartment disposed between said outer compartment and said core, wherein said inner and outer compartments are separated by first and second inner seals;

first and second channels, wherein said channels are diametrically opposed and provide fluid communication between said outer compartment and said inner compartment;

first and second outlet ports in said lower sheet and in fluid communication with said first and second channels, respectively;

an inlet tube having its distal end in fluid communication with said inlet port and fixed to the outer surface of said lower sheet and radially extending from the center of said core; and an outlet tube fixed to the outer surface of said lower sheet and extending across the diameter of said core, wherein one end of said outlet tube is in fluid communication with said first outlet port and the other end of said outlet tube is in fluid communication with said second outlet port.

78. The centrifuge bag of claim 77, wherein said tubes are fluidly connected to a multiple lumen tubing comprising an inlet lumen and an outlet lumen.

79. The centrifuge bag of claim 78, wherein said inlet tube is fluidly connected at its proximal end to said inlet lumen.

80. The centrifuge bag of claim 78, wherein said outlet tube is fluidly connected at its axis to said outlet lumen.

81. The centrifuge bag of claim 78, wherein said fluid sample is whole blood.

82. The centrifuge bag of claim 77, wherein said centrifuge bag comprises concentric indicator lines imprinted on said centrifuge bag for monitoring the separation of said whole blood components, and wherein the distal end of said outlet tube is positioned relative to a predetermined indicator line.

83. A flexible centrifuge bag for separating components of a fluid sample, comprising:
   upper and lower flexible sheets, said sheets having doughnut shaped configurations, inner perimeters defining a central core of said centrifuge bag and outer perimeters, wherein said upper and lower sheets are superimposed and completely sealed together at their outer perimeters, thereby defining the outer perimeter of said centrifuge bag;
   a first C-shaped inner seal between said outer perimeter and said inner perimeter;
   an inlet port in said lower sheet and positioned between said outer perimeter and said first inner seal for introducing said fluid into said centrifuge bag;
   a second C-shaped inner seal between said outer perimeter and said inner perimeter, wherein the concave side of said first inner seal faces the concave side of said second inner seal;
   a first channel defined by a first end of said first inner seal and a first end of said second inner seal;
   a second channel defined by a second end of said first inner seal and a second end of said second inner seal;
   first and second outlet ports in said lower sheet and in fluid communication with said first and second channels, respectively, for removing a select one of said components;
   an inlet tube in fluid communication with said inlet port, wherein said inlet tube is fixed to the outer surface of said lower sheet and extends from the center of the core of said centrifuge bag; and
   an outlet tube having first and second ends in fluid communication with said first and second outlet ports, respectively, wherein said outlet tube is fixed to the outer surface of said lower sheet and extends across the diameter of said core.

84. The centrifuge bag of claim 83, wherein said outer perimeter together with said first and second inner seals define an outer compartment.

85. The centrifuge bag of claim 83, wherein said inner perimeter together with said first and second inner seals define an inner compartment.

86. The centrifuge bag of claim 83, wherein said tubes are fluidly connected to a multiple lumen tubing comprising at least one inlet lumen and at least one outlet lumen.

87. The centrifuge bag of claim 86, wherein said inlet tube is fluidly connected at its proximal end to said inlet lumen.

88. The centrifuge bag of claim 86, wherein said outlet tube is fluidly connected at its axis to said outlet lumen.

89. The centrifuge bag of claim 83, wherein said fluid sample is anticoagulated whole blood.

90. The centrifuge bag of claim 89, wherein said whole blood separates radially into an outer red blood cell fraction and an inner platelet rich plasma fraction.

91. The centrifuge bag of claim 83, wherein said centrifuge bag comprises concentric indicator lines imprinted on said centrifuge bag for monitoring the separation of said whole blood components, and wherein the distal end of said outlet tube is positioned relative to a predetermined indicator line.

92. A flexible centrifuge bag for separating components of a fluid sample, comprising:
   upper and lower flexible sheets, said sheets having doughnut shaped configurations, inner perimeters defining a central core of said centrifuge bag, and outer perimeters, wherein said upper and lower sheets are superimposed and completely sealed together at their outer perimeters thereby defining the outer perimeter of said centrifuge bag;
   a first C-shaped inner seal between said outer perimeter and said inner perimeter;
   a second C-shaped inner seal between said outer perimeter and said inner perimeter, wherein the concave side of said first inner seal faces the concave side of said second inner seal;
   a first channel defined by a first end of said first inner seal and a first end of said second inner seal;
   a second channel defined by a second end of said first inner seal and a second end of said second inner seal;
   an inlet tube for introducing said fluid into said first centrifuge bag, wherein said inlet tube is sealed between said upper and lower sheets and extends from the center of the core of said centrifuge bag; and
   an outlet tube having first and second ends in fluid communication with said first and second channels, respectively, wherein said outlet tube is sealed between said upper and lower sheets and extends across the diameter of said core.

93. The centrifuge bag of claim 92, wherein said outer perimeter together with said first and second inner seals define an outer perimeter.

94. The centrifuge bag of claim 92, wherein said inner perimeter together with said first and second inner seals define an inner compartment.

95. The centrifuge bag of claim 92, wherein said tubes are fluidly connected to a multiple lumen tubing comprising an inlet lumen and an outlet lumen.

96. The centrifuge bag of claim 95, wherein said inlet tube is fluidly connected at its proximal end to said inlet lumen.

97. The centrifuge bag of claim 95, wherein said outlet tube is fluidly connected at its axis to said outlet lumen.

98. The centrifuge bag of claim 92, wherein said fluid sample is anticoagulated whole blood.

99. The centrifuge bag of claim 92, wherein said centrifuge bag comprises concentric indicator lines imprinted on said centrifuge bag for monitoring the separation of said whole blood components, and wherein the distal end of said outlet tube is positioned relative to a predetermined indicator line.

* * * * *

UNITED STATES PATENT AND TRADEMARK OFFICE
CERTIFICATE OF CORRECTION

PATENT NO. : 6,827,863 B2
APPLICATION NO. : 10/462426
DATED : December 7, 2004
INVENTOR(S) : Dolecek et al.

It is certified that error appears in the above-identified patent and that said Letters Patent is hereby corrected as shown below:

Column 60, line 35, that portion of the claim reading "platelets. platelet" should read --platelets, platelet--.

Column 61, line 19, that portion of the claim reading "claim 27, said" should read --claim 27, wherein said--.

Column 62, line 7, that portion of the claim reading "claim 33, said" should read --claim 33, wherein said--.

Column 62, line 10, that portion of the claim reading "claim 33, in said" should read --claim 33, wherein said--.

Column 62, line 23, that portion of the claim reading "bag base on" should read --bag based on--.

Column 64, line 40, that portion of the claim reading "an lumen" should read --an inlet lumen--.

Column 66, line 42, that portion of the claim reading "perimeters thereby" should read --perimeters, thereby--.

Column 68, line 45, that portion of the claim reading "outer perimeter" should read --outer compartment--.

Signed and Sealed this

Twenty-seventh Day of March, 2007

JON W. DUDAS
*Director of the United States Patent and Trademark Office*